US006893638B2

(12) United States Patent
Anderson et al.

(10) Patent No.: US 6,893,638 B2
(45) Date of Patent: May 17, 2005

(54) METHODS FOR TREATING B CELL LYMPHOMA USING CD80-SPECIFIC ANTIBODIES

(76) Inventors: Darrell R. Anderson, 29246 Lawrence Welk, Escondido, CA (US) 92029; Peter Brams, 4303 Proctor Pl., San Diego, CA (US) 92116; Nabil Hanna, 16016 Camino Deliciada, Rancho Santa Fe, CA (US) 92067; William S. Shestowsky, 1155 Thomas Ave., San Diego, CA (US) 92109; Cheryl Heard, 1225 Via Montoro, Encinitas, CA (US) 92024

( * ) Notice: Subject to any disclaimer, the term of this patent is extended or adjusted under 35 U.S.C. 154(b) by 0 days.

(21) Appl. No.: 09/758,173

(22) Filed: Jan. 12, 2001

(65) Prior Publication Data

US 2001/0024648 A1 Sep. 27, 2001

Related U.S. Application Data

(62) Division of application No. 09/383,916, filed on Aug. 26, 1999, which is a division of application No. 08/487,550, filed on Jun. 7, 1995, now Pat. No. 6,113,898.

(51) Int. Cl.[7] ...................... A61K 39/395; C07K 16/28
(52) U.S. Cl. .............................. 424/153.1; 424/130.1; 424/133.1; 424/138.1; 424/141.1; 424/143.1; 424/144.1; 424/155.1; 424/173.1; 424/174.1; 530/387.1; 530/387.3; 530/387.7; 530/388.1; 530/388.2; 530/388.22; 530/388.7; 530/388.73; 530/388.8
(58) Field of Search .......................... 424/130.1, 133.1, 424/144.1, 138.1; 530/387.1, 388.2, 388.73

(56) References Cited

U.S. PATENT DOCUMENTS

| | | | |
|---|---|---|---|
| 4,816,397 A | | 3/1989 | Boss |
| 4,816,567 A | | 3/1989 | Cabilly |
| 5,116,964 A | | 5/1992 | Capon |
| 5,304,635 A | * | 4/1994 | Imam et al. |
| 5,885,579 A | | 3/1999 | Linsley |
| 6,162,432 A | | 12/2000 | Wallner |

FOREIGN PATENT DOCUMENTS

| | | |
|---|---|---|
| EP | 0 173 494 A2 | 3/1986 |
| EP | 0 451 216 B1 | 10/1991 |
| EP | 0 171 496 B1 | 5/1993 |
| EP | 0 194 276 B1 | 8/1993 |
| EP | 0 555 880 A2 A3 | 8/1993 |
| EP | 0 239 400 B1 | 8/1994 |
| EP | 0 682 040 A1 | 11/1995 |
| GB | 2 177 096 A | 3/1986 |
| WO | WO 92/06193 | 4/1992 |
| WO | WO 93/09812 | 5/1993 |
| WO | WO 94/28912 | 12/1994 |
| WO | WO 95/06481 | 3/1995 |
| WO | WO 95/06666 | 3/1995 |
| WO | WO 98/19706 | 5/1998 |

OTHER PUBLICATIONS

Kandasamy et al. Blood 11 (Par 1): p. 608a (2001).*
Delmer Biotechnology 12:320 (1994).*
Dillman J. Clin Oncol. 12:1497–1515 (1994).*
Falini et al. Lancet 339:1195–1196 (1992).*
Delasie et al. Blood 82:2845–2852 (1993).*
Mundo et al. Blood 83:793–798 (1994).*
Kuchroo et al., "B7–1 and B7–2 Costimulatory Molecules Activate Differentially the Th1/Th2 Developmental Pathways: Application to Autoimmune Disease Therapy," Cell, 80:707–718 (1995).
Lenschow et al., "Inhibition of Transplant Rejection Following Treatment with Anti–B7–2 and Anti–B7–1 Antibodies," Transplantation 60:1171–1178 (1995).
Lenschow et al. "Differential Effects of Anti–B7–1 and Anti–B7–2 Monoclonal Antibody Treatment on the Development of Diabetes in the Nonobese Diabetic Mouse," J. Exp. Med. 181:1146–1155 (1995).
Nakajima et al., "Preferential dependence of autoantibody production in murine lupus on CD86 co–stimulatory molecule," Euro. J. Immunol. 25(11):3060–3069 (Nov. 1995).
Van Gool et al., "Synergy Between Cyclosporin A and a Monoclonal Antibody to B7 in Blocking Alloantigen–Induced T–Cell Activation," Blood, 83:176–183 (1994).
Wettendorf et al., "Generation of Humanized Fab Fragments of B7–24 mAb, An Antibody with Potential Use in the Prevention of Graft Rejection and Development of Graft–Versus–Host Disease," Med. Fac. Landbouww. Univ. Gent. 60(4):2057–2063, Published Sep. 27, 1995—not early enough to be valid prior art.
Armitage, R.J., et al., Molecular and biologial characterization of a murine ligand for CD40, Nature, 1992, 357:80–82.
Asuma, M. et al., Functional Expression of B7/BB1 on Activated T Lymphocytes, J. Exp. Med., 1992, 177:845–850.
Ben–Nun, A. et al., The rapid isolation of clonable antigen–specific T lymphocyte lines capable of mediating autoimmune encephalomyelitis, Eur J. Immunol., 1981, 11:195–199.
Blazar, B.R. et al., Infusion of anti–B7.1 (CD80) and anti–B7.2 (CD86) monoclonal antibodies inhibits murine graft–versus–host disease lethality in part via direct effects on CD4+ and CD8+ T cells, J Immunol., 1996, 157:3250–3259.
Capon, D.J., et al., Designing CD4 immunoadhesins for AIDS therapy, Nature, 1989, 337, 525–531.
Dautigny, A., et al., Molecular cloning and nucleotide sequence of a cDNA clone coding for rat brain myelin proteolipid, FEBS Lett., 1985, 188(1):33–36.

(Continued)

Primary Examiner—Phillip Gambel
(74) Attorney, Agent, or Firm—Pillsbury Winthrop LLP

(57) ABSTRACT

The present invention relates to methods for treating B cell lymphoma using CD80-specific antibodies.

5 Claims, 22 Drawing Sheets

OTHER PUBLICATIONS

Durie, F.H., et al., The role of CD40 and its ligand (gp39) in peripheral and central tolerance and its contribution to autoimmune disease, Research in Immunology, 1994, 145(3), 200–205 & 244–249.

Durie, F.H., et al., Prevention of collagen–induced arthritis with an antibody to gp39, the lignad for CD40, Science, 1993, 261:1328–1330.

Freeman, G.J. et al., Uncovering of functional alternative CTLA–4 counter–receptor in B7–deficient mice, Science, 1993, 262:907–909.

Freeman, G.J. et al., B7, A new member of the Ig Superfamily with unique expression on activated and neoplastic B cells, J of Immunol., 1989, 143:2714–2722.

Freeman, G.J. et al., Cloning of B7–2: a CTLA–4 counter–receptor that costimulates human T cell proliferation, Science, 1993, 262:909–911.

Gerritse, K., et al., CD40–CD40 ligand interactions in experimental allergic encephalomyelitis and multiple sclerosis, Proc. Natl. Acad. Sci. USA, 1996, 93:2499–2504.

Gottlieb, A, et al., Results of a single–dose, dose–escalating trial of an anti–B7.1 monoclonal antibody (IDEC–114) in patients with psoriasis, J Invest Dermatol., 2000, 114:840, Abstract No. 546.

Gottlieb, A. et al., Clinical and histologic response to single–dose treatment of moderate to severe psoriasis with an anti–CD80 monoclonal antibody, J Am Acad Dermatol., 2002, 47:692–700.

Guinan, E.C. et al., Pivotal role of the B7:CD28 pathway in transplantation tolerance and tumor immunity, Blood. 1994, 84:3261–3282.

Hafler, D.A., et al., The potential of restricted T cell recognition of myelin basis protein epitopes in the therapy of multiple sclerosis, Ann. NY Acad. Sci., 1991, 636:251–265.

Hariharan et al., "In vitro and in vivo studies demonstating the effectiveness of IDEC–114 and rituximab (Rituxan®) in therapy of B–cell lymphoma in experimental models; Confidential Report (laboratory notebook and data binder 2552, 2646, 2665, and 2671)," Jun. 29, 2001.

Hathcock, K.S. et al., Identification of an alternative CTLA–4 ligand costimulatory for T cell activation, Science, 1993, 262:905–907.

Hollenbaugh, D., et al., The human T cell antigen gp39, a member of the TNF gene family, is a ligand for the CD40 receptor: expression of a soluble form of gp39 with B cell co–stimulatory activity, The EMBO J., 1992, 11(12):4313–4321.

Janeway, C.A. et al., Signals and Signs for Lymphocyte Responses, 1994, 76:275–285.

Kahan, B.D., Immunosuppressive therapy, Curr Opin Immunol., 1992, 4:553–560.

Karpus, W.J., et al., CD4+ suppressor cells differentially affect the production of IFN–γ by effector cells of experimental autoimmune encephalomyelitis, J. Immunol., 1989, 143:3492–3497.

Laman, J., et al., The role of gp39 (CD40 ligand) in EAE and MS, Journal of Neuroimmunology, 1994, 54(1–2):175.

Lederman, S., et al., Identification of a novel surface protein on activated CD4+ T cells that induces contact–dependent B cell differentiation (Help), J. Exp. Med., 1992, 175:1091–1101.

Lider, O., et al., Suppression of experimental autoimmune encephalomyelitis by oral administration of myelin basic protein. J. Immunol., 1989, 142:748–752.

Linsley, P.S. et al., The role of the CD28 receptor during T cell responses to antigen, Annu Rev Immunol., 1993, 11:191–212.

Linsley, P.S. et al., T–cell antigen CD28 mediates adhesion with B cells by interacting with activation antigen B7/BB–1, Proc. Natl. Acad., 1990, 87:5031–5035.

McCafferty, J., et al., Phage antibodies: filamentous phage displaying antibody variable domains, Nature, 1990, 348:552–554.

Miller, A., et al., Antigen–driven bystander suppression after oral administration of antigens, J. Exp. Med., 1991, 174:791–798.

Mokhtarion, F., et al., Adoptive transfer of myelin basic protein–sensitized T cells produces chronic relapsing demyelinating disease in mice, Nature, 1984, 309:356–358.

Morrison, S., et al., Chimeric human antibody molecules: mouse antigen–binding domains with human constant region domains, Proc. Natl. Acad, Sci. U.S.A., 1985, 81:6851–6855.

Nickoloff, B.J. et al., T lymphocytes in skin lesions of psoriasis and mycosis fungoides express B7–1: a ligand for CD28, Blood, 1994, 83:2580–2586.

Noelle, R.J., et al., A 39–kDa protein on activated helper T cells binds CD40 and transduces the signal for cognate activation of B cells, Proc. Natl. Acad. Sci. USA, 1992, 89:6550–6554.

Olsson, L., et al., Human–human monoclonal antibody–producing hybridomas: technical aspects, Meth, Enzymol., 1982, 92:3–17.

Perrin, P.J. et al., Opposing effects of CTLA4–lg and anti–CD80 (B7–1) plus anti–CD86 (B7–2) on experimental allergic encephalomyelitis, J Neuroimmunol., 1996, 65:31–39.

Pesoa, S.A., et al., Regulation of experimental allergic encephalomyelitis, Part 5, Role of the recipient in suppressor cell induction, J. Neuroimmunol, 1984, 7:131–135.

Pettinelli, C.B., et al., Adoptive transfer of experimental allergic encephalomyelitis in SJL/J mice after in vitro activation of lymph node cells by myelin basic protein: requirement for Lyt $1^+$ $2^-$ T lymphocytes, J. Immunol., 1979, 127:1420–1423.

Sobel, R.A., et al., Acute experimental allergic encephalomyelitis in SJL/J mice induced by a synthetic peptide of myelin proteolipid protein, J. Neuropathol. Exp. Neurol., 1990, 49(5):468–479.

Stamenkovid, I., et al., A B–lymphocyte activation molecule related to the nerve growth factor receptor and induced by cytokines in carcinomas, The EMBO J., 1989, 8(5), 1403–1410.

Suvas, S. et al., Distinct role of CD80 and CD86 in the regulation of the activation of B cell and B cell lymphoma, J Biol Chem., 2002, 277:7766–7775.

Takeda S., et al., Constriction of chimaeric processed immunoglobulin genes containing mouse variable and human constant region sequences, Nature, 1985, 314(4):452–454.

Teng, N. H. et al., Construction and testing of mouse–human heteromyelomas for human monoclonal antibody production, Proc. Natl. Acad. Sci. U.S.A., 1983, 80:7308–7312.

Tuohy, V.K., et al., Identification of an encephalitogenic determinant of myelin proteolipid protein for SJL mice, J. Immunol., 1989, 142:1523–1527.

Valle, A. et al., mAb 104, a new monoclonal antibody, recognizes the B7 antigen that is expressed on activated B cells and HTLV–1–transformed T cells, Immunology, 1990, 69:531–535.

Van der Veen, R. C. et al., The adoptive transfer of chronic relapsing experimental allergic encephalomyelitis with lymph node cells sensitized to myelin proteolipid protein, J. Neuroimmunol., 1989, 21:183–191.

Ward, E.S., et al., Binding activities of a repertoire of single immunoglobulin variable domains secreted from *Escherichia coli*, Nature, 1989, 341:544–546.

Ward, P.A., et al., Blocking of adhesion molecules in vivo as anti–inflammatory therapy, Ther Immunol., 1994, 1:165–171.

Yi–qun, Z. et al., Differential requirements for co–stimulatory signals from B7 family members by resting versus recently activated memory T cells towards soluble recall antigens, Int Immunol., 1996, 8:37–44.

Liu et al. "Co–stimulation of murine CD4 T cell growth: cooperation between B7 and heat–stable antigen", *Eur. J. Immunol.*, Nov. 1992, vol. 22, No. 11, pp. 2855–2859 (see entire reference).

Inaba et al. "The tissue distribution of the B7–2 co–stimulator in mice: abundant expression on dendritic cells in situ and during maturation in vitro", *J. Exp. Med.*, Nov. 1994, vol. 180, No. 5, pp. 1849–1860 (see entire reference).

Engel et al. "The B7–2 (B70) co–stimulatory molecule expressed by monocytes and actiated B lymphocytes is the CD86 differentiation antigen" *Blood*, Sep. 01, 1994, vol. 84, No. 5, pp. 1402–1407 (see entire document).

Newman et al. Primatization of recombinant antibodies for immunotherapy of human diseases: a macaque/human chimeric antibody against human CD4. *Biotechnology*, Nov. 1992, vol. 10, No. 11, pp. 1455–1460 (see entire reference).

Linsley, Peter S., et al., "Binding of the B Cell Activation ANtigen 87 to CD28 Costimulates T cell Proliferation and interleukin 2 mRNA Accumulation", *J. Exp. Med.*, (Mar. 1991), vol. 173, pp. 721–730.

J. Cohen; "New Protein Steals the Show as 'Costimulator' of T Cells", *Science*, Nov. 05, 1993), vol. 262, pp. 844–845.

* cited by examiner

FIG. 2

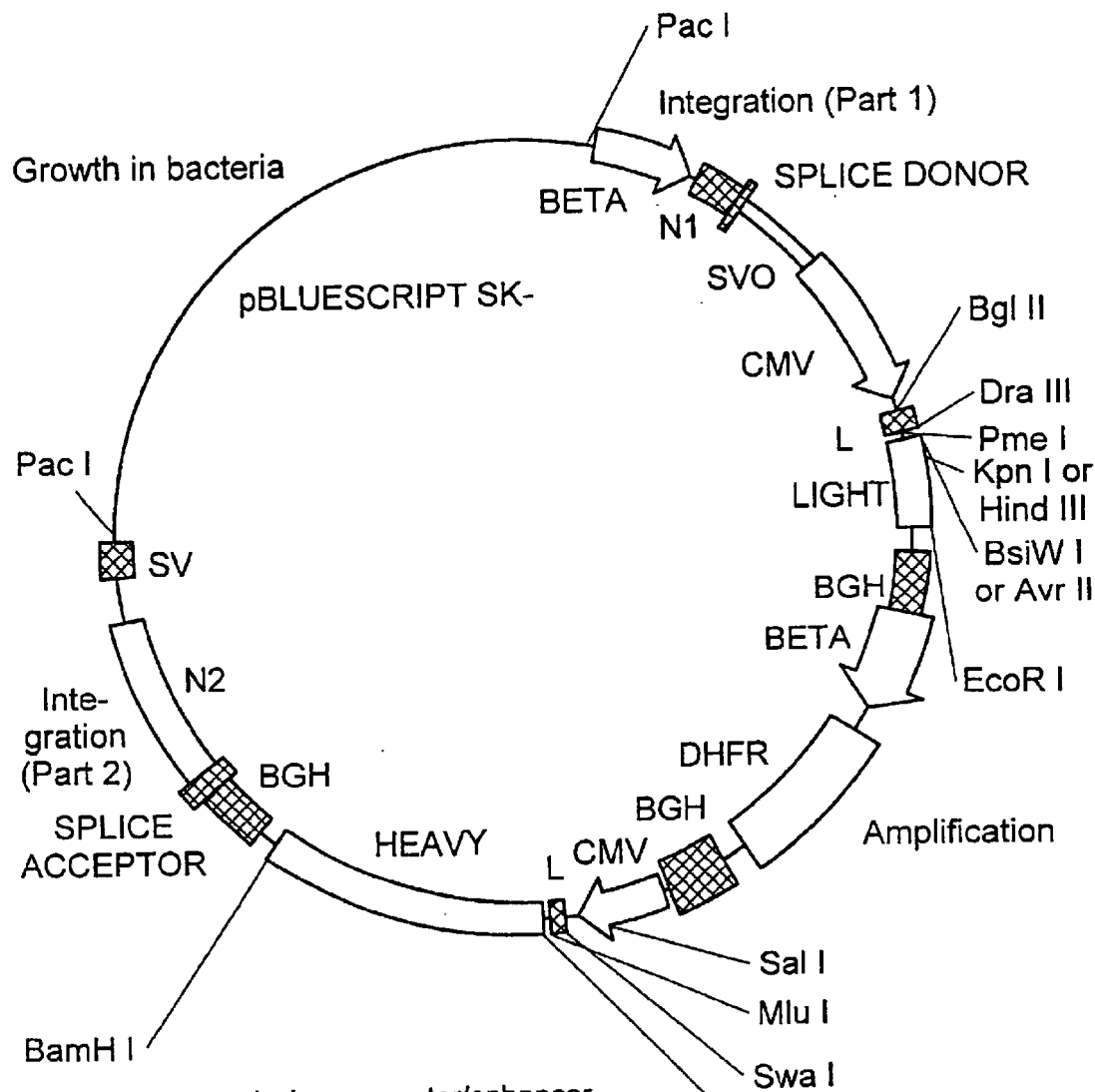

CMV = Cytomegalovirus promoter/enhancer
BETA = Mouse Beta globin major promoter
SVO = SV40 origin
BGH = Bovine growth hormone polyadenylation
SV = SV40 polyadenylation
N1 = Neomycin phosphotransferase exon 1
N2 = Neomycin phosphotransferase exon 2
LIGHT = Human immunonoglobulin kappa or lambda constant region
DHFR = Dihydrofolate Reductase
HEAVY = Human immunonoglobulin gamma 1 or gamma 4 PE constant region
L = Leader Monkey Serum Anti-B7.1 Titers Directed Against Cell Surface B7.1 on Transfected CHO Cells. Monkeys 1133-1139 were immunized with sB7.1. Monkeys 769-1146 were immunized with 50 million human B7 positive SB cells.

Inhibition of Radiolabeled sB7.1 Binding by sB7.1 Affinity-purified Monkey Antibodies in Presence of Unlabeled sB7 and MAb L307.4 Murine Anti-B7.1.

Inhibition of Binding of Radiolabeled Monkey 1135 and L307.4 Anti-B7.1 Antibodies to B7 Positive Human SB Cells by Competition With Affinity-Purified sB7.1.

Inhibition of Radiolabeled B7-Ig Binding to Activated Human Peripheral Blood T Cells by Competing With Unlabeled sB7.1 Murine Anti-B7.1 (L307.4) and Monkey 1127 Affinity-purified Serum Antibodies.

Inhibition of IL-2 Production in Mixed Lymphocyte Cultures by Anti-B7.1 Affinity-purified Monkey Serum Anibodies. Assays at some concentrations for certain monkeys were not done, due to limiting amounts of purified antibody.

LENGTH OF 7C10 LIGHT/PRIMATIZED: 705 bp; LISTED FROM: 1 TO: 705;
TRANSLATED FROM: 1 TO: 703 (ENTIRE REGION);
GENETIC CODE USED: UNIVERSAL; FRI, MAY 26, 1995 11:11 AM

```
FRAME 1  M   R   V   P   A   Q   L   L   G   L   L   L   L
         ATG AGG GTC CCC GCT CAG CTC CTG GGGCTC CTG CTG CTC
                 9          18          27          36

W   L   P   G   A   R   C   A   Y   E   L   T   Q   P   P
         TGG CTC CCA GGT GCA CGA TGT GCC TAT GAA CTG ACT CAG CCA CCC
                 45          54          63          72          81

S   V   S   V   S   P   G   Q   T   A   R   I   T   C   G
         TCG GTG TCA GTG TCC CCA GGA CAG ACG GCC AGG ATC ACC TGT GGG
                 90          99         108         117         126

G   D   N   S   R   N   E   Y   V   H   W   Y   Q   Q   K
         GGA GAC AAC AGT AGA AAT GAA TAT GTC CAC TGG TAC CAG CAG AAG
                135         144         153         162         171

P   A   R   A   P   I   L   V   I   Y   D   D   S   D   R
         CCA GCG CGG GCC CCT ATA CTG GTC ATC TAT GAT GAT AGT GAC CGG
                180         189         198         207         216

P   S   G   I   P   E   R   F   S   G   S   K   S   G   N
         CCC TCA GGGATC CCT GAG CGA TTC TCT GGC TCC AAA TCA GGGAAC
                225         234         243         252         261

T   A   T   L   T   I   N   G   V   E   A   G   D   E   A
         ACC GCC ACC CTG ACC ATC AAC GGGGTC GAG GCC GGGGAT GAG GCT
                270         279         288         297         306

D   Y   Y   C   Q   V   W   D   R   A   S   D   H   P   V
         GAC TAT TAC TGT CAG GTG TGG GAC AGG GCT AGT GAT CAT CCG GTC
                315         324         333         342         351

F   G   G   G   T   R   V   T   V   L   G   Q   P   K   A
         TTC GGA GGA GGGACC CGG GTG ACC GTC CTA GGT CAG CCC AAG GCT
                360         369         378         387         396

A   P   S   V   T   L   F   P   P   S   S   E   E   L   Q
         GCC CCC TCG GTC ACT CTG TTC CCG CCC TCC TCT GAG GAG CTT CAA
                405         414         423         432         441

A   N   K   A   T   L   V   C   L   I   S   D   F   Y   P
         GCC AAC AAG GCC ACA CTG GTG TGT CTC ATA AGT GAC TTC TAC CCG
                450         459         468         477         486
```

FIG. 8A - 1

```
G   A   V   T   V   A   W   K   A   D   S   S   P   V   K
GGA GCC GTG ACA GTG GCC TGG AAG GCA GAT AGC AGC CCC GTC AAG
    495         504         513         522         531

A   G   V   E   T   T   T   P   S   K   Q   S   N   N   K
GCG GGA GTG GAG ACC ACC ACA CCC TCC AAA CAA AGC AAC AAC AAG
    540         549         558         567         576

Y   A   A   S   S   Y   L   S   L   T   P   E   Q   W   K
TAC GCG GCC AGC AGC TAC CTG AGC CTG ACG CCT GAG CAG TGG AAG
    585         594         603         612         621

S   H   R   S   Y   S   C   Q   V   T   H   E   G   S   T
TCC CAC AGA AGC TAC AGC TGC CAG GTC ACG CAT GAA GGG AGC ACC
    630         639         648         657         666

V   E   K   T   V   A   P   T   E   C   S   .
GTG GAG AAG ACA GTG GCC CCT ACA GAA TGT TCA TGA
    675         684         693         702
```

FIG. 8A - 2

LENGTH OF 7C10 HEAVY/PRIMATIZED: 1431 bp; LISTED FROM: 1 TO: 1431
TRANSLATED FROM: 1 TO: 1429 (ENTIRE REGION);
GENETIC CODE USED: UNIVERSAL; FRI, MAY 26, 1995 11:11 AM

```
FRAME 1  M    K    H    L    W    F    F    L    L    L    V    A    A
         ATG  AAA  CAC  CTG  TGG  TTC  TTC  CTC  CTC  CTG  GTG  GCA  GCT
              9         18        27        36

P    R    W    V    L    S    Q    V    K    L    Q    Q    W    G    E
         CCC  AGA  TGG  GTC  CTG  TCC  CAG  GTG  AAG  CTG  CAG  CAG  TGG  GGC  GAA
              45        54        63        72        81

G    L    L    Q    P    S    E    T    L    S    R    T    C    V    V
         GGA  CTT  CTG  CAG  CCT  TCG  GAG  ACC  CTG  TCC  CGC  ACC  TGC  GTT  GTC
              90        99        108       117       126

S    G    G    S    I    S    G    Y    Y    Y    W    T    W    I    R
         TCT  GGT  GGC  TCC  ATC  AGC  GGT  TAC  TAC  TAC  TGG  ACC  TGG  ATC  CGC
              135       144       153       162       171

Q    T    P    G    R    G    L    E    W    I    G    H    I    Y    G
         CAG  ACC  CCA  GGG  AGG  GGA  CTG  GAG  TGG  ATT  GGC  CAT  ATT  TAT  GGT
              180       189       198       207       216

N    G    A    T    T    N    Y    N    P    S    L    K    S    R    V
         AAT  GGT  GCG  ACC  ACC  AAC  TAC  AAT  CCC  TCC  CTC  AAG  AGT  CGA  GTC
              225       234       243       252       261

T    I    S    K    D    T    S    K    N    Q    F    F    L    N    L
         ACC  ATT  TCA  AAA  GAC  ACG  TCC  AAG  AAC  CAG  TTC  TTC  CTG  AAC  TTG
              270       279       288       297       306

N    S    V    T    D    A    D    T    A    V    Y    Y    C    A    R
         AAT  TCT  GTG  ACC  GAC  GCG  GAC  ACG  GCC  GTC  TAT  TAC  TGT  GCG  AGA
              315       324       333       342       351

G    P    R    P    D    C    T    T    I    C    Y    G    G    W    V
         GGC  CCT  CGC  CCT  GAT  TGC  ACA  ACC  ATT  TGT  TAT  GGC  GGC  TGG  GTC
              360       369       378       387       396

D    V    W    G    P    G    D    L    V    T    V    S    S    A    S
         GAT  GTC  TGG  GGC  CCG  GGA  GAC  CTG  GTC  ACC  GTC  TCC  TCA  GCT  AGC
              405       414       423       432       441

T    K    G    P    S    V    F    P    L    A    P    S    S    K    S
         ACC  AAG  GGC  CCA  TCG  GTC  TTC  CCC  CTG  GCA  CCC  TCC  TCC  AAG  AGC
              450       459       468       477       486
```

FIG. 8B - 1

```
  T   S   G   G   T   A   A   L   G   C   L   V   K   D   Y
ACC TCT GGG GGC ACA GCG GCC CTG GGC TGC CTG GTC AAG GAC TAC
    495     504         513         522         531

F   P   E   P   V   T   V   S   W   N   S   G   A   L   T
TTC CCC GAA CCG GTG ACG GTG TCG TGG AAC TCA GGC GCC CTG ACC
    540     549         558         567         576

S   G   V   H   T   F   P   A   V   L   Q   S   S   G   L
AGC GGC GTG CAC ACC TTC CCG GCT GTC CTA CAG TCC TCA GGA CTC
    585     594         603         612         621

Y   S   L   S   S   V   V   T   V   P   S   S   S   L   G
TAC TCC CTC AGC AGC GTG GTG ACC GTG CCC TCC AGC AGC TTG GGC
    630     639         648         657         666

T   Q   T   Y   I   C   N   V   N   H   K   P   S   N   T
ACC CAG ACC TAC ATC TGC AAC GTG AAT CAC AAG CCC AGC AAC ACC
    675     684         693         702         711

K   V   D   K   K   A   E   P   K   S   C   D   K   T   H
AAG GTG GAC AAG AAA GCA GAG CCC AAA TCT TGT GAC AAA ACT CAC
    720     729         738         747         756

T   C   P   P   C   P   A   P   E   L   L   G   G   P   S
ACA TGC CCA CCG TGC CCA GCA CCT GAA CTC CTG GGG GGA CCG TCA
    765     774         783         792         801

V   F   L   F   P   P   K   P   K   D   T   L   M   I   S
GTC TTC CTC TTC CCC CCA AAA CCC AAG GAC ACC CTC ATG ATC TCC
    810     819         828         837         846

R   T   P   E   V   T   C   V   V   V   D   V   S   H   E
CGG ACC CCT GAG GTC ACA TGC GTG GTG GTG GAC GTG AGC CAC GAA
    855     864         873         882         891

D   P   E   V   K   F   N   W   Y   V   D   G   V   E   V
GAC CCT GAG GTC AAG TTC AAC TGG TAC GTG GAC GGC GTG GAG GTG
    900     909         918         927         936

H   N   A   K   T   K   P   R   E   E   Q   Y   N   S   T
CAT AAT GCC AAG ACA AAG CCG CGG GAG GAG CAG TAC AAC AGC ACG
    945     954         963         972         981

Y   R   V   V   S   V   L   T   V   L   H   Q   D   W   L
TAC CGT GTG GTC AGC GTC CTC ACC GTC CTG CAC CAG GAC TGG CTG
    990     999         1008        1017        1026
```

FIG. 8B - 2

```
 N   G   K   E   Y   K   C   K   V   S   N   K   A   L   P
AAT GGC AAG GAG TAC AAG TGC AAG GTC TCC AAC AAA GCC CTC CCA
    1035        1044        1053        1062        1071

A   P   I   E   K   T   I   S   K   A   K   G   Q   P   R
GCC CCC ATC GAG AAA ACC ATC TCC AAA GCC AAA GGG CAG CCC CGA
    1080        1089        1098        1107        1116

E   P   Q   V   Y   T   L   P   P   S   R   D   E   L   T
GAA CCA CAG GTG TAC ACC CTG CCC CCA TCC CGG GAT GAG CTG ACC
    1125        1134        1143        1152        1161

K   N   Q   V   S   L   T   C   L   V   K   G   F   Y   P
AAG AAC CAG GTC AGC CTG ACC TGC CTG GTC AAA GGC TTC TAT CCC
    1170        1179        1188        1197        1206

S   D   I   A   V   E   W   E   S   N   G   Q   P   E   N
AGC GAC ATC GCC GTG GAG TGG GAG AGC AAT GGG CAG CCG GAG AAC
    1215        1224        1233        1242        1251

N   Y   K   T   T   P   P   V   L   D   S   D   G   S   F
AAC TAC AAG ACC ACG CCT CCC GTG CTG GAC TCC GAC GGC TCC TTC
    1260        1269        1278        1287        1296

F   L   Y   S   K   L   T   V   D   K   S   R   W   Q   Q
TTC CTC TAC AGC AAG CTC ACC GTG GAC AAG AGC AGG TGG CAG CAG
    1305        1314        1323        1332        1341

G   N   V   F   S   C   S   V   M   H   E   A   L   H   N
GGG AAC GTC TTC TCA TGC TCC GTG ATG CAT GAG GCT CTG CAC AAC
    1350        1359        1368        1377        1386

H   Y   T   Q   K   S   L   S   L   S   P   G   K   .
CAC TAC ACG CAG AAG AGC CTC TCC CTG TCT CCG GGT AAA TGA
    1395        1404        1413        1422        1431
```

FIG. 8B - 3

LENGTH OF 7B6 LIGHT/PRIMATIZED: 720 bp; LISTED FROM: 1 TO: 720;
TRANSLATED FROM: 1 TO: 718 (ENTIRE REGION);
GENETIC CODE USED: UNIVERSAL; FRI, MAY 26, 1995 11:10 AM

```
FRAME 1  M    S    L    P    A    Q    L    L    G    L    L    L
         ATG  AGC  CTC  CCT  GCT  CAG  CTC  CTC  GGC  TG   CTA  TTG  CTC
                   9              18             27             36

C    V    P    G    S    S    G    E    V    V    M    T    Q    S    P
         TGC  GTC  CCC  GGG  TCC  AGT  GGG  GAA  GTT  GTG  ATG  ACT  CAG  TCT  CCA
                   45             54             63             72             81

L    S    L    P    I    T    P    G    E    P    A    S    I    S    C
         CTG  TCC  CTT  CCC  ATC  ACA  CCT  GGA  GAG  CCG  GCC  TCC  ATC  TCC  TGT
                   90             99             108            117            126

R    S    S    Q    S    L    K    H    S    N    G    D    T    F    L
         AGG  TCT  AGT  CAA  AGC  CTT  AAA  CAC  AGT  AAT  GGA  GAC  ACC  TTC  CTG
                   135            144            153            162            171

S    W    Y    Q    Q    K    P    G    Q    P    P    R    L    L    I
         AGT  TGG  TAT  CAG  CAG  AAG  CCA  GGC  CAA  CCT  CCA  AGG  CTC  CTG  ATT
                   180            189            198            207            216

Y    K    V    S    N    R    D    S    G    V    P    D    R    F    S
         TAT  AAG  GTT  TCT  AAC  CGG  GAC  TCT  GGG  GTC  CCA  GAC  AGA  TTC  AGC
                   225            234            243            252            261

G    S    G    A    G    T    D    F    T    L    K    I    S    A    V
         GGC  AGT  GGG  GCA  GGG  ACA  GAT  TTC  ACA  CTG  AAA  ATC  AGC  GCA  GTG
                   270            279            288            297            306

E    A    E    D    V    G    V    Y    F    C    G    Q    G    T    R
         GAG  GCT  GAA  GAT  GTT  GGG  GTT  TAT  TTC  TGC  GGG  CAA  GGT  ACA  AGG
                   315            324            333            342            351

T    P    P    T    F    G    G    G    T    K    V    E    I    K    R
         ACT  CCT  CCC  ACT  TTC  GGC  GGA  GGG  ACC  AAG  GTG  GAA  ATC  AAA  CGT
                   360            369            378            387            396

T    V    A    A    P    S    V    F    I    F    P    P    S    D    E
         ACG  GTG  GCT  GCA  CCA  TCT  GTC  TTC  ATC  TTC  CCG  CCA  TCT  GAT  GAG
                   405            414            423            432            441

Q    L    K    S    G    T    A    S    V    V    C    L    L    N    N
         CAG  TTG  AAA  TCT  GGA  ACT  GCC  TCT  GTT  GTG  TGC  CTG  CTG  AAT  AAC
                   450            459            468            477            486
```

FIG. 9A - 1

```
F   Y   P   R   E   A   K   V   Q   W   K   V   D   N   A
TTC TAT CCC AGA GAG GCC AAA GTA CAG TGG AAG GTG GAT AAC GCC
    495         504         513         522         531

L   Q   S   G   N   S   Q   E   S   V   T   E   Q   D   S
CTC CAA TCG GGT AAC TCC CAG GAG AGT GTC ACA GAG CAG GAC AGC
    540         549         558         567         576

K   D   S   T   Y   S   L   S   S   T   L   T   L   S   K
AAG GAC AGC ACC TAC AGC CTC AGC AGC ACC CTG ACG CTG AGC AAA
    585         594         603         612         621

A   D   Y   E   K   H   K   V   Y   A   C   E   V   T   H
GCA GAC TAC GAG AAA CAC AAA GTC TAC GCC TGC GAA GTC ACC CAT
    630         639         648         657         666

Q   G   L   S   S   P   V   T   K   S   F   N   R   G   E
CAG GGC CTG AGC TCG CCC GTC ACA AAG AGC TTC AAC AGG GGA GAG
    675         684         693         702         711

C   .
TGT TGA
    720
```

FIG. 9A - 2

LENGTH OF 7B6 HEAVY/PRIMATIZED: 1437 bp; LISTED FROM: 1 TO: 1437
TRANSLATED FROM: 1 TO: 1435 (ENTIRE REGION);
GENETIC CODE USED: UNIVERSAL; FRI, MAY 26, 1995 11:09 AM

```
FRAME 1  M   G   W   S   L   I   L   L   F   L   V   A   V
         ATG GGT TGG AGC CTC ATC TTG CTC TTC CTT GTC GCT GTT
             9           18          27          36

A   T   R   V   Q   C   E   V   Q   L   V   E   S   G   G
         GCT ACG CGT GTC CAG TGT GAG GTG CAA CTG GTG GAG TCT GGG GGA
             45          54          63          72          81

G   L   V   Q   P   G   G   S   L   R   V   S   C   A   V
         GGC TTG GTC CAG CCT GGC GGG TCC CTG AGA GTC TCC TGT GCA GTC
             90          99          108         117         126

S   G   F   T   F   S   D   H   Y   M   Y   W   F   R   Q
         TCT GGA TTC ACC TTC AGT GAC CAC TAC ATG TAT TGG TTC CGC CAG
             135         144         153         162         171

A   P   G   K   G   P   E   W   V   G   F   I   R   N   K
         GCT CCA GGG AAG GGG CCG GAA TGG GTA GGT TTC ATT AGA AAC AAA
             180         189         198         207         216

P   N   G   G   T   T   E   Y   A   A   S   V   K   D   R
         CCG AAC GGT GGG ACA ACA GAA TAC GCC GCG TCT GTG AAA GAC AGA
             225         234         243         252         261

F   T   I   S   R   D   D   S   K   S   I   A   Y   L   Q
         TTC ACC ATC TCC AGA GAT GAT TCC AAA AGC ATC GCC TAT CTG CAA
             270         279         288         297         306

M   S   S   L   K   I   E   D   T   A   V   Y   Y   C   T
         ATG AGC AGC CTG AAA ATC GAG GAC ACG GCC GTC TAT TAC TGT ACT
             315         324         333         342         351

T   S   Y   I   S   H   C   R   G   G   V   C   Y   G   G
         ACA TCC TAC ATT TCA CAT TGT CGG GGT GGT GTC TGC TAT GGA GGT
             360         369         378         387         396

Y   F   E   F   W   G   Q   G   A   L   V   T   V   S   S
         TAC TTC GAA TTC TGG GGC CAG GGC GCC CTG GTC ACC GTC TCC TCA
             405         414         423         432         441

A   S   T   K   G   P   S   V   F   P   L   A   P   S   S
         GCT AGC ACC AAG GGC CCA TCG GTC TTC CCC CTG GCA CCC TCC TCC
             450         459         468         477         486
```

FIG. 9B - 1

```
K   S   T   S   G   G   T   A   A   L   G   C   L   V   K
AAG AGC ACC TCT GGG GGC ACA GCG GCC CTG GGC TGC CTG GTC AAG
    495     504     513     522     531

D   Y   F   P   E   P   V   T   V   S   W   N   S   G   A
GAC TAC TTC CCC GAA CCG GTG ACG GTG TCG TGG AAC TCA GGC GCC
    540     549     558     567     576

L   T   S   G   V   H   T   F   P   A   V   L   Q   S   S
CTG ACC AGC GGC GTG CAC ACC TTC CCG GCT GTC CTA CAG TCC TCA
    585     594     603     612     621

G   L   Y   S   L   S   S   V   V   T   V   P   S   S   S
GGA CTC TAC TCC CTC AGC AGC GTG GTG ACC GTG CCC TCC AGC AGC
    630     639     648     657     666

L   G   T   Q   T   Y   I   C   N   V   N   H   K   P   S
TTG GGC ACC CAG ACC TAC ATC TGC AAC GTG AAT CAC AAG CCC AGC
    675     684     693     702     711

N   T   K   V   D   K   K   A   E   P   K   S   C   D   K
AAC ACC AAG GTG GAC AAG AAA GCA GAG CCC AAA TCT TGT GAC AAA
    720     729     738     747     756

T   H   T   C   P   P   C   P   A   P   E   L   L   G   G
ACT CAC ACA TGC CCA CCG TGC CCA GCA CCT GAA CTC CTG GGG GGA
    765     774     783     792     801

P   S   V   F   L   F   P   P   K   P   K   D   T   L   M
CCG TCA GTC TTC CTC TTC CCC CCA AAA CCC AAG GAC ACC CTC ATG
    810     819     828     837     846

I   S   R   T   P   E   V   T   C   V   V   V   D   V   S
ATC TCC CGG ACC CCT GAG GTC ACA TGC GTG GTG GTG GAC GTG AGC
    855     864     873     882     891

H   E   D   P   E   V   K   F   N   W   Y   V   D   G   V
CAC GAA GAC CCT GAG GTC AAG TTC AAC TGG TAC GTG GAC GGC GTG
    900     909     918     927     936

E   V   H   N   A   K   T   K   P   R   E   E   Q   Y   N
GAG GTG CAT AAT GCC AAG ACA AAG CCG CGG GAG GAG CAG TAC AAC
    945     954     963     972     981

S   T   Y   R   V   V   S   V   L   T   V   L   H   Q   D
AGC ACG TAC CGT GTG GTC AGC GTC CTC ACC GTC CTG CAC CAG GAC
    990     999     1008    1017    1026
```

FIG. 9B - 2

```
W   L   N   G   K   E   Y   K   C   K   V   S   N   K   A
TGG CTG AAT GGC AAG GAG TAC AAG TGC AAG GTC TCC AAC AAA GCC
    1035        1044        1053        1062        1071

L   P   A   P   I   E   K   T   I   S   K   A   K   G   Q
CTC CCA GCC CCC ATC GAG AAA ACC ATC TCC AAA GCC AAA GGG CAG
    1080        1089        1098        1107        1116

P   R   E   P   Q   V   Y   T   L   P   P   S   R   D   E
CCC CGA GAA CCA CAG GTG TAC ACC CTG CCC CCA TCC CGG GAT GAG
    1125        1134        1143        1152        1161

L   T   K   N   Q   V   S   L   T   C   L   V   K   G   F
CTG ACC AAG AAC CAG GTC AGC CTG ACC TGC CTG GTC AAA GGC TTC
    1170        1179        1188        1197        1206

Y   P   S   D   I   A   V   E   W   E   S   N   G   Q   P
TAT CCC AGC GAC ATC GCC GTG GAG TGG GAG AGC AAT GGG CAG CCG
    1215        1224        1233        1242        1251

E   N   N   Y   K   T   T   P   P   V   L   D   S   D   G
GAG AAC AAC TAC AAG ACC ACG CCT CCC GTG CTG GAC TCC GAC GGC
    1260        1269        1278        1287        1296

S   F   F   L   Y   S   K   L   T   V   D   K   S   R   W
TCC TTC TTC CTC TAC AGC AAG CTC ACC GTG GAC AAG AGC AGG TGG
    1305        1314        1323        1332        1341

Q   Q   G   N   V   F   S   C   S   V   M   H   E   A   L
CAG CAG GGG AAC GTC TTC TCA TGC TCC GTG ATG CAT GAG GCT CTG
    1350        1359        1368        1377        1386

H   N   H   Y   T   Q   K   S   L   S   L   S   P   G   K
CAC AAC CAC TAC ACG CAG AAG AGC CTC TCC CTG TCT CCG GGT AAA
    1395        1404        1413        1422        1431

TGA
```

FIG. 9B - 3

LENGTH OF 16C10 LAMBDA/PRIMATIZED: 711 bp; LISTED FROM: 1 TO: 711;
TRANSLATED FROM: 1 TO: 709 (ENTIRE REGION);
GENETIC CODE USED: UNIVERSAL; FRI, MAY 26, 1995 11:08 AM

```
FRAME 1  M    R    V    P    A    Q    L    L    G    L    L    L    L
         ATG  AGG  GTC  CCC  GCT  CAG  CTC  CTG  GGCTC     CTG  CTG  CTC
                   9         18             27             36

W    L    P    G    A    R    C    E    S    V    L    T    Q    P    P
         TGG  CTC  CCA  GGT  GCA  CGA  TGT  GAG  TCT  GTC  CTG  ACA  CAG  CCG  CCC
                   45             54             63             72             81

S    V    S    G    A    P    G    Q    K    V    T    I    S    C    T
         TCA  GTG  TCT  GGGGCC    CCA  GGGCAG    AAG  GTC  ACC  ATC  TCG  TGC  ACT
              90             99             108            117            126

G    S    T    S    N    I    G    G    Y    D    L    H    W    Y    Q
         GGGAGC    ACC  TCC  AAC  ATT  GGA  GGT  TAT  GAT  CTA  CAT  TGG  TAC  CAG
                   135            144            153            162            171

Q    L    P    G    T    A    P    K    L    L    I    Y    D    I    N
         CAG  CTC  CCA  GGA  ACG  GCC  CCC  AAA  CTC  CTC  ATC  TAT  GAC  ATT  AAC
                   180            189            198            207            216

K    R    P    S    G    I    S    D    R    F    S    G    S    K    S
         AAG  CGA  CCC  TCA  GGAATT    TCT  GAC  CGA  TTC  TCT  GGCTCC    AAG  TCT
                   225            234            243            252            261

G    T    A    A    S    L    A    I    T    G    L    Q    T    E    D
         GGT  ACC  GCGGCC    TCC  CTG  GCC  ATC  ACT  GGGCTC    CAG  ACT  GAG  GAT
                   270            279            288            297            306

E    A    D    Y    Y    C    Q    S    Y    D    S    S    L    N    A
         GAG  GCT  GAT  TAT  TAC  TGC  CAG  TCC  TAT  GAC  AGC  AGC  CTG  AAT  GCT
                   315            324            333            342            351

Q    V    F    G    G    G    T    R    L    T    V    L    G    Q    P
         CAG  GTA  TTC  GGA  GGA  GGGACC    CGG  CTG  ACC  GTC  CTA  GGT  CAG  CCC
                   360            369            378            387            396

K    A    A    P    S    V    T    L    F    P    P    S    S    E    E
         AAG  GCT  GCC  CCC  TCG  GTC  ACT  CTG  TTC  CCG  CCC  TCC  TCT  GAG  GAG
                   405            414            423            432            441

L    Q    A    N    K    A    T    L    V    C    L    I    S    D    F
         CTT  CAA  GCC  AAC  AAG  GCC  ACA  CTG  GTG  TGT  CTC  ATA  AGT  GAC  TTC
                   450            459            468            477            486
```

FIG. 10A - 1

```
Y   P   G   A   V   T   V   A   W   K   A   D   S   S   P
TAC CCG GGA GCC GTG ACA GTG GCC TGG AAG GCA GAT AGC AGC CCC
    495         504         513         522         531

V   K   A   G   V   E   T   T   T   P   S   K   Q   S   N
GTC AAG GCG GGA GTG GAG ACC ACC ACA CCC TCC AAA CAA AGC AAC
    540         549         558         567         576

N   K   Y   A   A   S   S   Y   L   S   L   T   P   E   Q
AAC AAG TAC GCG GCC AGC AGC TAC CTG AGC CTG ACG CCT GAG CAG
    585         594         603         612         621

W   K   S   H   R   S   Y   S   C   Q   V   T   H   E   G
TGG AAG TCC CAC AGA AGC TAC AGC TGC CAG GTC ACG CAT GAA GGG
    630         639         648         657         666

S   T   V   E   K   T   V   A   P   T   E   C   S   .
AGC ACC GTG GAG AAG ACA GTG GCC CCT ACA GAA TGT TCA TGA
    675         684         693         702         711
```

FIG. 10A - 2

LENGTH OF 16C10 HEAVY/PRIMATIZED: 1431 bp; LISTED FROM: 1 TO: 1431;
TRANSLATED FROM: 1 TO: 1429 (ENTIRE REGION);
GENETIC CODE USED: UNIVERSAL; FRI, MAY 26, 1995 11:08 AM

```
FRAME 1  M    K    H    L    W    F    F    L    L    L    V    A    A
         ATG  AAA  CAC  CTG  TGG  TTC  TTC  CTC  CTC  CTG  GTG  GCA  GCT
                   9              18             27             36

P    R    W    V    L    S    Q    V    Q    L    Q    E    S    G    P
         CCC  AGA  TGG  GTC  CTG  TCC  CAG  GTG  CAG  CTG  CAG  GAG  TCG  GGC  CCA
              45             54             63             72             81

G    L    V    K    P    S    E    T    L    S    L    T    C    A    V
         GGA  CTG  GTG  AAG  CCT  TCG  GAG  ACC  CTG  TCC  CTC  ACC  TGC  GCT  GTC
              90             99             108            117            126

S    G    G    S    I    S    G    G    Y    G    W    G    W    I    R
         TCT  GGT  GGC  TCC  ATC  AGC  GGT  GGT  TAT  GGC  TGG  GGC  TGG  ATC  CGC
              135            144            153            162            171

Q    P    P    G    K    G    L    E    W    I    G    S    F    Y    S
         CAG  CCC  CCA  GGG  AAG  GGG  CTG  GAG  TGG  ATT  GGG  AGT  TTC  TAT  AGT
              180            189            198            207            216

S    S    G    N    T    Y    Y    N    P    S    L    K    S    Q    V
         AGT  AGT  GGG  AAC  ACC  TAC  TAC  AAC  CCC  TCC  CTC  AAG  AGT  CAA  GTC
              225            234            243            252            261

T    I    S    T    D    T    S    K    N    Q    F    S    L    K    L
         ACC  ATT  TCA  ACA  GAC  ACG  TCC  AAG  AAC  CAG  TTC  TCC  CTG  AAG  CTG
              270            279            288            297            306

N    S    M    T    A    A    D    T    A    V    Y    Y    C    V    R
         AAC  TCT  ATG  ACC  GCC  GCG  GAC  ACG  GCC  GTG  TAT  TAC  TGT  GTG  AGA
              315            324            333            342            351

D    R    L    F    S    V    V    G    M    V    Y    N    N    W    F
         GAT  CGT  CTT  TTT  TCA  GTT  GTT  GGA  ATG  GTT  TAC  AAC  AAC  TGG  TTC
              360            369            378            387            396

D    V    W    G    P    G    V    L    V    T    V    S    S    A    S
         GAT  GTC  TGG  GGC  CCG  GGA  GTC  CTG  GTC  ACC  GTC  TCC  TCA  GCT  AGC
              405            414            423            432            441

T    K    G    P    S    V    F    P    L    A    P    S    S    K    S
         ACC  AAG  GGC  CCA  TCG  GTC  TTC  CCC  CTG  GCA  CCC  TCC  TCC  AAG  AGC
              450            459            468            477            486
```

FIG. 10B - 1

```
  T   S   G   G   T   A   A   L   G   C   L   V   K   D   Y
ACC TCT GGG GGC ACA GCG GCC CTG GGC TGC CTG GTC AAG GAC TAC
    495     504         513         522         531

F   P   E   P   V   T   V   S   W   N   S   G   A   L   T
TTC CCC GAA CCG GTG ACG GTG TCG TGG AAC TCA GGC GCC CTG ACC
    540     549         558         567         576

S   G   V   H   T   F   P   A   V   L   Q   S   S   G   L
AGC GGC GTG CAC ACC TTC CCG GCT GTC CTA GAC TCC TCA GGA CTC
    585     594         603         612         621

Y   S   L   S   S   V   V   T   V   P   S   S   S   L   G
TAC TCC CTC AGC AGC GTG GTG ACC GTG CCC TCC AGC AGC TTG GGC
    630     639         648         657         666

T   Q   T   Y   I   C   N   V   N   H   K   P   S   N   T
ACC CAG ACC TAC ATC TGC AAC GTG AAT CAC ACA TGC CCA AAC ACC
    675     684         693         702         711

K   V   D   K   K   A   E   P   K   S   C   D   K   T   H
AAG GTG GAC AAG AAA GCA GAG CCC AAA TCT TGT GAC AAA ACT CAC
    720     729         738         747         756

T   C   P   P   C   P   A   P   E   L   L   G   G   P   S
ACA TGC CCA CCG TGC CCA GCA CCT GAA CTC CTG GGG GGA CCG TCA
    765     774         783         792         801

V   F   L   F   P   P   K   P   K   D   T   L   M   I   S
GTC TTC CTC TTC CCC CCA AAA CCC AAG GAC ACC CTC ATG ATC TCC
    810     819         828         837         846

R   T   P   E   V   T   C   V   V   V   D   V   S   H   E
CGG ACC CCT GAG GTC ACA TGC GTG GTG GTG GAC GTG AGC CAC GAA
    855     864         873         882         891

D   P   E   V   K   F   N   W   Y   V   D   G   V   E   V
GAC CCT GAG GTC AAG TTC AAC TGG TAC GTG GAC GGC GTG GAG GTG
    900     909         918         927         936

H   N   A   K   T   K   P   R   E   E   Q   Y   N   S   T
CAT AAT GCC AAG ACA AAG CCG CGG GAG GAG CAG TAC AAC AGC ACG
    945     954         963         972         981

Y   R   V   V   S   V   L   T   V   L   H   Q   D   W   L
TAC CGT GTG GTC AGC GTC CTC ACC GTC CTG CAC CAG GAC TGG CTG
    990     999        1008        1017        1026
```

FIG. 10B - 2

```
  N    G   E   Y   K   C   K   V   S   N   K   A   L   P
AAT GGC AAG GAG TAC AAG TGC AAG GTC TCC AAC AAA GCC CTC CCA
    1035        1044        1053        1062        1071

A   P   I   E   K   T   I   S   K   A   K   G   Q   P   R
GCC CCC ATC GAG AAA ACC ATC TCC AAA GCC AAA GCC AAA CCC CGA
    1080        1089        1098        1107        1116

E   P   Q   V   Y   T   L   P   P   S   R   D   E   L   T
GAA CCA CAG GTG TAC ACC CTG CCC CCA TCC CGG GAT GAG CTG ACC
    1125        1134        1143        1152        1161

K   N   Q   V   S   L   T   C   L   V   K   G   F   Y   P
AAG AAC CAG GTC AGC CTG ACC TGC CTG GTC AAA GGC TTC TAT CCC
    1170        1179        1188        1197        1206

S   D   I   A   V   E   W   E   S   N   G   Q   P   E   N
AGC GAC ATC GCC GTG GAG TGG GAG AGC AAT GGG CAG CCG GAG AAC
    1215        1224        1233        1242        1251

N   Y   K   T   T   P   P   V   L   D   S   D   G   S   F
AAC TAC AAG ACC ACG CCT CCC GTG CTG GAC TCC GAC GGC TCC TTC
    1260        1269        1278        1287        1296

F   L   Y   S   K   L   T   V   D   K   S   R   W   Q   Q
TTC CTC TAC AGC AAG CTC ACC GTG GAC AAG AGC AGG TGG CAG CAG
    1305        1314        1323        1332        1341

G   N   V   F   S   C   S   V   M   H   E   A   L   H   N
GGG AAC GTC TTC TCA TGC TCC GTG ATG CAT GAG GCT CTG CAC AAC
    1350        1359        1368        1377        1386

H   Y   T   Q   K   S   L   S   L   S   P   G   K   .
CAC TAC ACG CAG AAG AGC CTC TCC CTG TCT CCG GGT AAA TGA
    1395        1404        1413        1422        1431
```

FIG. 10B - 3

METHODS FOR TREATING B CELL LYMPHOMA USING CD80-SPECIFIC ANTIBODIES

RELATED APPLICATIONS

This is a divisional application of application Ser. No. 09/383,916, flied Aug. 26, 1999, now U.S. Pat. No. 6,709,654 B1, which is a divisional application of application Ser. No. 08/487,550, filed Jun. 7, 1995, which issued as U.S. Pat. No. 6,113,898.

FIELD OF THE INVENTION

The present invention relates to the manufacture and identification of novel monoclonal antibodies to human B7, i.e., human B7.1 and human B7.2 and primatized forms thereof. More specifically, the present invention relates to the production and identification of macaque antibodies to human B7, i.e., human B7.1 and human B7.2 produced by screening of phage display libraries and monkey heterohybridomas using B lymphocytes obtained from B7 immunized monkeys.

The invention further relates to specific primatized antibodies which bind to human B7, i.e., human B7.1 and B7.2 as well as their corresponding amino acid and nucleic acid sequences.

Also, the present invention relates to pharmaceutical compositions containing monkey monoclonal or primatized antibodies specific to human B7.1 and/or human B7.2 and their use as immunosuppressants by modulating the B7:CD28 pathway, e.g., for the treatment of autoimmune disorders, and the prevention of organ rejection.

BACKGROUND OF THE INVENTION

The clinical interface between immunology, hematology, and oncology has long been appreciated. Many conditions treated by the hematologist or oncologist have either an autoimmune or immunodeficient component to their pathophysiology that has led to the widespread adoption of immunosuppressive medications by hematologists, whereas oncologists have sought immunologic adjuvants that might enhance endogenous immunity to tumors. To date, these interventions have generally consisted of nonspecific modes of immunosuppression and immune stimulation. In addition to the limited efficacy of these interventions, toxicities secondary to their nonspecificity have also limited their overall success. Therefore, alternative strategies have been sought.

Elucidation of the functional role of a rapidly increasing number of cell surface molecules has contributed greatly to the integration of immunology with clinical hematology and oncology. Nearly 200 cell surface antigens have been identified on cells of the immune and hematopoietic systems (Schlossman S F. Boumsell L. Gilks J M, Harlan T. Kishimoto, C. Morimoto C, Ritz J. Shaw S, Silverstein R L, Springer T A, Tedder T F, Todd RF:CD antigens (1993), *Blood* 83:879, 1994). These antigens represent both lineage-restricted and more widely distributed molecules involved in a variety of processes, including cellular recognition, adhesion, induction and maintenance of proliferation, cytokine secretion, effector function, and even cell death. Recognition of the functional attributes of these molecules has fostered novel attempts to manipulate the immune response. Although molecules involved in cellular adhesion and antigen-specific recognition have previously been evaluated as targets of therapeutic immunologic intervention, recent attention has focused on a subgroup of cell surface molecules termed co-stimulatory molecules (Bretscher P: "The two-signal model of lymphocyte activation twenty-one years later." *Immunol. Today* 13:73, (1992); Jenkins M K, Johnson J G: "Molecules involved in T-cell co-stimulation." *Curr Opin Immunol* 5:351, 1993; Geppert T, Davis L. Gur H. Wacholtz M. Lipsky P: "Accessory cell signals involved in T-cell activation." *Immunol Rev* 117:5, (1990); Weaver C T, Unanue E R: "The co-stimulatory function of antigen-presenting cells." *Immunol Today* 11:49, (1990); Stennam R M, Young J W: "Signals arising from antigen-presenting cells." *Curr Opin Immunol* 3:361, (1991)). Co-stimulatory molecules do not initiate but rather enable the generation and amplification of antigen-specific T-cell responses and effector function (Bretscher P: "The two-signal model of lymphocyte activation twenty-one years later." *Immunol. Today* 13:73, (1992); Jenkins M K, Johnson J G: "Molecules involved in T-cell co-stimulation." *Curr Opin Immunol* 5:351, (1993); Geppert T, Davis L. Gur H. Wacholtz M. Lipsky P: "Accessory cell signals involved in T-cell activation." *Immunol Rev* 117:5, (1990); Weaver C T, Unanue E R: "The co-stimulatory function of antigen-presenting cells." *Immunol Today* 11:49, (1990); Stennam R M, Young J W: "Signals arising from antigen-presenting cells." *Curr Opin Immunol* 3:361, (1991); June C H, Bluestone J A, Linsley P S, Thompson C D: "Role of the CD28 receptor in T-cell activation." *Immunol Today* 15:321, (1994).

Recently, one specific co-stimulatory pathway termed B7:CD28 has been studied by different research groups because of its significant role in B and T cell activation (June C H, Bluestone J A, Linsley P S, Thompson C D: "Role of the CD28 receptor in T-cell activation." *Immunol Today* 15:321, (1994); June C H, Ledbetter J A: "The role of the CD28 receptor during T-cell responses to antigen." *Annu Rev Immunol* 11:191, (1993); Schwartz R H: "Co-stimulation of T lymphocytes: The role of CD28, CTLA-4, and B7/BB1 in interleukin-2 production and immunotherapy." *Cell* 71:1065, (1992)). Since this ligand:receptor pathway was discovered four years ago, a large body of evidence has accumulated suggesting that B7:CD28 interactions represent one of the critical junctures in determining immune reactivity versus anergy (June C H, Bluestone J A, Linsley P S, Thompson C D: "Role of the CD28 receptor in T-cell activation." *Immunol Today* 15:321, (1994); June C H, Ledbetter J A: "The role of the CD28 receptor during T-cell responses to antigen." *Annu Rev Immunol* 11:191, (1993); Schwartz R H: "Co-stimulation of T lymphocytes: The role of CD28, CTLA-4, and B7/BB1 in interleukin-2 production and immunotherapy." *Cell* 71:1065, (1992); Cohen J: "Mounting a targeted strike on unwanted immune responses" (news; comment). *Science* 257:751, (1992); Cohen J: "New protein steals the show as 'co-stimulator' of T cells" (news; comment). *Science* 262:844, (1993)).

In particular, the role of the human B7 antigens, i.e., human B7.1 and B7.2, has been reported to play a co-stimulatory role in T-cell activation.

1. B7.1 and B7.2 Co-stimulatory Role in T Cell Activation

The elaboration of a successful immune response depends on a series of specific interactions between a T cell and an antigen presenting cell. Although the essential first step in this process depends upon the binding of antigen to the T cell receptor, in the context of the MHC class II molecule (Lane, P. J. L., F. M. McConnell, G. L. Schieven, E. A. Clark, and J. A. Ledbetter, (1990), "The Role of Class II Molecules in Human B Cell Activation." *The Journal of Immunology*, 144:3684–3692), this interaction alone is not sufficient to induce all the events necessary for a sustained response to a given antigen (Schwartz, R. H. (1990), "A Cell Culture Model for T Lymphocyte Clonal Anergy." *Science*, 248:1349; Jenkins, M. K. (1992). "The Role of Cell Division in the Induction of Clonal Anergy." *Immunology Today*, 13:69; Azuma, M., M. Catabyab, D. Buck, J. H. Phillips, and L. L. Lanier, (1992). "Involvement of CD28 in MHC-unrestricted Cytotoxicity Mediated by a Human Natural Killer Leukemia Cell Line." *The Journal of Immunology*, 149:1556–1561; Azuma, M., M. Catabyab, D. Buck, J. H. Phillips, and L. L. Lanier, (1992). "CD28 Interaction with B7 Costimulates Primary Allogeneic Proliferative Responses and Cytotoxicity Mediated by Small Resting T Lymphocytes." *J. Exp. Med.*, 175:353–360).

The involvement of certain other co-stimulatory molecules is necessary (Norton, S. D., L. Zuckerman, K. B. Urdahl, R. Shefner, J. Miller, and M. K. Jenkins. (1992), "The CD28 Ligand, B7, Enhances IL-2 Production by Providing A Costimulatory Signal to T Cells." The *Journal of Immunology*, 149:1556–1561). "The homodimers CD28 and CTLA-4 expressed on T cells" (June, C. H., J. A. Ledbetter, P. S. Linsley, and C. B. Thompson, (1990), "Role of the CD28 Receptor in T-Cell Activation." *Immunology Today*, 11:211–216; Linsley, P. S., W. Brady, M. Urnes, L. S. Grosmaire, N. K. Damle, and J. A. Ledbetter, (1991), "CTLA-4 is a Second Receptor for the B Cell Activation Antigen B7." *J. Exp. Med.*, 174:561), together with B7.1 (CD80) and B7.2 (CD86) expressed on antigen presenting cells, are major pairs of co-stimulatory molecules necessary for a sustained immune response (Azuma, M., H. Yssel, J. H. Phillips, H. Spits, and L. L. Lanier, (1993), "Functional Expression of B7/BB1 on Activated T Lymphocytes." *J. Exp. Med.*, 177:845–850; Freeman, G. J., A. S. Freedman, J. M. Segil, G. Lee, J. F. Whitman, and L M. Nadler, (1989), "B7, A New Member of the Ig Superfamily with Unique Expression on Activated and Neoplastic B Cells." *The Journal of Immunology*, 143:2714–2722; Hathcock, K. S., G. Laslo, H. B. Dickler, J. Bradshaw, P. Linsley, and R. J. Hodes, (1993), "Identification of an Alternative CTLA-4 Ligand Costimulatory for T Cell Activation." *Science*, 262:905–911; Hart, D. N. J., G. C. Starling, V. L. Calder, and N. S. Fernando, (1993). "B7/BB-1 is a Leucocyte Differentiation Antigen on Human Dendritic Cells Induced by Activation." *Immunology*, 79:616–620). It can be shown in vitro that the absence of these co-stimulatory signals leads to an aborted T cell activation pathway and the development of unresponsiveness to the specific antigen, or anergy. (See, e.g., Harding, F. A., J. G. McArthur, J. A. Gross, D. M. Raulet, and J. P. Allison, (1992). "CD28 Mediated Signalling Co-stimulates Murine T Cells and Prevents Induction of Anergy in T Cell Clones." *Nature*, 356:607–609; Gimmi, C.D., G. J. Freeman, J. G. Gribben, G. Gray, and L. M. Nadler, (1993). "Human T-Cell Clonal Anergy is Induced by Antigen Presentation in the Absence of B7 Costimulation." *Proc. Natl. Acad. Sci.*, 90:6586–6590; Tan, P., C. Anasefti, J. A. Hansen, J. Melrose, M. Brunvand, J. Bradshaw, J. A. Ledbetter, and P. S. Linsley, (1993), "Induction of Alloantigen-specific Hyporesponsiveness in Human T Lymphocytes by Blocking Interaction of CD28 with Its Natural Ligand B7/BB1." *J. Exp. Med.*, 177:165–173). Achievement of in vivo tolerance constitutes a mechanism for immunosuppression and a viable therapy for organ transplant rejection and for the treatment of autoimmune diseases. This has been achieved in experimental models following the administration of CTLA4-Ig (Lenschow, D. J., Y. Zeng, R. J. Thistlethwaite, A. Montag, W. Brady, M. G. Gibson, P. S. Linsley, and J. A. Bluestone, (1992), "Long-Term Survival of Xenogeneic Pancreatic Islet Grafts Induced by CTLA-4Ig." *Science*, 257:789–795).

The molecules B7.1 and B7.2 can bind to either CD28 or CTLA-4, although B7.1 binds to CD28 with a Kd of 200 Nm and to CTLA-4 with a 20-fold higher affinity (Linsley, P. S., E. A. Clark, and J. A. Ledbetter, (1990), "T-Cell Antigen CD28 Mediates Adhesion with B Cells by Interacting with Activation Antigen B7/BB-1." *Proc. Natl. Acad. Sci.*, 87:5031–5035; Linsley et al, (1993), "The Role of the CD28 receptor during T cell responses to antigen," *Annu. Rev. Immunol.*, 11:191–192; Linesley et al, (1993), "CD28 Engagement by B7/BB-1 Induces Transient Down-Regulation of CD28 Synthesis and Prolonged Unresponsiveness to CD28 Signaling," *The Journal of Immunology*, 150:3151–3169). B7.2 is expressed on activated B cells and interferon induced monocytes, but not resting B cells (Freeman, G. J., G. S. Gray, C. D. Gimmi, D. B. Lomarrd, L-J. Zhou, M. White, J. D. Fingeroth, J. G. Gribben, and L M. Nadler, (1991). "Structure, Expression and T Cell Costimulatory Activity of the Murine Homologue of the Human B Lymphocyte Activation Antigen B7," *J. Exp. Med.*, 174:625–631). B7.2, on the other hand, is constitutively expressed at very low levels on resting monocytes, dendritic cells and B cells, and its expression is enhanced on activated T cells, NK cells and B lymphocytes (Azuma, M. D. Ito, H. Yagita, K. Okumura, J. H. Phillips, L. L. Lanier, and C. Somoza, "1993", "IB70 Antigen is a Second Ligand for CTLA-4 and CD28, " *Nature*, 366:76–79). Although B7.1 and B7.2 can be expressed on the same cell type, their expression on B cells occurs with different kinetics (Lenschow, D. J., G. H. Su, L. A. Zuckerman, N. Nabavi, C. L. Jellis, G. S. Gray, J. Miller, and J. A. Bluestone, (1993), "Expression and Functional Significance of an Additional Ligand for CTLA-4," *Proc. Natl. Acad. Sci.*, USA, 90:11054–11058; Boussiotis, V. A., G. J. Freeman, J. G. Gribben, J. Daley, G. Gray, and L. M. Nadler, (1993), "Activated Human B Lymphocytes Express Three CTLA-4 Counter-receptors that Co-stimulate T-Cell Activation," *Proc. Natl. Acad. Sci.*, USA, 90:11059–11063). Further analysis at the RNA level has demonstrated that B7.2 mRNA is constitutively expressed, whereas B7.1 mRNA is detected 4 hours after activation and initial low levels of B7.1 protein are not detectable until 24 hours after stimulation (Boussiotis, V. A., G. J. Freeman, J. G. Gribben, J. Daley, G. Gray, and L. M. Nadler, (1993), "Activated Human B Lymphocytes Express Three CTLA-4 Counter-receptors that Co-stimulate T-Cell Activation," *Proc. Natl. Acad. Sci.*, USA, 90:11059–11063). CTLA-4/CD28 counter receptors, therefore, may be expressed at various times after B Cell activation.

The differential temporal expression of B7.1 and B7.2 suggests that the interaction of these two molecules with CTLA-4 and/or CD28 deliver distinct but related signals to the T cell (LaSalle, J. M., P. J. Tolentino, G. J. Freeman, L. M. Nadler, and D. A. Hafler, (1992), "CD28 and T Cell Antigen Receptor Signal Transduction Coordinately Regulate Intedeukin 2 Gene Expression In Response to Superantigen Stimulation," *J. Exp. Med.*, 176:177–186; Vandenberghe, P., G. J. Freeman, L. M. Nadler, M. C. Fletcher, M. Kamoun, L. A. Turka, J. A. Ledbetter, C. B. Thompson, and C. H. June, (1992), "Antibody and B7/BB1-mediated Ligation of the CD28 Receptor Induces Tyrosine Phosphorylation in Human T Cells," *The Journal of Experimental Medicine*, 175:951–960). The exact signaling functions of CTLA-4 and CD28 on the T cell are currently unknown (Janeway, C. A., Jr. and K. Bottomly, (1994), "Signals and Signs for Lymphocyte Responses," *Cell*, 76.275285). However, it is possible that one set of receptors could provide the initial stimulus for T cell activation and the second, a sustained signal to allow further elaboration of the pathway and clonal expansion to take place (Linsley, P. S., J. L. Greene, P. Tan, J. Bradshaw, J. A. Ledbetter, C. Anasetti, and N. K. Damle, (1992), "Coexpression and Functional Cooperation of CTLA-4 and CD28 on Activated T Lymphocytes," *J. Exp. Med.*, 176:1595–1604). The current data supports the two-signal hypothesis proposed by Jenkins and Schwartz (Schwartz, R. H., (1990), "A Cell Culture Model for T Lymphocyte Clonal Anergy," *Science*, 248:1349; Jenkins, M. K., (1992), "The Role of Cell Division in the Induction of Clonal Anergy," *Immunology Today*, 13:69) that both a TCR and co-stimulatory signal are necessary for T cell expansion, lymphokine secretion and the full development of effector function (Greenan, V. and G. Kroemer, (1993), "Multiple Ways to Cellular Immune Tolerance," *Immunology Today*, 14:573). The failure to deliver the second signal results in the inability of T cells to secrete IL-2 and renders the cell unresponsive to antigen.

Structurally, both B7.1 and B7.2 contain extracellular immunoglobulin superfamily V and C-like domains, a hydrophobic transmembrane region and a cytoplasmic tail (Freeman, G. J., J. G. Gribben, V. A. Boussiotis, J. W. Ng, V. Restivo, Jr., L. A. Lombard, G. S. Gray, and L. M. Nadler, (1993), "Cloning of B7-2: A CTLA-4 Counter-receptor that Co-stimulates Human T Cell Proliferation," *Science*, 262:909). Both B7.1 and B7.2 are heavily glycosylated. B7.1 is a 44–54 kD glycoprotein comprised of a 223 amino acid extracellular domain, a 23 amino acid transmembrane domain, and a 61 amino acid cytoplasmic tail. B7.1 contains 3 potential protein kinase phosphorylation sites. (Azuma, M., H. Yssel, J. H. Phillips, H. Spits, and L. L. Lanier, (1993), "Functional Expression of B7/BB1 on Activated T Lymphocytes," *J. Exp. Med.*, 177:845–850). B7.2 is a 306 amino acid membrane glycoprotein. It consists of a 220 amino acid extracellular region, a 23 amino acid hydrophobic transmembrane domain and a 60 amino acid cytoplasmic tail (Freeman, G. J., A. S. Freedman, J. M. Segil, G. Lee, J. F. Whitman, and L M. Nadler, (1989), "B7, A New Member of the Ig Superfamily with Unique Expression on Activated and Neoplastic B Cells," *The Journal of Immunology*, 143:2714–2722). Although both B7.1 and B7.2 genes are localized in the same chromosomal region (Freeman, G. J., D. B. Lombard, C. D. Gimmi, S. A. Brod, L Lee, J. C. Laning, D. A. Hafler, M. E. Dorf, G. S. Gray, H. Reiser, C. H. June, C. B. Thompson, and L. M. Nadler, (1992), "CTLA-4 and CD28 mRNA are Coexpressed in Most T Cells After Activation," *The Journal of Immunology*, 149:3795–3801; Schwartz, R. H., (1992), "Costimulation of T Lymphocytes: The Role of CD28, CTLA-4, and B7/BB1" in Selvakumar, A., B. K. Mohanraj, R. L. Eddy, T. B. Shows, P. C. White, C. Perrin, and B. Dupont, (1992), "Genomic Organization and Chromosomal Location of the Human Gene Encoding the B-Lymphocyte Activation Antigen B7," *Immunogenetics*, 36:175–181), these antigens do not share a high level of homology. The overall homology between B7.1 and B7.2 is 26% and between murine B7.1 and human S7 is 27% (Azuma, M., H. Yssel, J. H. Phillips, H. Spits, and L. L. Lanier, (1993), "Functional Expression of B7/BB1 on Activated T Lymphocytes," *J. Exp. Med.*, 177:845–850; Freeman, G. J., A. S. Freedman, J. M. Segil, G. Lee, J. F. Whitman, and L M. Nadler, (1989), "B7, A New Member of the Ig Superfamily with Unique Expression on Activated and Neoplastic B Cells," *The Journal of Immunology*, 143:2714–2722). Although alignment of human B7.1 human B7.2 and murine B.1 sequences shows few stretches of lengthy homology, it is known that all three molecules bind to human CTLA-4 and CD28. Thus, there is most likely a common, or closely homologous region shared by the three molecules that may be either contiguous or conformational. This region may constitute the binding site of the B7.1 and B7.2 molecules to their counter-receptors. Antibodies raised against these epitopes could potentially inhibit the interaction of B7 with its counter-receptor on the T cell. Furthermore, antibodies that cross-reacted with this region on both B7.1 and 37.2 molecules would potentially have practical advantages over antibodies directed against B7.1 or B7.2 separately.

2. Blockade of the B7/CD28 Interaction

Blocking of the B7/CD28 interaction offers the possibility of inducing specific immunosuppression, with potential for generating long lasting antigen-specific therapeutic effects. Antibodies to either B7.1 or B7.2 have been shown to block T cell activation, as measured by the inhibition of IL-2 production in vitro (DeBoer, M., P. Parren, J. Dove, F. Ossendorp, G. van der Horst, and J. Reeder, (1992), "Functional Characterization of a Novel Anti-B7 Monoclonal Antibody," *Eur. Journal of Immunology*, 22:3071–3075; Azuma, M., H. Yssel, J. H. Phillips, H. Spits, and L. L. Lanier, (1993), "Functional Expression of B7/BB1 on Activated T Lymphocytes," *J. Exp. Med.*, 177:845–850). However, different antibodies have been shown to vary in their immunosuppressive potency, which may reflect either their affinity or epitope specificity. CTLA-4/lg fusion protein and anti-CD28 Fabs were shown to have similar effects on the down regulation of IL-2 production.

In vivo administration of a soluble CTLA-4/lg fusion protein has been shown to suppress T cell—dependent antibody responses in mice (Linsley, P. S., J. L. Greene, P. Tan, J. Bradshaw, J. A. Ledbetter, C. Anasetti, and N. K. Damle, (1992), "Coexpression and Functional Cooperation of CTLA-4 and CD28 on Activated T Lymphocytes," *J. Exp. Med.*, 176:1595–1604; Lin, H., S. F. Builing, P. S. Linsley, R. O. Wei, C. D. Thompson, and L. A. Turka, (1993), "Long-term Acceptance of Major Histocompatibility Complex Mismatched Cardiac Allografts Induced by CTLA-4-Ig Plus Donor Specific Transfusion," *J. Exp. Med.*, 178:1801) and, furthermore, larger doses were also able to suppress responses to a second immunization, demonstrating the feasibility of this approach for the treatment of antibody mediated autoimmune disease. In addition, CTLA-4/Ig was able to prevent pancreatic islet cell rejection in mice by directly inhibiting the interaction of T cells and B7.1/B7.2 antigen presenting cells (Lenschow, D. J., G. H. Su, L. A. Zuckerman, N. Nabavi, C. L. Jellis, G. S. Gray, J. Miller, and J. A. Bluestone, (1993), "Expression and Functional Significance of an Additional Ligand for CTLA-4," *Proc. Natl. Acad. Sci.*, USA, 90:11054–11058). In this case, long term donor specific tolerance was achieved.

3. Recombinant Phage Display Technology for Antibody Selection

To date, no monoclonal antibodies which cross-react with both B7.1 and B7.2 have been reported. As noted, such antibodies would potentially be highly desirable as immunosuppressants. Phage display technology is beginning to replace traditional methods for isolating antibodies generated during the immune response, because a much greater percentage of the immune repertoire can be assessed than is possible using traditional methods. This is in part due to PEG fusion inefficiency, chromosomal instability, and the large amount of tissue culture and screening associated with heterohybridoma production. Phage display technology, by contrast, relies on molecular techniques for potentially capturing the entire repertoire of immunoglobulin genes associated with the response to a given antigen.

This technique is described by Barber et al, *Proc. Natl. Acad. Sci., USA*, 88, 7978–7982, (1991). Essentially, immunoglobulin heavy chain genes are PCR amplified and cloned into a vector containing the gene encoding the minor coat protein of the filamentous phage M13 in such a way that a heavy chain fusion protein is created. The heavy chain fusion protein is incorporated into the M13 phage particle together with the light chain genes as it assembles. Each recombinant phage contains, within its genome, the genes for a different antibody Fab molecule which it displays on its surface. Within these libraries, in excess of $10^6$ different antibodies can be cloned and displayed. The phage library is panned on antigen coated microliter wells, non-specific phage are washed off, and antigen binding phage are eluted. The genome from the antigen-specific clones is isolated and the gene III is excised, so that antibody can be expressed in soluble Fab form for further characterization. Once a single Fab is selected as a potential therapeutic candidate, it may easily be converted to a whole antibody. A previously described expression system for converting Fab sequences to whole antibodies is IDEC's mammalian expression vector NEOSPLA. This vector contains either human gamma 1 or gamma 4 constant region genes. CHO cells are transfected with the NEOSPLA vectors and after amplification this vector system has been reported to provide very high expression levels (>30 pg/cell/day) can be achieved.

4. Primatized Antibodies

Another highly efficient means for generating recombinant antibodies is disclosed by Newman, (1992), *Biotechnology*, 10, 1455–1460. More particularly, this technique results in the generation of primatized antibodies which contain monkey variable domains and human constant sequences. This reference is incorporated by reference in its entirety herein. Moreover, this technique is also described in commonly assigned U.S. application Ser. No. 08/379,072, filed on Jan. 25, 1995, which is a continuation of U.S. Ser. No. 07/912,292, filed Jul. 10, 1992, which is a continuation-in-part of U.S. Ser. No. 07/856,281, filed Mar. 23, 1992, which is finally a continuation-in-part of U.S. Ser. No. 07/735,064, filed Jul. 25, 1991. Ser. No. 08/379,072 and the parent application thereof are incorporated by reference in their entirety herein.

This technique modifies antibodies such that they are not antigenically rejected upon administration in humans. This technique relies on immunization of cynomolgus monkeys with human antigens or receptors. This technique was developed to create high affinity monoclonal antibodies directed to human cell surface antigens.

Antibodies generated in this manner have previously been reported to display human effector function, have reduced immunogenicity, and long serum half-life. The technology relies on the fact that despite the fact that cynomolgus monkeys are phylogenetically similar to humans, they still recognize many human proteins as foreign and therefore mount an immune response. Moreover, because the cynomolgus monkeys are phylogenetically close to humans, the antibodies generated in these monkeys have been discovered to have a high degree of amino acid homology to those produced in humans. Indeed, after sequencing macaque immunoglobulin light and heavy chain variable region genes, it was found that the sequence of each gene family was 85–98% homologous to its human counterpart (Newman et al, (1992), Id.). The first antibody generated in this way, an anti-CD4 antibody, was 91–92% homologous to the consensus sequence of human immunoglobulin framework regions. Newman et al, Biotechnology, 10:1458–1460, (1992).

Monoclonal antibodies specific to the human B7 antigen have been previously described in the literature. For example, Weyl et al, *Hum. Immunol.*, 31(4), 271–276, (1991) describe epitope mapping of human monoclonal antibodies against HLA-B-27 using natural and mutated antigenic variants. Also, Toubert et al, *Clin. Exp. Immunol.*, 82(1), 16–20, (1990) describe epitope mapping of an HLA-B27 monoclonal antibody that also reacts with a 35-KD bacterial outer membrane protein. Also, Valle et al, *Immunol.*, 69(4), 531–535, (1990) describe a monoclonal antibody of the IgG1 subclass which recognizes the B7 antigen expressed in activated B cells and HTLV-1-transformed T cells. Further, Toubert et al, *J. Immunol.*, 141(7), 2503-9, (1988) describe epitope mapping of HLA-B27 and HLA-B7 antigens using intradomain recombinants constructed by making hybrid genes between these two alleles in *E. coli*.

High expression of B7 antigen has been correlated to autoimmune diseases by some researchers. For example, Ionesco-Tirgoviste et al, *Med. Interre*, 24(1), 11–17, (1986) report increased B7 antigen expression in type 1 insulin-dependent diabetes. Also, the involvement of B7 antigen expression on dermal dendritic cells obtained from psoriasis patients has been reported. (Nestle et al, *J. Clin. Invest.*, 94(1), 202–209, (1994)).

Further, the inhibition of anti-HLA-B7 alloreactive CTL using affinity-purified soluble HLA-B7 has been reported in the literature. (Zavazava et al, *Transplantation*, 51(4), 838–42, (1991)). Further, the use of B7 receptor soluble ligand, CTLA-4-Ig to block B7 activity (See, e.g., Lenschow et al, *Science*, 257, 789, 7955 (1992)) in animal models and a B7-1-Ig fusion protein capable of inhibiting B7 has been reported.

SUMMARY AND OBJECTS OF THE INVENTION

An object of the invention is to produce and identify novel macaque antibodies to human B7 antigen, more specifically to human B7.1 antigen and/or human B7.2 antigen.

More specifically, it is an object of the present invention to produce and identify novel macaque antibodies to human B7 antigen, i.e., human B7.1 and human B7.2 antigen by screening of phage display libraries and/or monkey heterohybridomas using B lymphocytes obtained from human B7 antigen, i.e., human B7.1 or B7.2 antigen immunized monkeys.

It is another specific object of the invention to provide anti-B7 monkey monoclonal antibodies and primatized forms thereof which specifically bind human B7.1 and/or B7.2 antigen which inhibit the B7/CD86 pathway and B7 stimulation of activated T cells, thereby inhibiting IL-2 production and T cell proliferation and functioning as effective immunosuppressants.

It is another object of the invention to provide anti-human B7.1 and anti-human B7.2 monkey monoclonal antibodies and primatized forms thereof which inhibit antigen driven responses in donor spleen cell cultures, e.g., antigen specific IgG responses, IL-2 production and cell proliferation.

It is another specific object of the invention to identify particular monkey monoclonal antibodies specific to human B7.1 and human B7.2 antigen and primatized forms thereof having advantageous properties, i.e., affinity, immunosuppressive activity, which are useful as therapeutics. More specifically, these monkey antibodies and primatized forms thereof are to be used, e.g., as immunosuppressants, i.e., to block antigen driven immune responses, to treat autoimmune diseases such as psoriasis, rheumatoid arthritis, systemic erythematosus (SLE), type 1 diabetes mellitus, idiopathic thrombocytopenia purpura (ITP), and to prevent organ rejection.

It is another object of the invention to provide pharmaceutical compositions containing one or more monkey monoclonal antibodies specific to human B7 antigen, i.e., human B7.1 and/or human B7.2 antigen, or primatized forms thereof, and a pharmaceutically acceptable carrier or excipient. These compositions will be used, e.g., as immunosuppressants to treat autoimmune diseases, e.g., idiopathic thrombocytopenia purpura (ITP) and systemic lupus erythematosus (SLE), to block antigen driven immune responses, and to prevent organ rejection in transplant recipients.

It is another object of the invention to provide novel methods of therapy by administration of therapeutically effective amounts of one or more monkey or primatized monoclonal antibodies which specifically bind to B7 antigen, i.e., human B7.1 and/or B7.2 antigens. Such therapeutic methods are useful for treatment of diseases treatable by inhibition of the B7:CD28 pathway e.g., autoimmune diseases such as idiopathic thrombocytopenia purpura (ITP), systemic lupus erythematosus (SLE), type 1 diabetes mellitus, psoriasis, rheumatoid arthritis, multiple sclerosis, aplastic anemia, as well as for preventing rejection in transplantation subjects.

It is still another object of the invention to provide transfectants, e.g., CHO cells, which express at least the variable heavy and light domains of monkey monoclonal antibodies specific to the human B7.1 and/or B7.2 antigen.

It is another object of the invention to provide nucleic acid sequences which encode the variable heavy and/or light domains of monkey monoclonal antibodies specific to human B7.1 and/or human B7.2 antigen, and expression vectors which provide for the expression of primatized antibodies containing these nucleic acid sequences.

Definitions

The following terms are defined so that the invention may be more clearly understood.
Depleting antibody—an antibody which kills activated B cells or other antigen presenting cells.
Non-depleting antibody—an antibody which blocks the co-stimulatory action of B7 and T cell activating ligands CD28 and CTLA-4. Thus, it anergizes but does not eliminate the antigen presenting cell.
Primatized antibody—a recombinant antibody which has been engineered to contain the variable heavy and light domains of a monkey antibody, in particular, a cynomolgus monkey antibody, and which contains human constant domain sequences, preferably the human immunoglobulin gamma 1 or gamma 4 constant domain (or PE variant). The preparation of such antibodies is described in Newman et al, (1992), "Primatization of Recombinant Antibodies for Immunotherapy of Human Diseases: A Macaque/Human Chimeric Antibody Against Human CDH, *Biotechnology*, 10:1458–1460; also in commonly assigned Ser No. 08/379, 072 both of which are incorporated by reference in their entirety herein. These antibodies have been reported to exhibit a high degree of homology to human antibodies, i.e., 85–98%, display human effector functions, have reduced immunogenicity, and may exhibit high affinity to human antigens.

B7 antigens—B7 antigens in this application include, e.g., human B7, B7.1 and B7.2 antigens. These antigens bind to CD28 and/or CTLA-4. These antigens have a co-stimulatory role in T cell activation. Also, these B7 antigens all contain extracellular immunoglobulin superfamily V and C-like domains, a hydrophobic transmembrane region and a cytoplasmic tail. (See, Freeman et al, *Science*, 262:909, (1993)), and are heavily glycosylated.
Anti-B7 antibodies—Antibodies, preferably monkey monoclonal antibodies or primatized forms thereof, which specifically bind human B7 antigens, e.g., human B7.1 and/or B7.2 antigen with a sufficient affinity to block the B7:CD28 interaction and thereby induce immunosuppression.

BRIEF DESCRIPTION OF THE FIGURES

FIG. 2 depicts the NEOSPLA expression vector used to express the subject primatized antibodies specific to human B7.1 antigen.

FIG. 8a (SEQ ID NOS: 1–2) depicts the amino acid and nucleic acid sequence of a primatized form of the light chain of 7C10.

FIG. 8b (SEQ ID NOS: 3–4) depicts the amino acid and nucleic acid sequence of a primatized farm of the heavy chain of 7C10.

FIG. 9a (SEQ ID NOS: 5–6) depicts the amino acid and nucleic acid sequence of a primatized form of the light chain of 7B6.

FIG. 9b (SEQ ID NOS: 7–8) depicts the amino acid and nucleic acid sequence of a primatized form of the heavy chain of 7B6.

FIG. 10a (SEQ ID NOS: 9–10) depicts the amino acid and nucleic acid sequence of a primatized light chain 16C10.

FIG. 10b (SEQ ID NOS:11–12) depicts the amino acid and nucleic acid sequence of a primatized heavy chain 16C10.

DETAILED DESCRIPTION OF THE INVENTION

As described above, the present invention relates to the manufacture of novel monkey monoclonal antibodies which specifically bind human B7.1 and/or human B7.2 antigen, as well as primatized antibodies derived therefrom. These antibodies possess high affinity to human B7.1 and/or B7.2 and therefore may be used as immunosuppressants which inhibit the B7:CD86 pathway.

Preparation of monkey monoclonal antibodies will preferably be effected by screening of phage display libraries or by preparation of monkey heterohybridomas using B lymphocytes obtained from B7 (e.g., human B7.1 and/or B7.2) immunized monkeys.

As noted, the first method for generating anti-B7 antibodies involves recombinant phage display technology. This technique is generally described supra.

Essentially, this will comprise synthesis of recombinant immunoglobulin libraries against B7 antigen displayed on the surface of filamentous phage and selection of phage which secrete antibodies having high affinity to B7.1 and/or B7.2 antigen. As noted supra, preferably antibodies will be selected which bind to both human B7.1 and B7.2. To effect such methodology, the present inventors have created a unique library for monkey libraries which reduces the possibility of recombination and improves stability. This vector, pMS, is described in detail infra, and is shown in FIG. 1.

Essentially, to adopt phage display for use with macaque libraries, this vector contains specific primers for PCR amplifying monkey immunoglobulin genes. These primers are based on macaque sequences obtained while developing the primatized technology and databases containing human sequences.

Suitable primers are disclosed in commonly assigned Ser. No. 08/379,072 incorporated by reference herein.

The second method involves the immunization of monkeys, i.e., macaques, against human B7 antigen, preferably against human B7.1 and B7.2 antigen. The inherent advantage of macaques for generation of monoclonal antibodies is discussed supra. In particular, such monkeys, i.e., cynomolgus monkeys, may be immunized against human antigens or receptors. Moreover, the resultant antibodies may be used to make primatized antibodies according to the methodology of Newman et al, *Biotechnology,* 10, 1455–1460, (1992), and Newman et al, commonly assigned U.S. Ser. No. 08/379,072, filed Jan. 25, 1995, which are incorporated by reference in their entirety.

The significant advantage of antibodies obtained from cynomolgus monkeys is that these monkeys recognize many human proteins as foreign and thereby provide for the formation of antibodies, some with high affinity to desired human antigens, e.g., human surface proteins and cell receptors. Moreover, because they are phylogenetically close to humans, the resultant antibodies exhibit a high degree of amino acid homology to those produced in humans. As noted above, after sequencing macaque immunoglobulin light and heavy variable region genes, it was found that the sequence of each gene family was 85–88% homologous to its human counterpart (Newman et al, (1992), Id.).

Essentially, cynomolgus macaque monkeys are administered human B7 antigen, e.g., human B7.1 and/or human B7.2 antigen, B cells are isolated therefrom, e.g., lymph node biopsies are taken from the animals, and B lymphocytes are then fused with KH6/B5 (mouse×human) heteromyeloma cells using polyethylene glycol (PEG). Heterohybridomas secreting antibodies which bind human B7 antigen, e.g., human B7.1 and/or human B7.2 antigen, are then identified.

Antibodies which bind to both B7.1 and B7.2 are desirable because such antibodies potentially may be used to inhibit the interaction of B7.1 and B7.2, as well as B7 with their counter-receptors, i.e., human CTLA-4 and CD28. Antibodies against these epitopes may inhibit the interaction of both human B7.1 and human B7.2 with their counter receptors on the T cell. This may potentially provide synergistic effects.

However, antibodies which bind to only one of human B7 antigen, B7.1 antigen or B7.2 antigen, are also highly desirable because of the co-involvement of these molecules in T cell activation, clonal expansion lymphokine (IL-2) secretion, and responsiveness to antigen. Given that both human B7.1 and B7.2 bind to human CTLA-4 and CD28, it is probable that there is at least one common or homologous region (perhaps a shared conformational epitope or epitopes) to which macaque antibodies may potentially be raised.

The present inventors elected to immunize macaques against human B7.1 antigen using recombinant soluble B7.1 antigen produced in CHO cells and purified by affinity chromatography using a L307.4-sepharose affinity column. However, the particular source of human B7 antigen, human B7.1 antigen or human B7.2 antigen is not critical, provided that it is of sufficient purity to result in a specific antibody response to the particular administered B7 antigen and potentially to other B7 antigens.

The human B7 antigen, human B7.1 antigen (also called CD80) and human B7.2 antigen (also called CD86) genes have been cloned, and sequenced, and therefore may readily be manufactured by recombinant methods.

Preferably, the administered human B7 antigen, human B7.1 antigen and/or human B7.2 antigen will be administered in soluble form, e.g., by expression of a B7, B7.1 or B7.2 gene which has its transmembrane and cytoplasmic domains removed, thereby leaving only the extracellular portion, i.e., the extracellular superfamily V and C-like domains. (See, e.g., Grumet et al, *Hum. Immunol.,* 40(3), p. 228–234, 1994, which teaches expression of a soluble form of human B7, which is incorporated by reference in its entirety herein).

The macaques will be immunized with the B7, B7.1 and/or B7.2 antigen, preferably a soluble form thereof, under conditions which result in the production of antibodies specific thereto. Preferably, the soluble human B7, B7.1 or B7.2 antigen will be administered in combination with an adjuvant, e.g., Complete Freund's Adjuvant (CFA), Alum, Saponin, or other known adjuvants, as well as combinations thereof. In general, this will require repeated immunization, e.g., by repeated injection, over several months. For example, administration of soluble B7.1 antigen was effected in adjuvant, with booster immunizations, over a 3 to 4 month period, with resultant production of serum containing antibodies which bound human B7.1 antigen.

After immunization B cells are collected, e.g., by lymph node biopsies taken from the immunized animals and B lymphocytes fused with KH6/B5 (mouse×human) heteromyeloma cells using polyethylene glycol. Methods for preparation of such heteromyelomas are known and may be found in U.S. Ser. No. 08/379,072 by Newman et al, filed on Jan. 25, 1995 and incorporated by reference herein.

Heterohybridomas which secrete antibodies which bind human B7, B7.1 and/or B7.2 are then identified. This may be effected by known techniques. For example, this may be determined by ELISA or radioimmunoassay using enzyme or radionuclide labelled human B7, B7.1 and/or B7.2 antigen.

Cell lines which secrete antibodies having the desired specificity to human B7, B7.1 and/or B7.2 antigen are then subcloned to monoclonality.

In the present invention, the inventors screened purified antibodies for their ability to bind to soluble B7.1 antigen coated plates in an ELISA assay, antigen positive B cells, and CHO transfectomas which express human B7.1 antigen on their cell surface. In addition, the antibodies were screened for their ability to block B cell/T cell interactions as measured by IL-2 production and tritiated thymidine uptake in a mixed lymphocyte reaction (MLR), with B7 binding being detected using $^{125}$I-radiolabeled soluble B7.1 (SB7.1).

Also, affinity purified antibodies from macaques were tested for their reactivity against CHO transfectants which expressed B7.1/Ig fusion proteins, and against CHO cells which produced human B7.2 antigen. These results indicated that the B7.1 immune sera bound to the B7.2 transfectomas. Binding of antibodies to B7.2 antigen may be confirmed using soluble B7.2-Ig reagents. As discussed in the examples, this may be effected by producing and purifying B7.2-Ig from CHO transfectomas in sufficient quantities to prepare a B7.2-Ig-sepharose affinity column. Those antibodies which cross-react with B7.2 will bind the B7.2-Ig-sepharose column.

Figure 1:
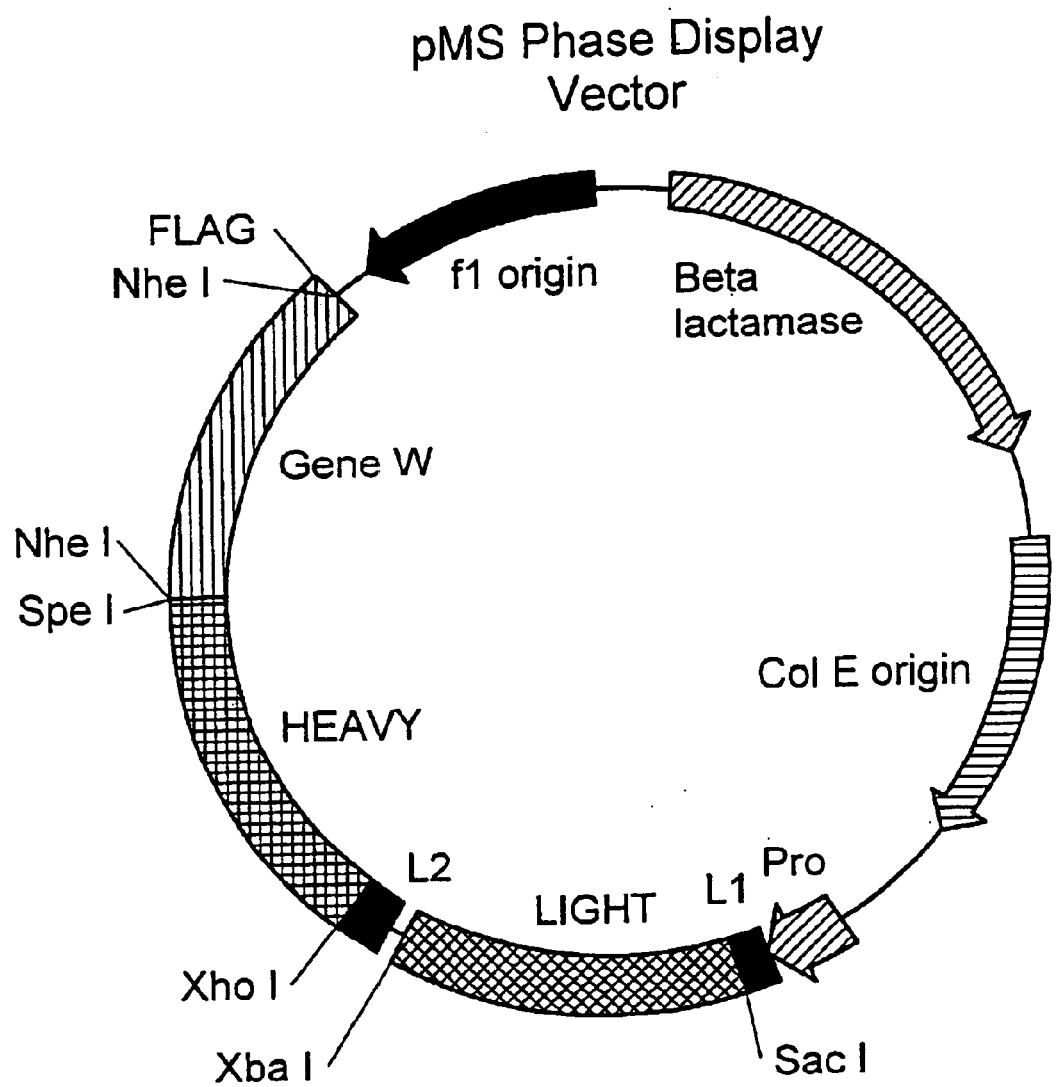
FIG. 1 depicts the pMS vector used to screen recombinant immunoglobulin libraries produced against B7 displayed on the surface of filamentous phage which contains primers based on macaque immunoglobulin sequences.

Cell lines which express antibodies which specifically bind to human B7 antigen, B7.1 antigen and/or B7.2 antigen are then used to clone variable domain sequences for the manufacture of primatized antibodies essentially as described in Newman et al, (1992), Id. and Newman et al, U.S. Ser. No. 379,072, filed Jan. 25, 1995, both of which are incorporated by reference herein. Essentially, this entails extraction of RNA therefrom, conversion to cDNA, and amplification thereof by PCR using Ig specific primers. Suitable primers are described in Newman et al, 1992, Id. and in U.S. Ser. No. 379,072. (See, in particular, FIG. 1 of U.S. Ser. No. 379,072).

The cloned monkey variable genes are then inserted into an expression vector which contains human heavy and light chain constant region genes. Preferably, this is effected using a proprietary expression vector of IDEC, Inc., referred to as NEOSPLA. This vector is shown in FIG. 2 and contains the cytomegalovirus promoter/enhancer, the mouse beta globin major promoter, the SV40 origin of replication, the bovine growth hormone polyadenylation sequence, neomycin phosphotransferase exon 1 and exon 2, human immunoglobulin kappa or lambda constant region, the dihydrofolate reductase gene, the human immunoglobulin gamma 1 or gamma 4 PE constant region and leader sequence. This vector has been found to result in very high level expression of primatized antibodies upon incorporation of monkey variable region genes, transfection in CHO cells, followed by selection in G418 containing medium and methotrexate amplification.

For example, this expression system has been previously disclosed to result in primatized antibodies having high avidity (Kd≦$10^{-10}$ M) against CD4 and other human cell surface receptors. Moreover, the antibodies have been found to exhibit the same affinity, specificity and functional activity as the original monkey antibody. This vector system is substantially disclosed in commonly assigned U.S. Ser. No. 379,072, incorporated by reference herein as well as U.S. Ser. No. 08/149,099, filed on Nov. 3, 1993, also incorporated by reference in its entirety herein. This system provides for high expression levels, i.e., >30 pg/cell/day.

As discussed infra, the subject inventors have selected four lead candidate monkey monoclonal antibodies which specifically bind the B7.1 antigen, and which may also bind the B7.2 antigen. These monkey monoclonal antibodies are referred to herein as 7B6, 16C10, 7C10 and 20C9.

As discussed in greater detail infra, these antibodies were evaluated for their ability to block B cell/T cell interactions as measured by IL-2 production and tritiated thymidine uptake in a mixed lymphocyte reaction for T cell binding experiments for T cell binding, human body coat peripheral blood lymphocytes were cultured for 3–6 days in the presence of PHA stimulator. B7 binding was radioassayed using $^{125}$I-radiolabeled soluble B7.1. The observed results indicate that all of these antibodies bind B7.1 antigen with high affinity and effectively block 2 cell/T cell interactions as evidenced by reduced IL-2 production and reduced proliferation of mixed lymphocyte cultures.

The properties of these particular monkey monoclonal antibodies are summarized below:

1. To demonstrate the monkey antibodies' ability to block the physical interaction between CTLA4-Ig, varying concentrations of the monkey anti-B7.1 antibodies and unlabeled CTLA4-IG were incubated with radiolabeled CTLA4-Ig$^{/125}$. The results of the inhibition assay showed that the IC50 (the concentration of inhibitor which results in 50% inhibition) for the monkey antibodies are:

| a: | 7C10:  | 0.39 µg/Ml |
| b: | 16C10: | 1.60 µg/Ml |
| c: | 20C9:  | 3.90 µg/Ml |
| d: | 7B6:   | 39.0 µg/Ml |

2. Scatchard analysis showed that the apparent affinity constants (Kd) for the monkey antibodies binding to B7-Ig coated plates were approximated to be:

| a: | 7C10:  | $6.2 \times 10^{-9}$M |
| b: | 16C10: | $8.1 \times 10^{-9}$M |
| c: | 7B6:   | $10.7 \times 10^{-9}$M |
| d: | 20C9:  | $16.8 \times 10^{-9}$M |

3. The antibodies were tested in vitro in a mixed lymphocyte reaction assay (MLR). The MLR showed that all 4 anti-B7.1 antibodies inhibit IL-2 production to different extents as shown by the following Ibgo values:

| a: | 7B6:   | 5.0 µg/M |
| b: | 16C10: | <0.1 µg/M |
| c: | 20C9:  | 2.0 µg/M |
| d: | 7C10:  | 5.0 µg/M |

4. The monkey anti-B7.1 antibodies were tested for their ability to bind B7 on human peripheral blood lymphocytes (PBL). FACS analysis showed that all 4 monkey antibodies tested positive.

5. Monkey antibodies 16C10, 7B6, 7C10 and 20C9 were tested for C1q binding by FACS analysis. Results showed 7C10 monkey Ig had strong human C1q binding after incubating with B7.1 CHO-transfected cells. 16C10 was positive, while 20C9 and 7B6 monkey antibodies were negative.

6. To select an animal model for path-tox studies, the monkey antibodies were tested with animal blood from different species. It was determined that the monkey anti-B7.1 antibodies cross-reacted with human, chimpanzee, and possibly baboon.

Based on these properties, it would appear that three monkey monoclonal antibodies possess the most advantageous properties, 16C10, 7C10 and 20C9, with 16C10 and 7C10 being somewhat better than 20C9.

Using the techniques described supra, and in commonly assigned U.S. Ser. No. 08/379,072, the present inventors have cloned the variable domains of 7C10, 7B6 and 16C10, and provide the amino acid and nucleic acid sequences of primatized forms of the 7C10 light chain, 7C10 heavy chain, 7B6 light chain, 7B6 heavy chain, 16C10 light chain and 16C10 heavy chain. These amino acid and nucleic acid sequences may be found in FIGS. 8a and 8b, 9a and 9b, and 10a and 10b. The DNA and amino acid sequence for the human gamma 1 constant domain may be found in U.S. Ser. No. 08/379,072.

As discussed supra, these primatized antibodies are preferably expressed using the NEOSPLA expression vector shown in FIG. 2 which is substantially described in commonly assigned Ser. Nos. 08/379,072 and 08/149,099, both of which applications are incorporated by reference herein.

As previously noted, the subject primatized antibodies will preferably contain either the human immunoglobulin gamma 1 or gamma 4 constant region, with gamma 4 preferably mutated at two positions to create gamma 4 PE. The gamma 4 PE mutant contains two mutations, a glutamic acid in the CH2 region introduced to eliminate residual FCR binding, and a proline substitution in the hinge region, intended to enhance the stability of the heavy chain disulfide bond interaction. (See, Alegre et al, *J. Immunol.*, 148, 3461–3468, (1992); and Angel et al, *Mol. Immunol.*, 30, 105–158, (1993), both of which are incorporated by reference herein).

Whether the subject primatized antibodies contain the gamma 1, gamma 4 or gamma 4 PE constant region largely depends on the particular disease target. Preferably, depleting and non-depleting primatized IgG1 and IgG4 antibodies are created and tested against specific disease targets.

Given the described binding and functional properties of the subject monkey monoclonal antibodies, these anti-B7.1 monoclonal antibodies and primatized forms thereof should be well suited as therapeutic agents for blocking the B7:CD28 interaction thereby providing for immunosuppression. In particular, given their high affinity to B7.1 antigen and ability to block B cell/T cell interactions as measured by IL-2 production and tritiated thymidine uptake in mixed lymphocyte culture as well as their ability to effectively inhibit antigen driven responses in donor spleen cell cultures as shown by reduced antigen specific IgG responses, IL-2 production and cell proliferation, these monkey monoclonal antibodies and primatized forms thereof should function as effective immunosuppressants which modulate the B7:CD28 pathway. This is significant for the treatment of many diseases wherein immunosuppression is therapeutically desirable, e.g., autoimmune diseases, to inhibit undesirable antigen specific IgG responses, and also for prevention of organ rejection and graft-versus-host disease. Essentially, the subject antibodies will be useful in treating any disease wherein suppression of the B7:CD28 pathway is therapeutically desirable.

Key therapeutic indications for the subject anti-B7.1 antibodies include, by way of example, autoimmune diseases such as idiopathic thrombocytopenia purpura (ITP), systemic lupus erythematosus (SLE), type 1 diabetes mellitus, multiple sclerosis, aplastic anemia, psoriasis and rheumatoid arthritis.

Another significant therapeutic indication of the subject anti-B7.1 antibodies is for prevention of graft-versus-host-disease (GVHD) during organ transplant and bone marrow transplant (BMT). The subject antibodies may be used to induce host tolerance to donor-specific alloantigens and thereby facilitate engraftment and reduce the incidence of graft rejection. It has been shown in a murine model of allogeneic cardiac transplantation that intravenous administration of CTLA4-Ig can result in immunosuppression or even induction of tolerance to alloantigen. (Lin et al, *J. Exp. Med.* 178:1801, 1993; Torka et al, *Proc. Natl. Acad. Sci., USA,* 89:11102, 1992). It is expected that the subject primatized anti-B7.1 antibodies will exhibit similar or greater activity.

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, or complement fixation. Such antibodies may be used as passive or active therapeutic agents against a number of human diseases, including B cell lymphoma, infectious diseases including AIDS, autoimmune and inflammatory diseases, and transplantation. The antibodies can be used either in their native form, or as part of an antibody/chelate, antibody/drug or antibody/toxin complex. Additionally, whole antibodies or antibody fragments (Fab$_2$, Fab, Fv) may be used as imaging reagents or as potential vaccines or immunogens in active immunotherapy for the generation of anti-idiotypic responses.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The anti-B7.1 antibodies (or fragments thereof) of this invention are useful for inducing immunosuppression, i.e., inducing a suppression of a human's or animal's immune system. This invention therefore relates to a method of prophylactically or therapeutically inducing immunosuppression in a human or other animal in need thereof by administering an effective, non-toxic amount of such an antibody of this invention to such human or other animal.

The ability of the compounds of this invention to induce immunosuppression has been demonstrated in standard tests used for this purpose, for example, a mixed lymphocyte reaction test or a test measuring inhibition of T-cell proliferation measured by thymidine uptake.

The fact that the antibodies of this invention have utility in inducing immunosuppression indicates that they should be useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphigus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., Coeliac disease, proctitis, eosinophilia gastroenteritis, mastocytosis, Crohn's disease and ulcerative colitis) and food-related allergies (e.g., migraine, rhinitis and eczema).

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies (or fragments thereof) of this invention should also be useful for treating tumors in a mammal. More specifically, they should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of an antibody. One skilled in the art would be able, by routine experimentation, to determine what an effective, non-toxic amount of anti-B7 antibody would be for the purpose of treating carcinogenic tumors. Generally, however, an effective dosage is expected to be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intraperitoneal, intramuscular, subcutaneous, rectal or vaginal administration. The subcutaneous and intramuscular forms of parenteral administration are generally preferred.

The daily parenteral and oral dosage regimens for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibodies of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibodies of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

The subject anti-B7.1 antibodies or fragments thereof may also be administered in combination with other moieties which modulate the B7:CD28 pathway. Such moieties include, by way of example, cytokines such as IL-7 and IL-10, CTLA4-Ig, soluble CTLA-4 and anti-CD28 antibodies and fragments thereof.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following formulations are, therefore, to be construed as merely illustrative embodiments and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5% by weight of an antibody or fragment thereof of the invention in 10% by volume propylene glycol and water. The solution is sterilized by filtration.

Ointment Composition

Antibody or fragment thereof of the invention 1.0 g.
White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.
Polawax GP 200 20.0 g.
Lanolin Anhydrous 2.0 g.
White Beeswax 2.5 g.
Methyl hydroxybenzoate 0.1 g.
Distilled Water to 100.0 g.

The polawax, beeswax and lanolin are heated together at 60° C. A solution of methyl hydroxybenzoate is added and homogenization is achieved using high speed stirring. The temperature is then allowed to fall to 50° C. The antibody or fragment thereof of the invention is then added and dispersed throughout, and the composition is allowed to cool with slow speed stirring.

Topical Lotion Composition

Antibody or fragment thereof of the invention 1.0 g.
Sorbitan Monolaurate 0.6 g.
Polysorbate 20 0.6 g.
Cetostearyl Alcohol 1.2 g.
Glycerin 6.0 g.
Methyl Hydroxybenzoate 0.2 g.
Purified Water B.P. to 100–00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.
Methyl Hydroxybenzoate 0.01 g.
Propyl Hydroxybenzoate 0.04 g.
Purified Water B.P. to 100–00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 µm pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5% of a lubricating agent, such as polysorbate 85 or oleic acid, and disperse such mixture in a propellant, such as freon, preferably in a combination of (1,2 dichlorotetrafluoroethane) and difluorochloro-methane and put into an appropriate aerosol container adapted for either intranasal or oral inhalation administration.

Composition for Administration by Inhalation

For an aerosol container with a capacity of 15–20 ml: dissolve 10 mg. of an antibody or fragment thereof of the invention in ethanol (6–8 ml.), add 0.1–0.2% of a lubricating agent, such as polysorbate 85 or oleic acid; and disperse such in a propellant, such as freon, preferably in combination of (1.2 dichlorotetrafluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as Ph adjusting and buffering agents, etc. The concentration of the antibody or fragment thereof of the invention in such pharmaceutical formulation can vary widely, i.e., from less than about 0.5%, usually at or at least about 1% to as much as is i5 or 20% by weight, and will be selected primarily based on fluid volumes, viscosities, etc., according to the particular mode of administration selected.

Thus, a pharmaceutical composition of the invention for intramuscular injection could be prepared to contain 1 Ml sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well known or will be apparent to those skilled in the art, and are described in more detail in, for example, *Remington's Pharmaceutical Science,* 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., *Science,* 253, 792–795 (1991).

To further illustrate the invention, the following examples are provided. These examples are not intended, nor are they to be construed, as further limiting the invention.

EXAMPLE 1

Recombinant immunoglobulin libraries displayed on the surface of filamentous phage were first described by McCafferty et al, *Nature,* 348:552–554, 1990 and Barbas et al, *Proc. Natl. Acad. Sci.,* USA 88:7978–7982, 1991. Using this technology, high affinity antibodies have been isolated from immune human recombinant libraries (Barbas et al, *Proc. Natl. Acad. Sci.,* USA 589:10164–10168, 1992). Although the phage display concept used is substantially similar to that described by Barbas, 1991, Id. the technique has been modified by the substitution of a unique vector for monkey libraries to reduce the possibility of recombination and improve stability. This vector, pMS, FIG. 1 contains a single lac promoter/operator for efficient transcription and translation of polycistronic heavy and light chain monkey DNA. This vector contains two different leader sequences, the omp A (Movva et al, *J. Biol. Chem.,* 255: 27–29, (1980), for the light chain and the pel B (Lei, *J. Bact.,* 4379–109:4383 (1987) for the heavy chain Fd. Both leader sequences are translated into hydrophobic signal peptides that direct the secretion of the heavy and light chain cloned products into the periplasmic space. In the oxidative environment of the periplasm, the two chains fold and disulfide bonds form to create stable Fab fragments. We derived the backbone of the vector from the phagemid bluescript. (Stratagene, La Jolla, Calif.). It contains the gene for the enzyme beta-lactamase that confers ampicillin (carbenicillin) resistance to bacteria that harbor pMS DNA. We also derived, from bluescript, the origin of replication of the multicopy plasmid ColEl and the origin of replication of the filamentous bacteriophage f1. The origin of replication of phage f1 (the so-called intragenic region), signals the initiation of synthesis of single stranded pMS DNA, the initiation of capsid formation and the termination of RNA synthesis by viral enzymes. The replication and assembly of pMS DNA strands into phage particles requires viral proteins that must be provided by a helper phage. We have used helper phage VCSM13 which is particularly suited for this, since it also contains a gene coding for kanamycin resistance. Bacteria infected with VCSM13 and pMS can be selected by adding both kanamycin and carbenicillin to the growth medium. The bacteria will ultimately produce filamentous phage particles containing either pMS or VCSM13 genomes. Packaging of the helper phage is less efficient than that of pMS, resulting in a mixed phage population that contains predominately recombinant pMS phages. The ends of the phage pick up minor coat proteins specific to each end. Of particular interest here is the gene III product which is present in three to five copies at one end of the phage. The gene III product is 406 amino acid residues and is required for phage infection of *E. coli* via the F pili. The first two domains of the heavy chain, the variable and the CH1 domain, are fused to the carboxy-terminal half of the gene III protein. This recombinant pili protein, directed by the pel B leader, is secreted to the peroplasm where it accumulates and forms disulfide bonds with the light chain before it is incorporated in the coat of the phage. Also, another vector contains a FLAG sequence engineered downstream of the gene III. The FLAG is an 8 amino acid peptide expressed at the carboxy terminal of the Fd protein. We are using commercially available monoclonal anti-FLAG M2 for both purification and detection of phage Fab by ELISA (Brizzard, *Bio Techniques,* 16(4):730–731, (1994)).

After constructing the vector pMS, we tested its ability to produce phage bound Fab using control antibody genes. We cloned an anti-tetanus toxoid antibody, (obtained from Dr. Carlos Barbas), into pMS and transformed XLI-blue. We co-infected our cells with VCSM13 and generated phage displaying the anti-tetanus toxoid antibody. We performed efficiency experiments where anti-tetanus toxoid phage were combined with phage beading an irrelevant antibody at 1:100,000. We performed three rounds of panning by applying 50 µl of the mixed phage to antigen (tetanus toxoid) coated polystyrene wells. Non-adherent phage were washed off and the adherent phage were eluted with acid. The eluted phage were used to infect a fresh aliquot of XL1-Blue bacteria and helper phage was added. After overnight amplification, phage were prepared and again panned on antigen coated plates. After three rounds of panning, we were able to show that we had successfully enriched for the anti-tetanus toxoid phage. The success of this technology also depends on the ability to prepare soluble Fabs for characterization of the final panned product. This was achieved by excising gene III from the pMS DNA using the restriction enzyme Nhe I followed by re-ligation. After the gene III was excised, the Fab was no longer displayed on the phage surface but accumulated in the piroplasmic space. Lysates were prepared from bacteria expressing soluble Fab and tested for antigen specificity using an ELISA. High levels of soluble Fab were detected.

In order to adapt phage display technology for use with macaque libraries, we developed specific primers for PCR amplifying monkey immunoglobulin genes. These were based on macaque sequences we obtained while developing the PRIMATIZED™ antibody technology (See, Ser. No. 08/379,072, incorporated by reference herein) and databases containing human sequences. (Kabat et al, (1991), "Sequences of Proteins of Immunological Interest," U.S. Dept. of Health and Human Services, National Institute of Health).

We developed three sets of primers to cover amplification of the macaque repertoire. Our first set of primers was designed for amplification of the heavy chain VH and CH1 (Fd) domains. It consisted of a 3' CH1 domain primer and six 5' VH family specific primers that bind in the framework 1 region. Our second set of primers, for amplifying the whole lambda chain, covers the many lambda chain subgroups. It consists of a 3' primer and three 5' degenerate primers that bind in the VL framework 1 region. Our third set of primers was designed for amplification of the kappa chain subgroups. It consists of one 3' primer and five VK framework 1 primers. Using each of these sets, PCR parameters were optimized to obtain strong enough signals from each primer pair so that ample material was available for cloning of the library. We recently created macaque combinatorial libraries in our pMS vector using these optimized PCR conditions. Bone marrow biopsies were taken from CD4 immune monkeys as the source of immunoglobulin RNA. The libraries contained approximately $10^6$ members and are currently being panned for specific binders on antigen coated wells.

EXAMPLE 2
Development of B7/CTLA-4 Reagents

We have generated a number of reagents for the purpose of immunizing monkeys, developing binding and functional assays in vitro, screening heterohybridomas and panning phage libraries. Table 1 lists each reagent and its intended purpose. In the case of B7.1, RNA was extracted from SB cells and converted to cDNA using reverse transcriptase. The first strand cDNA was PCR amplified using B7.1 specific primers and cloned into IDEC's NEOSPLA mammalian expression vectors. CHO cells were transfected with B7.1 NEOSPLA DNA and clones expressing membrane associated B7.1 were identified. The B7.1 fusion protein was generated similarly, except that the PCR amplified B7.1 gene was cloned into a NEOSPLA cassette vector containing the human CH2 and CH3 immunoglobulin genes. CHO cells were transformed with the B7.1/Ig NEOSPLA DNA and stable clones secreting B7.1/Ig fusion protein were amplified. In general, the B7.2 and CTLA4 reagents were generated in the same manner, except that for B7.2 the RNA was isolated from human spleen cells that had been stimulated 24 hours with anti-Ig and IL-4, and for the CTLA4 constructs the gene source was PHA activated human T cells.

TABLE 1

| Reagent | Purpose | CHO Expression |
| --- | --- | --- |
| Soluble B7.1 | Immunization, immunoassays | Yes |
| B7.1 Transfectant | Screening, ELISA | Yes |
| B7.1/Ig Fusion Protein | Inhibition studies, panning | Yes |
| B7.2 Transfectant | Screening, ELISA | Yes |
| B7.2/Ig Fusion Protein | Inhibition studies, panning | To be completed |
| CTLA4 Transfectant | Inhibition studies | To be completed |
| CTLA4/Ig | Inhibition studies | To be completed |

The availability of these reagents, together with monoclonal antibodies to B7.1 (L3074) (Becton Dickinson, 1994) and B7.2 (Fun-1 (Engel et al, *Blood,* 84, 1402–1407, (1994) and purified goat and rabbit antisera, specifically developed to detect monkey Fab fragments, facilitates identification of antibodies having the desired properties.

EXAMPLE 3
Investigation of the Immune Response in Cynomolgus Monkeys to Soluble and Cell Associated Human B7.1

To evaluate the feasibility of producing monkey antibodies to human B7.1 antigen, we first purified recombinant SB7.1 from CHO cell media by affinity chromatography using a L307.4-sepharose affinity column. SB7.1 was then injected, with adjuvant, into five mature cynomolgus macaques. After a 3 to 4 month period of booster immunizations, sera from the monkeys immunized with SB7.1 or human SE cells were tested for antigen binding.

Figure 3:
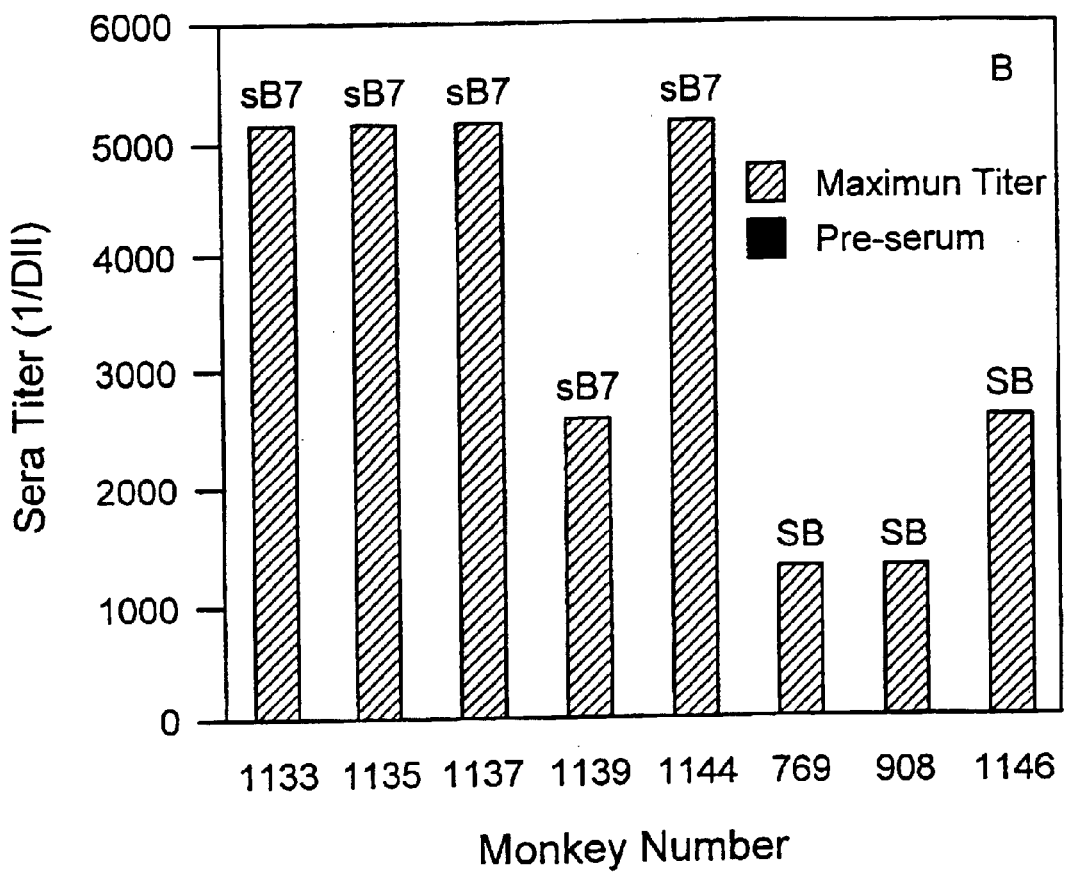
FIG. 3 depicts monkey serum anti-B7.1 titers directed against cell surface B7.1 on transfected CHO cells.

Serum samples from the five monkeys immunized with SB7.1. and three additional animals immunized with B7.1 positive human SB cells, were tested for antibody titers against membrane associated B7.1 expressed in transfected CHO cells. The results summarized in FIG. 3 showed that four out of five monkeys immunized with affinity-purified SB7.1 produced antibody titers in excess of 1:5000. The three animals immunized with SB cells containing cell associated B7.1 expressed lower titers of antibodies ranging from 1:1400 to 1:2800.

EXAMPLE 4

We purified antibodies from sera of all eight immunized monkeys using SB7.1-sepharose and then tested their ability to bind to 1) SB7.1 coated plates in ELISA; 2) antigen positive B cells and 3) B7.1 CHO transfectomas. In addition, they were evaluated for their ability to block B cell interactions as measured by IL-2 production and tritiated thymidine uptake in a mixed lymphocyte reaction (MLR). For T cell binding experiments, human buffy coat peripheral blood lymphocytes were cultured for 3–6 days in the presence of PHA stimulator. B7 binding was detected by radio assay using $^{125}$I-radiolabeled soluble B7.1 (SB7.1).

EXAMPLE 5
Direct Binding of Monkey Antibodies to Radiolabeled SB7

Figure 4:
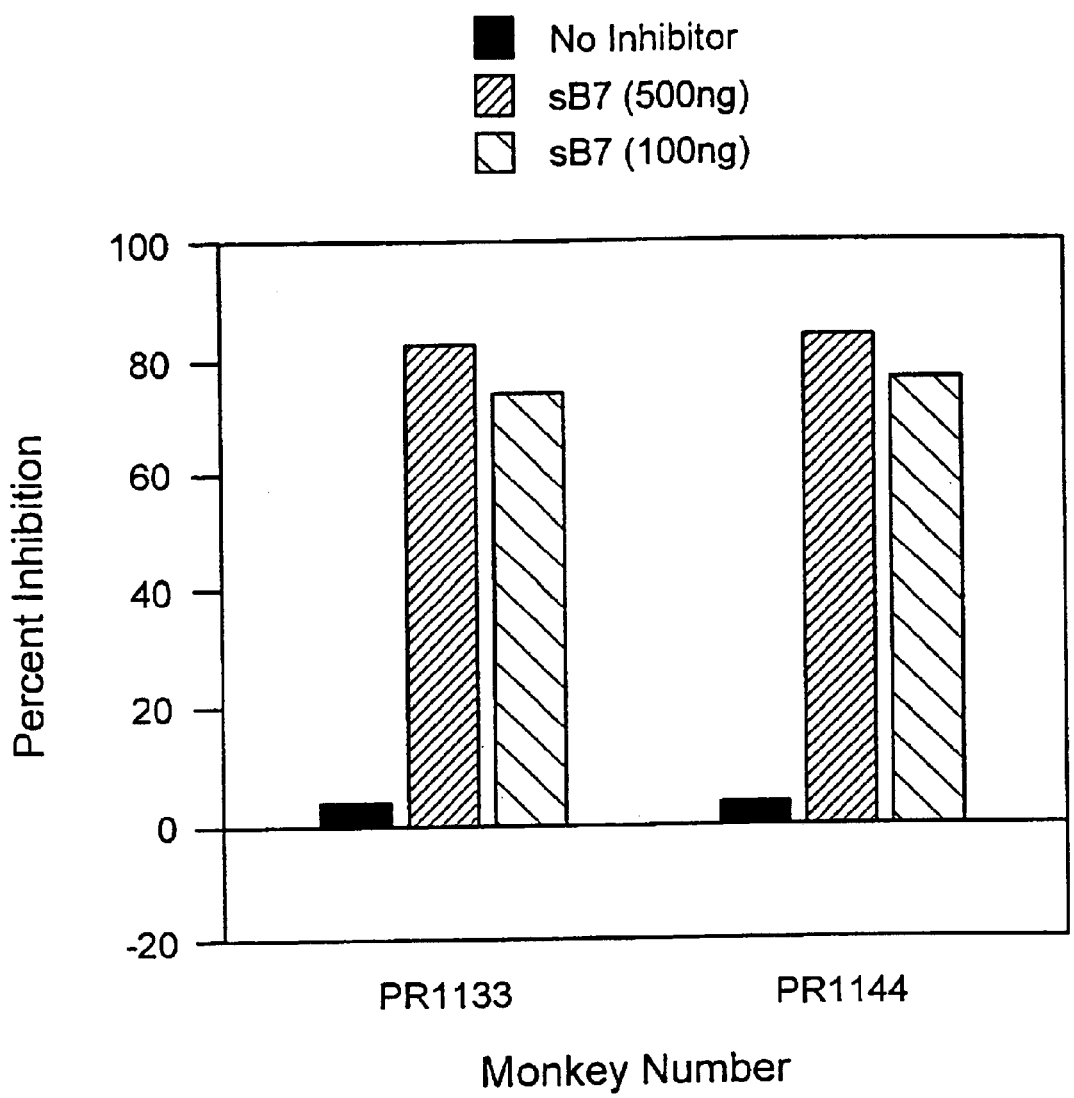
FIG. 4 depicts inhibition of radiolabeled sB7.1 binding by SB7.1 affinity-purified monkey antibodies in the presence of unlabeled SB7 and Mab L307.4 murine anti-B7.1.

$^{125}$I radiolabeled SB7.1 was tested for binding to anti-B7.1 antibodies at 4, 1 and 0.25 µg/ml in solution. The results shown in Table 2 suggest that most of the antibodies produced by monkeys immunized with SB7.1 were capable of binding the affinity-purified $^{125}$I-SB7.1 in a concentration dependent manner. To evaluate the specificity of binding to labeled SB7.1, unlabelled concentration dependent manner. To evaluate the specificity of binding to labeled SB7.1, unlabelled SB7.1 competition experiments were done with antibodies from two animals. Affinity-purified antibodies from monkeys 1133 and 1144 were coated onto microwell plates at 400 ng/well. Affinity-purified unlabeled SB7.1 (500 and 100 ng/well) was used as competitor. The results shown in FIG. 4 demonstrated that SB7.1 preparations are effective in inhibiting the $^{125}$I-SB7.1 from binding to the antibodies.

TABLE 2

Binding of SB7-$I^{125}$ to Monkey Antibodies Affinity Purified on a SB7-Sepharose Affinity Column

| Antibody | Monkey Numbers | | | | | | | |
| --- | --- | --- | --- | --- | --- | --- | --- | --- |
| (µg/ml) | 769 | 908 | 1133 | 1135 | 1137 | 1139 | 1144 | 1146 |
| 4 | 175 | 213 | 9,056 | 12,771 | 4,318 | 226 | 5,781 | 108 |
| 1 | 106 | 142 | 6,569 | 7,940 | 3,401 | 110 | 3,901 | 80 |
| 0.25 | 95 | 104 | 1,803 | 2,673 | 1,219 | 100 | 1,186 | 94 |

Data are mean values of duplicate assays and represent cpm SB7-$I^{125}$ bound.

EXAMPLE 6
Direct Binding of Radiolabeled Affinity-purified Monkey Antibodies to B7+ Cells and Inhibition by SB7.1

Figure 5:
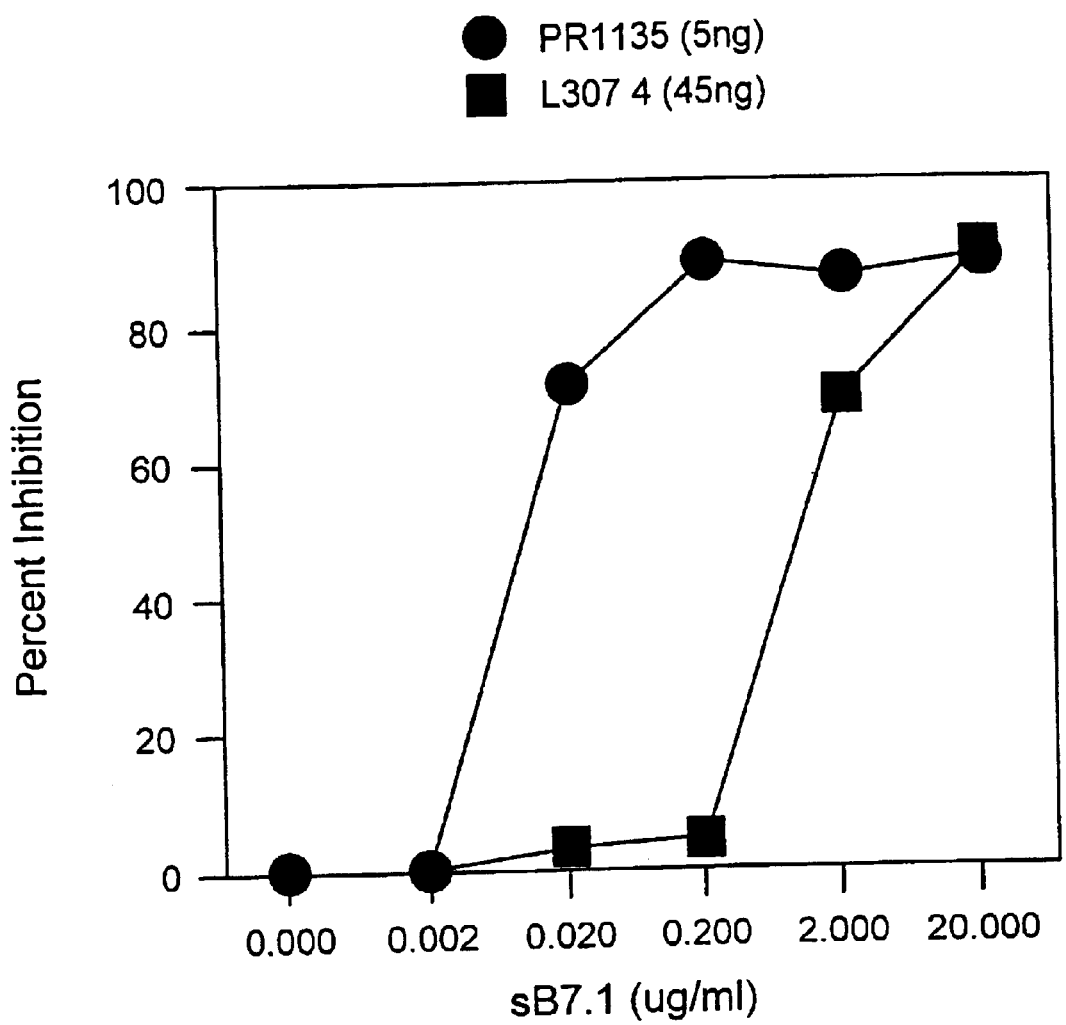
FIG. 5 depicts inhibition of binding of radiolabeled monkey 135 and L3707.4 anti-B7.1 antibodies to B7 positive human SB cells by competition with affinity-purified SB7.1.

Affinity-purified radiolabeled monkey anti-B7.1 antibodies from monkey PRI135 were compared with radiolabeled L307.4 MAb for direct binding to B7 positive human SB cells. As a specificity control, unlabeled SB7.1 (0.002–20 µg/mi) was added to compete with both radiolabeled antibodies. We demonstrated that monkey antibodies can bind cell associated B7.1 and are inhibited with SB7.1, as shown in FIG. 5. Inhibition as high as 90% was observed with SB7.1.

Figure 6:
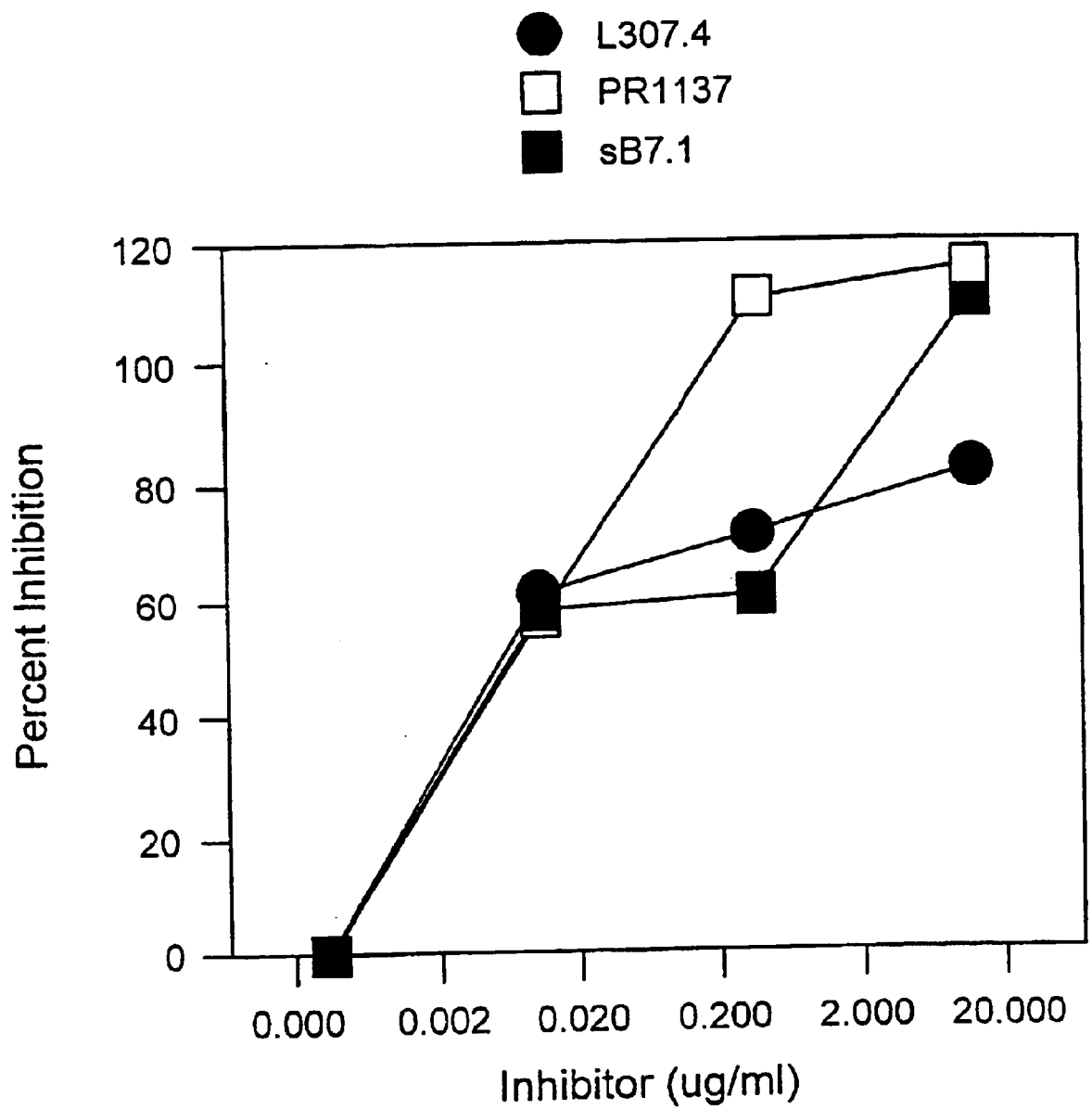
FIG. 6 depicts inhibition of radiolabeled B7-Ig binding to activated human peripheral blood T cells by competing with unlabeled SB7.1 murine anti-B7.1 (L307.4) and monkey 1127 affinity purified serum antibodies.

EXAMPLE 7
Direct Binding of Radiolabeled B7-Ig Fusion Protein to Activated T Cells and Inhibition by Affinity-purified Monkey Antibodies Human peripheral blood T lymphocytes were activated for 3–6 days and tested for direct binding of $^{125}$I-B7.1-Ig. Because of Fc receptor upregulation on activated human T cells, it was necessary to pre-incubate the cells with heat-aggregated pre-immune immunoglobulin to block Fc binding sites prior to addition of B7.1-Ig to the cells. A background control using SP2/0 murine myeloma cells was included to allow correction of the background binding. FIG. 6 shows that inhibition of $^{125}$I-B7.1-Ig fusion protein binding to activated T cells was achieved with affinity-purified monkey antibodies at concentrations from 200 to 8 µg/ml. Unlabeled SB7.1 and L307.4 MAb used as controls were also effective in inhibiting B7.1-Ig fusion protein cell binding.

Figure 7:
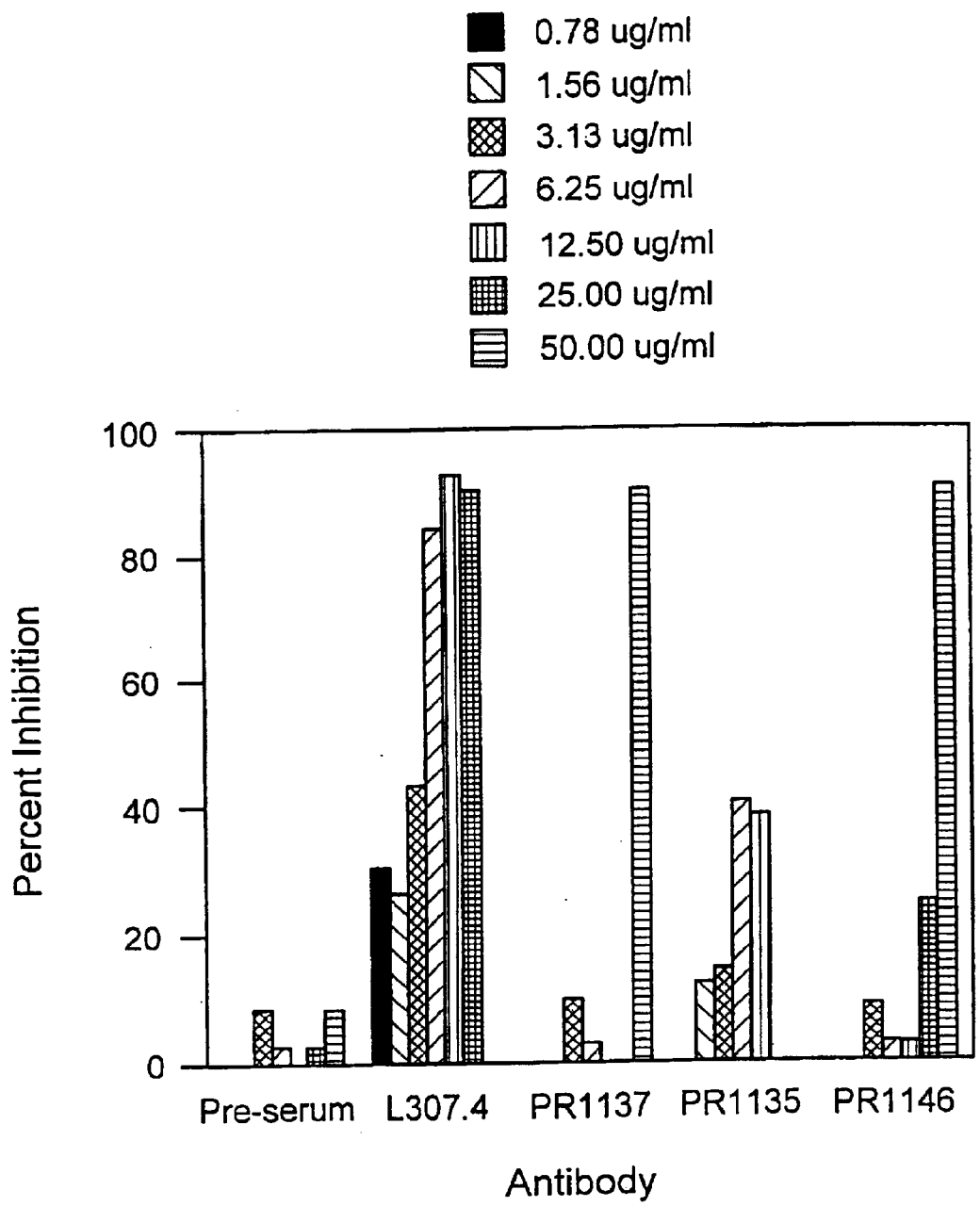
FIG. 7 depicts inhibition of IL-2 protein in mixed lymphocyte cultures by anti-B7.1 affinity-purified monkey serum antibodies.

EXAMPLE 8
Inhibition of IL-2 Production in Mixed Lymphocyte Reactions by Monkey Anti-B7 Antibodies The blocking of CD28/B7 interaction leads to inhibition of IL-2 production by T lymphocytes. In the experiment shown in FIG. 7, affinity-purified monkey antibodies from two monkeys immunized with SB7.1 (monkeys 1137 and 1135) and one immunized with B7 positive SB cells (monkey 1146) were evaluated for their abilities to inhibit human T cell activation in mixed lymphocyte reaction (MLR), as measured by inhibition of IL-2 production. The results of this experiment show that affinity-purified anti-B7.1 antibodies from monkeys 1146 and 1137 inhibited IL-2 production when added at concentrations of 50 µg/ml. Monkey 1135 antibodies could not be evaluated at the two highest concentrations due to lack of material, yet gave significant inhibition at lower concentrations. The murine MAb L307.4 was inhibitory at concentrations of 10 µg/ml. Other monkey sera tested at these concentrations were negative (data not shown). These results demonstrate that at least three of the monkeys immunized with both soluble and membrane associated forms of the B7 antigen are producing B7-blocking antibodies with immunosuppressive potential.

EXAMPLE 9
Investigation of Cross-reactivity in B7.1 Immunized Monkey Serum to B7.2 Antigen Antibodies raised against B7.1 are to be tested for cross-reactivity to B7.2. Preliminary results using B7.1 affinity-purified antibodies from B7.1 immune sera provided suggestive evidence of binding to B7.2 transfected CHO cells (not shown). These data should be confirmed by using soluble B7.2Ig reagents. We will first purify additional monkey antibodies from B7.1 immunized animals by affinity chromatography on B7.1Ig-sepharose. We will then produce and purify B7.2Ig from CHO cells in sufficient quantities to prepare a B7.2Ig-sepharose affinity column. We will select from the B7.1 specific antibody population those antibodies which cross-react with B7.2 by binding to the B7.2Ig-sepharose column. Any cross-reactive antibodies identified will be further characterized by direct binding to both B7.1 and B7.2 transfected CHO cells and inhibition of binding to B7.2 transfected cells by B7.1Ig.

EXAMPLE 10
Generation of a Phage Display Library

Recombinant phage display libraries are generated from B7.1 and B7.2 immune monkeys. Lymph node and bone marrow biopsies are performed 7–12 days after immunization to harvest RNA rich B cells and plasma cells. RNA is isolated from the lymphocytes using the method described by Chomczynski *Anal. Biochem.*, 162(1), 156–159, (1987). RNA is converted to cDNA using an oligo dT primer and reverse transcriptase. The first strand cDNA is divided into aliquots and PCR amplified using the sets of kappa, lambda, and heavy chain Fd region primers described earlier and either Pfu polymerase (Stratagene, San Diego) or Taq polymerase (Promega, Madison). The heavy chain PCR amplified products are pooled, cut with Xho VSpe I restriction enzymes and cloned into the vector pMS. Subsequently, the light chain PCR products are pooled, cut with Sac I/Xba I restriction enzymes, and cloned to create the recombinant library. XLI-Blue *E. coli* is transformed with the library DNA and super-infected with VCSM13 to produce the phage displaying antibodies. The library is panned four rounds on polystyrene wells coated with B7.1 or B7.2 antigen. Individual phage clones from each round of panning are analyzed. The pMS vector DNA is isolated and the gene III excised. Soluble Fab fragments are generated and tested in ELISA for binding to B7.1 and B7.2.

EXAMPLE 11
Characterization of Phage Fab Fragments

The monkey phage Fab fragments are characterized for their specificity and the ability to block B7.1-Ig and B7.2-Ig binding to CTLA-4-Ig or CTLA-4 transfected cells. Phage fragments are also characterized for cross-reactivity after first panning for 4 rounds on the B7 species used for immunization in order to select for high affinity fragments. Fab fragments identified from four rounds of panning either on B7.1 or B7.2 antigen coated surfaces are scaled up by infection and grown in 24 hour fermentation cultures of *E coli*. Fragments are purified by Kodak FLAG binding to a anti-FLAG affinity column. Purified phage Fabs are tested for affinity by an ELISA based direct binding modified Scatchard analysis (Katoh et al, *J. Chem. BioEng.*, 76:451–454, (1993)) using Goat anti-monkey Fab antibodies or anti-FLAG MAb conjugated with horseradish peroxidase. The anti-monkey Fab reagents will be absorbed against human heavy chain constant region Ig to remove any cross-reactivity to B7-Ig. Kd values are calculated for each fragment after measurements of direct binding to B7.1-Ig or B7.2-Ig coated plates.

EXAMPLE 12
Phage Fab Fragment Blocking of CTLA-4/B7 Binding

Fab fragments most effectively blocking the binding of B7-Ig at the lowest concentrations are selected as lead candidates. Selections are made by competing off $^{125}$I-B7-Ig binding to CTLA-4-Ig or CTLA-4 transfected cells. Additional selection criteria include, blocking of mixed lymphocyte reaction (MLR), as measured by inhibiting 3H-thymidine uptake in responder cells (Azuma et al, *J. Exp. Med.*, 177:845–850,; Azuma et al, *Nature*, 301:76–79, (1993)) and direct analysis of IL-2 production using IL-2 assay kits. The three or four candidates which are most effective in inhibiting of MLR and CTLA-4 binding assays are chosen for cloning into the above-described mammalian expression vector for transfection into CHO cells and expression of chimeric monkey/human antibodies.

EXAMPLE 13
Generation of Monkey Heterohybridomas

Monkey heterohybridomas secreting monoclonal antibodies are generated from existing immunized animals whose sera tested positive for B7.1 and/or B7.2. Lymph node biopsies are taken from animals positive to either, or both, antigens. The method of hybridoma production is similar to the established method used for the generation of monkey anti-CD4 antibodies (Newman, 1992(Id.)). Monkeys with high serum titers will have sections of inguinal lymph nodes removed under anesthesia. Lymphocytes are washed from the tissue and fused with KH6/B5 heteromyeloma cells (Carrol et al, *J. Immunol. Meth.*, 89:61–72, (1986)) using polyethylene glycol (PEG). Hybridomas are selected on H.A.T. media and stabilized by repeated subcloning in 96 well plates.

Monkey monoclonal antibodies specific for B7.1 antigen are screened for cross-reactivity to B7.2. Monkey anti-B7 antibodies will be characterized for blocking of B7/CTLA-4 binding using the $^{125}$I-B7-Ig binding assay. Inhibition of MLR by 3H-Thymidine uptake and direct measurement of IL-2 production is used to select three candidates. Two candidates will be brought forward in Phase II studies and expressed in CHO cells while repeating all functional studies. For the purposes of developing an animal model for in vivo pharmacology, anti-B7 antibodies will be tested on cells of several animal species. The establishment of an animal model will allow preclinical studies to be carried out for the selected clinical indication.

EXAMPLE 14

As discussed supra, using the above heterohybridoma methods, 4 lead monkey anti-B7.1 antibodies have been identified: 16C10, 7B6, 7C10 and 20C9. These antibodies were characterized as follows:

To demonstrate the monkey antibodies' ability to block the physical interaction between CTLA4-Ig, varying concentrations of the monkey anti-B7.1 antibodies and unlabeled CTLA4-Ig were incubated with radiolabeled CTLA4-Ig$^{I125}$. The results of the inhibition assay showed that the IC50 (the concentration of inhibitor which results in 50% inhibition) for the monkey antibodies are:

| a: | 7C10:  | 0.39 µg/Ml |
| b: | 16C10: | 1.60 µg/Ml |
| c: | 20C9:  | 3.90 µg/Ml |
| d: | 7B6:   | 39.0 µg/Ml |

Scatchard analysis showed that the apparent affinity constants (Kd) for the monkey antibodies binding to B7-Ig coated plates were approximated to be:

| a: | 7C10:  | $6.2 \times 10^{-9}$M  |
| b: | 16C10: | $8.1 \times 10^{-9}$M  |
| c: | 7B6:   | $10.7 \times 10^{-9}$M |
| d: | 20C9:  | $16.8 \times 10^{-9}$M |

The antibodies were tested in vitro in a mixed lymphocyte reaction assay (MLR). The MLR showed that all 4 anti-B7.1 antibodies inhibit IL-2 production to different extents:

| a: | 7B6:   | 5.0 µg/Ml |
| b: | 16C10: | 0.1 µg/Ml |
| c: | 20C9:  | 2.0 µg/Ml |
| d: | 7C10:  | 5.0 µg/Ml |

The monkey anti-B7.1 antibodies were tested for their ability to bind B7 on human peripheral blood lymphocytes (PBL). FACS analysis showed that all 4 monkey antibodies tested positive.

Monkey antibodies 16C10, 7B6, 7C10 and 20C9 were tested for C1q binding by FACS analysis. Results showed 7C10 monkey Ig had strong human C1q binding after incubating with B7.1 CHO-transfected cells. 16C10 was negative, as were the 20C9 and 7B6 monkey antibodies.

EXAMPLE 15

Using the primatized antibody methodology incorporated by reference to commonly assigned U.S. Ser. No. 08/379,072, and using the NEOSPLA vector system shown in FIG. 2, the heavy and light variable domains of 7C10, 7B6 and 16C10 were cloned and primatized forms thereof have been synthesized in CHO cells using the NEOSPLA vector system. The amino acid and nucleic acid sequences for the primatized 7C10 light and heavy chain, 7B6 light and heavy chain, and 16C10 light and heavy chain are respectively shown in FIGS. 8a, 8b, 9a, 9b, 10a and 10b.

It is expected that these primatized antibodies, given their probable low antigenicity and human effector function, will be well suited as therapeutics. In fact, it has recently been shown that primatized 16C10 exhibits human $C1_q$ binding, whereas 16C10 does not.

Those skilled in the art will recognize or be able to ascertain using no more than routine experimentation many equivalents to the specific embodiments of the invention described herein. Such equivalents are intended to be embraced by the following claims.

What is claimed is:

1. A method of treating B cell lymphoma comprising administering a therapeutically effective amount of an anti-CD80 antibody, wherein said antibody binds the same epitope as an anti-CD80 antibody selected from the group consisting of 7C10, which has the variable region sequences shown in FIGS. 8a and 8b (amino acid sequences of SEQ ID NOs. 1–2 and 3–4 respectively); 7B6, which has the variable region sequences shown in FIGS. 9a and 9b (amino acid sequences of SEQ ID NOs. 5–6 and 7–3 respectively); and 16C10, which has the variable region sequences shown in FIGS. 10a and 10b (amino acid sequences of SEQ ID NOs. 9–10 and 11–12 respectively).

2. The method of claim 1 wherein said anti-CD80 antibody binds the same epitope as an anti-CD80 antibody selected from the group consisting of 16C10, 7C10, 20C9 and 7B6.

3. A method of treating B cell lymphoma comprising administering a therapeutically effective amount of an anti-CD80 antibody, wherein said antibody binds the same epitope as an anti-CD80 antibody selected from the group consisting of 7C10, which has the variable region sequences shown in FIGS. 8a and 8b (amino acid sequences of SEQ ID NOs. 1–2 and 3–4 respectively); 7B6, which has the variable region sequences shown in FIGS. 9a and 9b (amino acid sequences of SEQ ID NOs. 5–6 and 7–3 respectively); and 16C10, which has the variable region sequences shown in FIGS. 10a and 10b (amino acid sequences of SEQ ID NOs. 9–10 and 11–12 respectively), wherein said antibody is a non-depleting antibody.

4. A method of treating B cell lymphoma comprising administering a therapeutically effective amount of an anti-CD80 antibody, wherein said antibody is a primatized ® antibody having the variable region sequences of an anti-CD80 antibody selected from the group consisting of 7C10, which has the variable region sequences shown in in FIGS. 8a and 8b (amino acid sequences of SEQ ID NOs. 1–2 and 3–4 respectively); 7B6, which has the variable region sequences shown in FIGS. 9a and 9b (amino acid sequences of SEQ ID NOs. 5–6 and 7–8, respectively); and 16C10, which has the variable region sequences shown in FIGS. 10a and 10b (amino acid sequences of SEQ ID NOs. 9–10 and 11–12 respectively).

5. The method of claim 4 where the antibody is a primatized® antibody having the variable region sequences of antibody 16C10 shown in FIGS. 10a and 10b (amino acid sequences of SEQ ID NOs. 9–10 and 11–12, respectively).

* * * * *

UNITED STATES PATENT AND TRADEMARK OFFICE
CERTIFICATE OF CORRECTION

PATENT NO. : 6,893,638 B2
DATED : May 17, 2005
INVENTOR(S) : Anderson et al.

It is certified that error appears in the above-identified patent and that said Letters Patent is hereby corrected as shown below:

Column 57,
Line 42, the text of "sequences of SEQ ID NOs. 5-6 and 7-3 respectively); and" should be corrected to -- sequences of SEQ ID NOs. 5-6 and 7-8 respectively); and --.

Column 58,
Line 33, the text of "sequences of SEQ ID NOs. 5-6 and 7-3 respectively); and" should be corrected to -- sequences of SEQ ID NOs. 5-6 and 7-8 respectively); and --.

Signed and Sealed this

Nineteenth Day of July, 2005

JON W. DUDAS
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

```
        (i) SEQUENCE CHARACTERISTICS:
            (A) LENGTH: 705 base pairs
            (B) TYPE: nucleic acid
            (C) STRANDEDNESS: Not Relevant
            (D) TOPOLOGY: linear (ii) MOLECULE TYPE: peptide (ix) FEATURE:
            (A) NAME/KEY: CDS
            (B) LOCATION: 1..705

(ix) FEATURE:
            (A) NAME/KEY: mat_peptide
            (B) LOCATION: 1..705

(xi) SEQUENCE DESCRIPTION: SEQ ID NO:1:

ATG AGG GTC CCC GCT CAG CTC CTG GGG CTC CTG CTG CTC TGG CTC CCA        48
Met Arg Val Pro Ala Gln Leu Leu Gly Leu Leu Leu Leu Trp Leu Pro
 1               5                  10                  15

GGT GCA CGA TGT GCC TAT GAA CTG ACT CAG CCA CCC TCG GTG TCA GTG        96
Gly Ala Arg Cys Ala Tyr Glu Leu Thr Gln Pro Pro Ser Val Ser Val
             20                  25                  30

TCC CCA GGA CAG ACG GCC AGG ATC ACC TGT GGG GGA GAC AAC AGT AGA       144
Ser Pro Gly Gln Thr Ala Arg Ile Thr Cys Gly Gly Asp Asn Ser Arg
         35                  40                  45

AAT GAA TAT GTC CAC TGG TAC CAG CAG AAG CCA GCG CGG GCC CCT ATA       192
Asn Glu Tyr Val His Trp Tyr Gln Gln Lys Pro Ala Arg Ala Pro Ile
 50                  55                  60

CTG GTC ATC TAT GAT GAT AGT GAC CGG CCC TCA GGG ATC CCT GAG CGA       240
Leu Val Ile Tyr Asp Asp Ser Asp Arg Pro Ser Gly Ile Pro Glu Arg
 65                  70                  75                  80

TTC TCT GGC TCC AAA TCA GGG AAC ACC GCC ACC CTG ACC ATC AAC GGG       288
Phe Ser Gly Ser Lys Ser Gly Asn Thr Ala Thr Leu Thr Ile Asn Gly
                 85                  90                  95

GTC GAG GCC GGG GAT GAG GCT GAC TAT TAC TGT CAG GTG TGG GAC AGG       336
Val Glu Ala Gly Asp Glu Ala Asp Tyr Tyr Cys Gln Val Trp Asp Arg
            100                 105                 110

GCT AGT GAT CAT CCG GTC TTC GGA GGA GGG ACC CGG GTG ACC GTC CTA       384
Ala Ser Asp His Pro Val Phe Gly Gly Gly Thr Arg Val Thr Val Leu
        115                 120                 125

GGT CAG CCC AAG GCT GCC CCC TCG GTC ACT CTG TTC CCG CCC TCC TCT       432
Gly Gln Pro Lys Ala Ala Pro Ser Val Thr Leu Phe Pro Pro Ser Ser
    130                 135                 140

GAG GAG CTT CAA GCC AAC AAG GCC ACA CTG GTG TGT CTC ATA AGT GAC       480
Glu Glu Leu Gln Ala Asn Lys Ala Thr Leu Val Cys Leu Ile Ser Asp
145                 150                 155                 160

TTC TAC CCG GGA GCC GTG ACA GTG GCC TGG AAG GCA GAT AGC AGC CCC       528
Phe Tyr Pro Gly Ala Val Thr Val Ala Trp Lys Ala Asp Ser Ser Pro
                165                 170                 175

GTC AAG GCG GGA GTG GAG ACC ACC ACA CCC TCC AAA CAA AGC AAC AAC       576
Val Lys Ala Gly Val Glu Thr Thr Thr Pro Ser Lys Gln Ser Asn Asn
            180                 185                 190

AAG TAC GCG GCC AGC AGC TAC CTG AGC CTG ACG CCT GAG CAG TGG AAG       624
Lys Tyr Ala Ala Ser Ser Tyr Leu Ser Leu Thr Pro Glu Gln Trp Lys
        195                 200                 205

TCC CAC AGA AGC TAC AGC TGC CAG GTC ACG CAT GAA GGG AGC ACC GTG       672
Ser His Arg Ser Tyr Ser Cys Gln Val Thr His Glu Gly Ser Thr Val
    210                 215                 220

GAG AAG ACA GTG GCC CCT ACA GAA TGT TCA TGA                           705
Glu Lys Thr Val Ala Pro Thr Glu Cys Ser *
225                 230                 235
```

(2) INFORMATION FOR SEQ ID NO:2:

(i) SEQUENCE CHARACTERISTICS:
        (A) LENGTH:  234 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Val Pro Ala Gln Leu Leu Gly Leu Leu Leu Trp Leu Pro
 1               5                  10                  15

Gly Ala Arg Cys Ala Tyr Glu Leu Thr Gln Pro Pro Ser Val Ser Val
                20                  25                  30

Ser Pro Gly Gln Thr Ala Arg Ile Thr Cys Gly Gly Asp Asn Ser Arg
                35                  40                  45

Asn Glu Tyr Val His Trp Tyr Gln Gln Lys Pro Ala Arg Ala Pro Ile
            50                  55                  60

Leu Val Ile Tyr Asp Asp Ser Asp Arg Pro Ser Gly Ile Pro Glu Arg
 65                  70                  75                  80

Phe Ser Gly Ser Lys Ser Gly Asn Thr Ala Thr Leu Thr Ile Asn Gly
                85                  90                  95

Val Glu Ala Gly Asp Glu Ala Asp Tyr Tyr Cys Gln Val Trp Asp Arg
                100                 105                 110

Ala Ser Asp His Pro Val Phe Gly Gly Gly Thr Arg Val Thr Val Leu
                115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230                 235
```

(2) INFORMATION FOR SEQ ID NO:3:

(i) SEQUENCE CHARACTERISTICS:
        (A) LENGTH:  1430 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1431

(ix) FEATURE:
        (A) NAME/KEY: mat_peptide
        (B) LOCATION: 1..1431

(xi) SEQUENCE DESCRIPTION: SEQ ID NO:3:

ATG AAA CAC CTG TGG TTC TTC CTC CTC CTG GTG GCA GCT CCC AGA TGG    48

```
                                                              -continued

Met Lys His Leu Trp Phe Phe Leu Leu Leu Val Ala Ala Pro Arg Trp
 1               5                   10                  15

GTC CTG TCC CAG GTG AAG CTG CAG CAG TGG GGC GAA GGA CTT CTG CAG        96
Val Leu Ser Gln Val Lys Leu Gln Gln Trp Gly Glu Gly Leu Leu Gln
             20                  25                  30

CCT TCG GAG ACC CTG TCC CGC ACC TGC GTT GTC TCT GGT GGC TCC ATC       144
Pro Ser Glu Thr Leu Ser Arg Thr Cys Val Val Ser Gly Gly Ser Ile
         35                  40                  45

AGC GGT TAC TAC TAC TGG ACC TGG ATC CGC CAG ACC CCA GGG AGG GGA       192
Ser Gly Tyr Tyr Tyr Trp Thr Trp Ile Arg Gln Thr Pro Gly Arg Gly
     50                  55                  60

CTG GAG TGG ATT GGC CAT ATT TAT GGT AAT GGT GCG ACC ACC AAC TAC       240
Leu Glu Trp Ile Gly His Ile Tyr Gly Asn Gly Ala Thr Thr Asn Tyr
 65              70                  75                  80

AAT CCC TCC CTC AAG AGT CGA GTC ACC ATT TCA AAA GAC ACG TCC AAG       288
Asn Pro Ser Leu Lys Ser Arg Val Thr Ile Ser Lys Asp Thr Ser Lys
                 85                  90                  95

AAC CAG TTC TTC CTG AAC TTG AAT TCT GTG ACC GAC GCG GAC ACG GCC       336
Asn Gln Phe Phe Leu Asn Leu Asn Ser Val Thr Asp Ala Asp Thr Ala
             100                 105                 110

GTC TAT TAC TGT GCG AGA GGC CCT CGC CCT GAT TGC ACA ACC ATT TGT       384
Val Tyr Tyr Cys Ala Arg Gly Pro Arg Pro Asp Cys Thr Thr Ile Cys
         115                 120                 125

TAT GGC GGC TGG GTC GAT GTC TGG GGC CCG GGA GAC CTG GTC ACC GTC       432
Tyr Gly Gly Trp Val Asp Val Trp Gly Pro Gly Asp Leu Val Thr Val
     130                 135                 140

TCC TCA GCT AGC ACC AAG GGC CCA TCG GTC TTC CCC CTG GCA CCC TCC       480
Ser Ser Ala Ser Thr Lys Gly Pro Ser Val Phe Pro Leu Ala Pro Ser
145                 150                 155                 160

TCC AAG AGC ACC TCT GGG GGC ACA GCG GCC CTG GGC TGC CTG GTC AAG       528
Ser Lys Ser Thr Ser Gly Gly Thr Ala Ala Leu Gly Cys Leu Val Lys
                 165                 170                 175

GAC TAC TTC CCC GAA CCG GTG ACG GTG TCG TGG AAC TCA GGC GCC CTG       576
Asp Tyr Phe Pro Glu Pro Val Thr Val Ser Trp Asn Ser Gly Ala Leu
             180                 185                 190

ACC AGC GGC GTG CAC ACC TTC CCG GCT GTC CTA CAG TCC TCA GGA CTC       624
Thr Ser Gly Val His Thr Phe Pro Ala Val Leu Gln Ser Ser Gly Leu
         195                 200                 205

TAC TCC CTC AGC AGC GTG GTG ACC GTG CCC TCC AGC AGC TTG GGC ACC       672
Tyr Ser Leu Ser Ser Val Val Thr Val Pro Ser Ser Ser Leu Gly Thr
     210                 215                 220

CAG ACC TAC ATC TGC AAC GTG AAT CAC AAG CCC AGC AAC ACC AAG GTG       720
Gln Thr Tyr Ile Cys Asn Val Asn His Lys Pro Ser Asn Thr Lys Val
225                 230                 235                 240

GAC AAG AAA GCA GAG CCC AAA TCT TGT GAC AAA ACT CAC ACA TGC CCA       768
Asp Lys Lys Ala Glu Pro Lys Ser Cys Asp Lys Thr His Thr Cys Pro
                 245                 250                 255

CCG TGC CCA GCA CCT GAA CTC CTG GGG GGA CCG TCA GTC TTC CTC TTC       816
Pro Cys Pro Ala Pro Glu Leu Leu Gly Gly Pro Ser Val Phe Leu Phe
             260                 265                 270

CCC CCA AAA CCC AAG GAC ACC CTC ATG ATC TCC CGG ACC CCT GAG GTC       864
Pro Pro Lys Pro Lys Asp Thr Leu Met Ile Ser Arg Thr Pro Glu Val
         275                 280                 285

ACA TGC GTG GTG GTG GAC GTG AGC CAC GAA GAC CCT GAG GTC AAG TTC       912
Thr Cys Val Val Val Asp Val Ser His Glu Asp Pro Glu Val Lys Phe
     290                 295                 300

AAC TGG TAC GTG GAC GGC GTG GAG GTG CAT AAT GCC AAG ACA AAG CCG       960
Asn Trp Tyr Val Asp Gly Val Glu Val His Asn Ala Lys Thr Lys Pro
305                 310                 315                 320
```

-continued

| | | | | | | | | | | | | |
|---|---|---|---|---|---|---|---|---|---|---|---|---|
| CGG | GAG | GAG | CAG | TAC | AAC | AGC | ACG | TAC | CGT | GTG | GTC | AGC | GTC | CTC | ACC | 1008 |
| Arg | Glu | Glu | Gln | Tyr | Asn | Ser | Thr | Tyr | Arg | Val | Val | Ser | Val | Leu | Thr | |
| | | | 325 | | | | | 330 | | | | | 335 | | | |

```
CGG GAG GAG CAG TAC AAC AGC ACG TAC CGT GTG GTC AGC GTC CTC ACC      1008
Arg Glu Glu Gln Tyr Asn Ser Thr Tyr Arg Val Val Ser Val Leu Thr
                325                 330                 335

GTC CTG CAC CAG GAC TGG CTG AAT GGC AAG GAG TAC AAG TGC AAG GTC      1056
Val Leu His Gln Asp Trp Leu Asn Gly Lys Glu Tyr Lys Cys Lys Val
                340                 345                 350

TCC AAC AAA GCC CTC CCA GCC CCC ATC GAG AAA ACC ATC TCC AAA GCC      1104
Ser Asn Lys Ala Leu Pro Ala Pro Ile Glu Lys Thr Ile Ser Lys Ala
                355                 360                 365

AAA GGG CAG CCC CGA GAA CCA CAG GTG TAC ACC CTG CCC CCA TCC CGG      1152
Lys Gly Gln Pro Arg Glu Pro Gln Val Tyr Thr Leu Pro Pro Ser Arg
    370                 375                 380

GAT GAG CTG ACC AAG AAC CAG GTC AGC CTG ACC TGC CTG GTC AAA GGC      1200
Asp Glu Leu Thr Lys Asn Gln Val Ser Leu Thr Cys Leu Val Lys Gly
385                 390                 395                 400

TTC TAT CCC AGC GAC ATC GCC GTG GAG TGG GAG AGC AAT GGG CAG CCG      1248
Phe Tyr Pro Ser Asp Ile Ala Val Glu Trp Glu Ser Asn Gly Gln Pro
                405                 410                 415

GAG AAC AAC TAC AAG ACC ACG CCT CCC GTG CTG GAC TCC GAC GGC TCC      1296
Glu Asn Asn Tyr Lys Thr Thr Pro Pro Val Leu Asp Ser Asp Gly Ser
                420                 425                 430

TTC TTC CTC TAC AGC AAG CTC ACC GTG GAC AAG AGC AGG TGG CAG CAG      1344
Phe Phe Leu Tyr Ser Lys Leu Thr Val Asp Lys Ser Arg Trp Gln Gln
                435                 440                 445

GGG AAC GTC TTC TCA TGC TCC GTG ATG CAT GAG GCT CTG CAC AAC CAC      1392
Gly Asn Val Phe Ser Cys Ser Val Met His Glu Ala Leu His Asn His
    450                 455                 460

TAC ACG CAG AAG AGC CTC TCC CTG TCT CCG GGT AAA TGA                  1431
Tyr Thr Gln Lys Ser Leu Ser Leu Ser Pro Gly Lys
465                 470                 475

(2) INFORMATION FOR SEQ ID NO:4:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:4:

Met Lys His Leu Trp Phe Phe Leu Leu Leu Val Ala Ala Pro Arg Trp
  1               5                  10                  15

Val Leu Ser Gln Val Lys Leu Gln Gln Trp Gly Glu Gly Leu Leu Gln
                20                  25                  30

Pro Ser Glu Thr Leu Ser Arg Thr Cys Val Val Ser Gly Gly Ser Ile
            35                  40                  45

Ser Gly Tyr Tyr Tyr Trp Thr Trp Ile Arg Gln Thr Pro Gly Arg Gly
        50                  55                  60

Leu Glu Trp Ile Gly His Ile Tyr Gly Asn Gly Ala Thr Thr Asn Tyr
 65                  70                  75                  80

Asn Pro Ser Leu Lys Ser Arg Val Thr Ile Ser Lys Asp Thr Ser Lys
                85                  90                  95

Asn Gln Phe Phe Leu Asn Leu Asn Ser Val Thr Asp Ala Asp Thr Ala
            100                 105                 110

Val Tyr Tyr Cys Ala Arg Gly Pro Arg Pro Asp Cys Thr Thr Ile Cys
        115                 120                 125

Tyr Gly Gly Trp Val Asp Val Trp Gly Pro Gly Asp Leu Val Thr Val
    130                 135                 140
```

```
Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
                180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Ala Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```

(2) INFORMATION FOR SEQ ID NO:5:

(i) SEQUENCE CHARACTERISTICS:
        (A) LENGTH: 719 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..720

(ix) FEATURE:

(A) NAME/KEY: mat_peptide
        (B) LOCATION: 1..720

(xi) SEQUENCE DESCRIPTION: SEQ ID NO:5:

```
ATG AGC CTC CCT GCT CAG CTC CTC GGG CTG CTA TTG CTC TGC GTC CCC        48
Met Ser Leu Pro Ala Gln Leu Leu Gly Leu Leu Leu Leu Cys Val Pro
 1               5                  10                  15

GGG TCC AGT GGG GAA GTT GTG ATG ACT CAG TCT CCA CTG TCC CTT CCC        96
Gly Ser Ser Gly Glu Val Val Met Thr Gln Ser Pro Leu Ser Leu Pro
             20                  25                  30

ATC ACA CCT GGA GAG CCG GCC TCC ATC TCC TGT AGG TCT AGT CAA AGC       144
Ile Thr Pro Gly Glu Pro Ala Ser Ile Ser Cys Arg Ser Ser Gln Ser
         35                  40                  45

CTT AAA CAC AGT AAT GGA GAC ACC TTC CTG AGT TGG TAT CAG CAG AAG       192
Leu Lys His Ser Asn Gly Asp Thr Phe Leu Ser Trp Tyr Gln Gln Lys
     50                  55                  60

CCA GGC CAA CCT CCA AGG CTC CTG ATT TAT AAG GTT TCT AAC CGG GAC       240
Pro Gly Gln Pro Pro Arg Leu Leu Ile Tyr Lys Val Ser Asn Arg Asp
 65                  70                  75                  80

TCT GGG GTC CCA GAC AGA TTC AGC GGC AGT GGG GCA GGG ACA GAT TTC       288
Ser Gly Val Pro Asp Arg Phe Ser Gly Ser Gly Ala Gly Thr Asp Phe
                 85                  90                  95

ACA CTG AAA ATC AGC GCA GTG GAG GCT GAA GAT GTT GGG GTT TAT TTC       336
Thr Leu Lys Ile Ser Ala Val Glu Ala Glu Asp Val Gly Val Tyr Phe
            100                 105                 110

TGC GGG CAA GGT ACA AGG ACT CCT CCC ACT TTC GGC GGA GGG ACC AAG       384
Cys Gly Gln Gly Thr Arg Thr Pro Pro Thr Phe Gly Gly Gly Thr Lys
        115                 120                 125

GTG GAA ATC AAA CGT ACG GTG GCT GCA CCA TCT GTC TTC ATC TTC CCG       432
Val Glu Ile Lys Arg Thr Val Ala Ala Pro Ser Val Phe Ile Phe Pro
    130                 135                 140

CCA TCT GAT GAG CAG TTG AAA TCT GGA ACT GCC TCT GTT GTG TGC CTG       480
Pro Ser Asp Glu Gln Leu Lys Ser Gly Thr Ala Ser Val Val Cys Leu
145                 150                 155                 160

CTG AAT AAC TTC TAT CCC AGA GAG GCC AAA GTA CAG TGG AAG GTG GAT       528
Leu Asn Asn Phe Tyr Pro Arg Glu Ala Lys Val Gln Trp Lys Val Asp
                165                 170                 175

AAC GCC CTC CAA TCG GGT AAC TCC CAG GAG AGT GTC ACA GAG CAG GAC       576
Asn Ala Leu Gln Ser Gly Asn Ser Gln Glu Ser Val Thr Glu Gln Asp
            180                 185                 190

AGC AAG GAC AGC ACC TAC AGC CTC AGC AGC ACC CTG ACG CTG AGC AAA       624
Ser Lys Asp Ser Thr Tyr Ser Leu Ser Ser Thr Leu Thr Leu Ser Lys
        195                 200                 205

GCA GAC TAC GAG AAA CAC AAA GTC TAC GCC TGC GAA GTC ACC CAT CAG       672
Ala Asp Tyr Glu Lys His Lys Val Tyr Ala Cys Glu Val Thr His Gln
    210                 215                 220

GGC CTG AGC TCG CCC GTC ACA AAG AGC TTC AAC AGG GGA GAG TGT TGA       720
Gly Leu Ser Ser Pro Val Thr Lys Ser Phe Asn Arg Gly Glu Cys
225                 230                 235                 240
```

(2) INFORMATION FOR SEQ ID NO:6:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Leu Pro Ala Gln Leu Leu Gly Leu Leu Leu Leu Cys Val Pro
 1               5                  10                  15
```

```
Gly Ser Ser Gly Glu Val Val Met Thr Gln Ser Pro Leu Ser Leu Pro
             20                  25                  30
Ile Thr Pro Gly Glu Pro Ala Ser Ile Ser Cys Arg Ser Ser Gln Ser
         35                  40                  45
Leu Lys His Ser Asn Gly Asp Thr Phe Leu Ser Trp Tyr Gln Gln Lys
     50                  55                  60
Pro Gly Gln Pro Pro Arg Leu Leu Ile Tyr Lys Val Ser Asn Arg Asp
 65                  70                  75                  80
Ser Gly Val Pro Asp Arg Phe Ser Gly Ser Gly Ala Gly Thr Asp Phe
                 85                  90                  95
Thr Leu Lys Ile Ser Ala Val Glu Ala Glu Asp Val Gly Val Tyr Phe
            100                 105                 110
Cys Gly Gln Gly Thr Arg Thr Pro Thr Phe Gly Gly Gly Thr Lys
        115                 120                 125
Val Glu Ile Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235                 240

(2) INFORMATION FOR SEQ ID NO:7:

(i) SEQUENCE CHARACTERISTICS:
        (A) LENGTH: 1436 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1437

(ix) FEATURE:
        (A) NAME/KEY: mat_peptide
        (B) LOCATION: 1..1437

(xi) SEQUENCE DESCRIPTION: SEQ ID NO:7:

ATG GGT TGG AGC CTC ATC TTG CTC TTC CTT GTC GCT GTT GCT ACG CGT     48
Met Gly Trp Ser Leu Ile Leu Leu Phe Leu Val Ala Val Ala Thr Arg
 1               5                  10                  15

GTC CAG TGT GAG GTG CAA CTG GTG GAG TCT GGG GGA GGC TTG GTC CAG     96
Val Gln Cys Glu Val Gln Leu Val Glu Ser Gly Gly Gly Leu Val Gln
             20                  25                  30

CCT GGC GGG TCC CTG AGA GTC TCC TGT GCA GTC TCT GGA TTC ACC TTC    144
Pro Gly Gly Ser Leu Arg Val Ser Cys Ala Val Ser Gly Phe Thr Phe
         35                  40                  45

AGT GAC CAC TAC ATG TAT TGG TTC CGC CAG GCT CCA GGG AAG GGG CCG    192
Ser Asp His Tyr Met Tyr Trp Phe Arg Gln Ala Pro Gly Lys Gly Pro
     50                  55                  60
```

-continued

| | | |
|---|---|---|
| GAA TGG GTA GGT TTC ATT AGA AAC AAA CCG AAC GGT GGG ACA ACA GAA<br>Glu Trp Val Gly Phe Ile Arg Asn Lys Pro Asn Gly Gly Thr Thr Glu<br>65                          70                       75                          80 | 240 |
| TAC GCC GCG TCT GTG AAA GAC AGA TTC ACC ATC TCC AGA GAT GAT TCC<br>Tyr Ala Ala Ser Val Lys Asp Arg Phe Thr Ile Ser Arg Asp Asp Ser<br>                        85                       90                          95 | 288 |
| AAA AGC ATC GCC TAT CTG CAA ATG AGC AGC CTG AAA ATC GAG GAC ACG<br>Lys Ser Ile Ala Tyr Leu Gln Met Ser Ser Leu Lys Ile Glu Asp Thr<br>                    100                   105                   110 | 336 |
| GCC GTC TAT TAC TGT ACT ACA TCC TAC ATT TCA CAT TGT CGG GGT GGT<br>Ala Val Tyr Tyr Cys Thr Thr Ser Tyr Ile Ser His Cys Arg Gly Gly<br>          115                   120                   125 | 384 |
| GTC TGC TAT GGA GGT TAC TTC GAA TTC TGG GGC CAG GGC GCC CTG GTC<br>Val Cys Tyr Gly Gly Tyr Phe Glu Phe Trp Gly Gln Gly Ala Leu Val<br>130                        135                   140 | 432 |
| ACC GTC TCC TCA GCT AGC ACC AAG GGC CCA TCG GTC TTC CCC CTG GCA<br>Thr Val Ser Ser Ala Ser Thr Lys Gly Pro Ser Val Phe Pro Leu Ala<br>145                      150                   155                 160 | 480 |
| CCC TCC TCC AAG AGC ACC TCT GGG GGC ACA GCG GCC CTG GGC TGC CTG<br>Pro Ser Ser Lys Ser Thr Ser Gly Gly Thr Ala Ala Leu Gly Cys Leu<br>                    165                   170                   175 | 528 |
| GTC AAG GAC TAC TTC CCC GAA CCG GTG ACG GTG TCG TGG AAC TCA GGC<br>Val Lys Asp Tyr Phe Pro Glu Pro Val Thr Val Ser Trp Asn Ser Gly<br>                    180                   185                   190 | 576 |
| GCC CTG ACC AGC GGC GTG CAC ACC TTC CCG GCT GTC CTA CAG TCC TCA<br>Ala Leu Thr Ser Gly Val His Thr Phe Pro Ala Val Leu Gln Ser Ser<br>          195                   200                   205 | 624 |
| GGA CTC TAC TCC CTC AGC AGC GTG GTG ACC GTG CCC TCC AGC AGC TTG<br>Gly Leu Tyr Ser Leu Ser Ser Val Val Thr Val Pro Ser Ser Ser Leu<br>210                        215                   220 | 672 |
| GGC ACC CAG ACC TAC ATC TGC AAC GTG AAT CAC AAG CCC AGC AAC ACC<br>Gly Thr Gln Thr Tyr Ile Cys Asn Val Asn His Lys Pro Ser Asn Thr<br>225                      230                   235                 240 | 720 |
| AAG GTG GAC AAG AAA GCA GAG CCC AAA TCT TGT GAC AAA ACT CAC ACA<br>Lys Val Asp Lys Lys Ala Glu Pro Lys Ser Cys Asp Lys Thr His Thr<br>                    245                   250                   255 | 768 |
| TGC CCA CCG TGC CCA GCA CCT GAA CTC CTG GGG GGA CCG TCA GTC TTC<br>Cys Pro Pro Cys Pro Ala Pro Glu Leu Leu Gly Gly Pro Ser Val Phe<br>260                        265                   270 | 816 |
| CTC TTC CCC CCA AAA CCC AAG GAC ACC CTC ATG ATC TCC CGG ACC CCT<br>Leu Phe Pro Pro Lys Pro Lys Asp Thr Leu Met Ile Ser Arg Thr Pro<br>          275                   280                   285 | 864 |
| GAG GTC ACA TGC GTG GTG GTG GAC GTG AGC CAC GAA GAC CCT GAG GTC<br>Glu Val Thr Cys Val Val Val Asp Val Ser His Glu Asp Pro Glu Val<br>290                        295                   300 | 912 |
| AAG TTC AAC TGG TAC GTG GAC GGC GTG GAG GTG CAT AAT GCC AAG ACA<br>Lys Phe Asn Trp Tyr Val Asp Gly Val Glu Val His Asn Ala Lys Thr<br>305                        310                   315                 320 | 960 |
| AAG CCG CGG GAG GAG CAG TAC AAC AGC ACG TAC CGT GTG GTC AGC GTC<br>Lys Pro Arg Glu Glu Gln Tyr Asn Ser Thr Tyr Arg Val Val Ser Val<br>                    325                   330                   335 | 1008 |
| CTC ACC GTC CTG CAC CAG GAC TGG CTG AAT GGC AAG GAG TAC AAG TGC<br>Leu Thr Val Leu His Gln Asp Trp Leu Asn Gly Lys Glu Tyr Lys Cys<br>          340                   345                   350 | 1056 |
| AAG GTC TCC AAC AAA GCC CTC CCA GCC CCC ATC GAG AAA ACC ATC TCC<br>Lys Val Ser Asn Lys Ala Leu Pro Ala Pro Ile Glu Lys Thr Ile Ser<br>          355                   360                   365 | 1104 |
| AAA GCC AAA GGG CAG CCC CGA GAA CCA CAG GTG TAC ACC CTG CCC CCA<br>Lys Ala Lys Gly Gln Pro Arg Glu Pro Gln Val Tyr Thr Leu Pro Pro | 1152 |

-continued

```
            370                 375                 380
TCC CGG GAT GAG CTG ACC AAG AAC CAG GTC AGC CTG ACC TGC CTG GTC     1200
Ser Arg Asp Glu Leu Thr Lys Asn Gln Val Ser Leu Thr Cys Leu Val
385                 390                 395                 400

AAA GGC TTC TAT CCC AGC GAC ATC GCC GTG GAG TGG GAG AGC AAT GGG     1248
Lys Gly Phe Tyr Pro Ser Asp Ile Ala Val Glu Trp Glu Ser Asn Gly
                405                 410                 415

CAG CCG GAG AAC AAC TAC AAG ACC ACG CCT CCC GTG CTG GAC TCC GAC     1296
Gln Pro Glu Asn Asn Tyr Lys Thr Thr Pro Pro Val Leu Asp Ser Asp
            420                 425                 430

GGC TCC TTC TTC CTC TAC AGC AAG CTC ACC GTG GAC AAG AGC AGG TGG     1344
Gly Ser Phe Phe Leu Tyr Ser Lys Leu Thr Val Asp Lys Ser Arg Trp
        435                 440                 445

CAG CAG GGG AAC GTC TTC TCA TGC TCC GTG ATG CAT GAG GCT CTG CAC     1392
Gln Gln Gly Asn Val Phe Ser Cys Ser Val Met His Glu Ala Leu His
450                 455                 460

AAC CAC TAC ACG CAG AAG AGC CTC TCC CTG TCT CCG GGT AAA TGA         1437
Asn His Tyr Thr Gln Lys Ser Leu Ser Leu Ser Pro Gly Lys
465                 470                 475

(2) INFORMATION FOR SEQ ID NO:8:

(i) SEQUENCE CHARACTERISTICS:
        (A) LENGTH:  478 amino acids
        (B) TYPE: amino acid
        (D) TOPOLOGY: linear (ii) MOLECULE TYPE: protein (xi) SEQUENCE DESCRIPTION: SEQ ID NO:8:

Met Gly Trp Ser Leu Ile Leu Leu Phe Leu Val Ala Val Ala Thr Arg
  1               5                  10                  15

Val Gln Cys Glu Val Gln Leu Val Glu Ser Gly Gly Gly Leu Val Gln
                 20                  25                  30

Pro Gly Gly Ser Leu Arg Val Ser Cys Ala Val Ser Gly Phe Thr Phe
             35                  40                  45

Ser Asp His Tyr Met Tyr Trp Phe Arg Gln Ala Pro Gly Lys Gly Pro
     50                  55                  60

Glu Trp Val Gly Phe Ile Arg Asn Lys Pro Asn Gly Gly Thr Thr Glu
 65                  70                  75                  80

Tyr Ala Ala Ser Val Lys Asp Arg Phe Thr Ile Ser Arg Asp Asp Ser
                 85                  90                  95

Lys Ser Ile Ala Tyr Leu Gln Met Ser Ser Leu Lys Ile Glu Asp Thr
            100                 105                 110

Ala Val Tyr Tyr Cys Thr Thr Ser Tyr Ile Ser His Cys Arg Gly Gly
        115                 120                 125

Val Cys Tyr Gly Gly Tyr Phe Glu Phe Trp Gly Gln Gly Ala Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220
```

-continued

```
Gly Thr Gln Thr Tyr Ile Cys Asn Val Asn His Lys Pro Ser Asn Thr
225                 230                 235                 240

Lys Val Asp Lys Lys Ala Glu Pro Lys Ser Cys Asp Lys Thr His Thr
            245                 250                 255

Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly Lys
465                 470                 475
```

(2) INFORMATION FOR SEQ ID NO:9:

(i) SEQUENCE CHARACTERISTICS:
        (A) LENGTH: 710 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..711

(ix) FEATURE:
        (A) NAME/KEY: mat_peptide
        (B) LOCATION: 1..711

(xi) SEQUENCE DESCRIPTION: SEQ ID NO:9:

```
ATG AGG GTC CCC GCT CAG CTC CTG GGG CTC CTG CTG CTC TGG CTC CCA        48
Met Arg Val Pro Ala Gln Leu Leu Gly Leu Leu Leu Leu Trp Leu Pro
1               5                   10                  15

GGT GCA CGA TGT GAG TCT GTC CTG ACA CAG CCG CCC TCA GTG TCT GGG        96
Gly Ala Arg Cys Glu Ser Val Leu Thr Gln Pro Pro Ser Val Ser Gly
                20                  25                  30

GCC CCA GGG CAG AAG GTC ACC ATC TCG TGC ACT GGG AGC ACC TCC AAC       144
```

```
                              -continued

Ala Pro Gly Gln Lys Val Thr Ile Ser Cys Thr Gly Ser Thr Ser Asn
         35                  40                  45

ATT GGA GGT TAT GAT CTA CAT TGG TAC CAG CAG CTC CCA GGA ACG GCC       192
Ile Gly Gly Tyr Asp Leu His Trp Tyr Gln Gln Leu Pro Gly Thr Ala
         50                  55                  60

CCC AAA CTC CTC ATC TAT GAC ATT AAC AAG CGA CCC TCA GGA ATT TCT       240
Pro Lys Leu Leu Ile Tyr Asp Ile Asn Lys Arg Pro Ser Gly Ile Ser
65                  70                  75                  80

GAC CGA TTC TCT GGC TCC AAG TCT GGT ACC GCG GCC TCC CTG GCC ATC       288
Asp Arg Phe Ser Gly Ser Lys Ser Gly Thr Ala Ala Ser Leu Ala Ile
                 85                  90                  95

ACT GGG CTC CAG ACT GAG GAT GAG GCT GAT TAT TAC TGC CAG TCC TAT       336
Thr Gly Leu Gln Thr Glu Asp Glu Ala Asp Tyr Tyr Cys Gln Ser Tyr
                100                 105                 110

GAC AGC AGC CTG AAT GCT CAG GTA TTC GGA GGA GGG ACC CGG CTG ACC       384
Asp Ser Ser Leu Asn Ala Gln Val Phe Gly Gly Gly Thr Arg Leu Thr
                115                 120                 125

GTC CTA GGT CAG CCC AAG GCT GCC CCC TCG GTC ACT CTG TTC CCG CCC       432
Val Leu Gly Gln Pro Lys Ala Ala Pro Ser Val Thr Leu Phe Pro Pro
130                 135                 140

TCC TCT GAG GAG CTT CAA GCC AAC AAG GCC ACA CTG GTG TGT CTC ATA       480
Ser Ser Glu Glu Leu Gln Ala Asn Lys Ala Thr Leu Val Cys Leu Ile
145                 150                 155                 160

AGT GAC TTC TAC CCG GGA GCC GTG ACA GTG GCC TGG AAG GCA GAT AGC       528
Ser Asp Phe Tyr Pro Gly Ala Val Thr Val Ala Trp Lys Ala Asp Ser
                165                 170                 175

AGC CCC GTC AAG GCG GGA GTG GAG ACC ACC ACA CCC TCC AAA CAA AGC       576
Ser Pro Val Lys Ala Gly Val Glu Thr Thr Thr Pro Ser Lys Gln Ser
                180                 185                 190

AAC AAC AAG TAC GCG GCC AGC AGC TAC CTG AGC CTG ACG CCT GAG CAG       624
Asn Asn Lys Tyr Ala Ala Ser Ser Tyr Leu Ser Leu Thr Pro Glu Gln
                195                 200                 205

TGG AAG TCC CAC AGA AGC TAC AGC TGC CAG GTC ACG CAT GAA GGG AGC       672
Trp Lys Ser His Arg Ser Tyr Ser Cys Gln Val Thr His Glu Gly Ser
210                 215                 220

ACC GTG GAG AAG ACA GTG GCC CCT ACA GAA TGT TCA TGA                   711
Thr Val Glu Lys Thr Val Ala Pro Thr Glu Cys Ser
225                 230                 235

(2) INFORMATION FOR SEQ ID NO:10:

(i) SEQUENCE CHARACTERISTICS:
         (A) LENGTH: 236 amino acids
         (B) TYPE: amino acid
         (D) TOPOLOGY: linear (ii) MOLECULE TYPE: protein (xi) SEQUENCE DESCRIPTION: SEQ ID NO:10:

Met Arg Val Pro Ala Gln Leu Leu Gly Leu Leu Leu Leu Trp Leu Pro
1               5                   10                  15

Gly Ala Arg Cys Glu Ser Val Leu Thr Gln Pro Pro Ser Val Ser Gly
                20                  25                  30

Ala Pro Gly Gln Lys Val Thr Ile Ser Cys Thr Gly Ser Thr Ser Asn
         35                  40                  45

Ile Gly Gly Tyr Asp Leu His Trp Tyr Gln Gln Leu Pro Gly Thr Ala
         50                  55                  60

Pro Lys Leu Leu Ile Tyr Asp Ile Asn Lys Arg Pro Ser Gly Ile Ser
65                  70                  75                  80

Asp Arg Phe Ser Gly Ser Lys Ser Gly Thr Ala Ala Ser Leu Ala Ile
```

```
                        85                  90                  95
Thr Gly Leu Gln Thr Glu Asp Glu Ala Asp Tyr Tyr Cys Gln Ser Tyr
            100                 105                 110
Asp Ser Ser Leu Asn Ala Gln Val Phe Gly Gly Gly Thr Arg Leu Thr
            115                 120                 125
Val Leu Gly Gln Pro Lys Ala Ala Pro Ser Val Thr Leu Phe Pro Pro
130                 135                 140
Ser Ser Glu Glu Leu Gln Ala Asn Lys Ala Thr Leu Val Cys Leu Ile
145                 150                 155                 160
Ser Asp Phe Tyr Pro Gly Ala Val Thr Val Ala Trp Lys Ala Asp Ser
                165                 170                 175
Ser Pro Val Lys Ala Gly Val Glu Thr Thr Thr Pro Ser Lys Gln Ser
            180                 185                 190
Asn Asn Lys Tyr Ala Ala Ser Ser Tyr Leu Ser Leu Thr Pro Glu Gln
            195                 200                 205
Trp Lys Ser His Arg Ser Tyr Ser Cys Gln Val Thr His Glu Gly Ser
            210                 215                 220
Thr Val Glu Lys Thr Val Ala Pro Thr Glu Cys Ser
225                 230                 235

(2) INFORMATION FOR SEQ ID NO:11:

(i) SEQUENCE CHARACTERISTICS:
        (A) LENGTH: 1430 amino acids
        (B) TYPE: nucleic acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1431

(ix) FEATURE:
        (A) NAME/KEY: mat_peptide
        (B) LOCATION: 1..1431

(xi) SEQUENCE DESCRIPTION: SEQ ID NO:11:

ATG AAA CAC CTG TGG TTC TTC CTC CTC CTG GTG GCA GCT CCC AGA TGG      48
Met Lys His Leu Trp Phe Phe Leu Leu Leu Val Ala Ala Pro Arg Trp
  1               5                  10                  15

GTC CTG TCC CAG GTG CAG CTG CAG GAG TCG GGC CCA GGA CTG GTG AAG      96
Val Leu Ser Gln Val Gln Leu Gln Glu Ser Gly Pro Gly Leu Val Lys
             20                  25                  30

CCT TCG GAG ACC CTG TCC CTC ACC TGC GCT GTC TCT GGT GGC TCC ATC     144
Pro Ser Glu Thr Leu Ser Leu Thr Cys Ala Val Ser Gly Gly Ser Ile
         35                  40                  45

AGC GGT GGT TAT GGC TGG GGC TGG ATC CGC CAG CCC CCA GGG AAG GGG     192
Ser Gly Gly Tyr Gly Trp Gly Trp Ile Arg Gln Pro Pro Gly Lys Gly
     50                  55                  60

CTG GAG TGG ATT GGG AGT TTC TAT AGT AGT AGT GGG AAC ACC TAC TAC     240
Leu Glu Trp Ile Gly Ser Phe Tyr Ser Ser Ser Gly Asn Thr Tyr Tyr
 65                  70                  75                  80

AAC CCC TCC CTC AAG AGT CAA GTC ACC ATT TCA ACA GAC ACG TCC AAG     288
Asn Pro Ser Leu Lys Ser Gln Val Thr Ile Ser Thr Asp Thr Ser Lys
                 85                  90                  95

AAC CAG TTC TCC CTG AAG CTG AAC TCT ATG ACC GCC GCG GAC ACG GCC     336
Asn Gln Phe Ser Leu Lys Leu Asn Ser Met Thr Ala Ala Asp Thr Ala
            100                 105                 110

GTG TAT TAC TGT GTG AGA GAT CGT CTT TTT TCA GTT GTT GGA ATG GTT     384
```

```
                Val Tyr Tyr Cys Val Arg Asp Arg Leu Phe Ser Val Val Gly Met Val
                        115                 120                 125

TAC AAC AAC TGG TTC GAT GTC TGG GGC CCG GGA GTC CTG GTC ACC GTC                432
Tyr Asn Asn Trp Phe Asp Val Trp Gly Pro Gly Val Leu Val Thr Val
        130                 135                 140

TCC TCA GCT AGC ACC AAG GGC CCA TCG GTC TTC CCC CTG GCA CCC TCC                480
Ser Ser Ala Ser Thr Lys Gly Pro Ser Val Phe Pro Leu Ala Pro Ser
145                 150                 155                 160

TCC AAG AGC ACC TCT GGG GGC ACA GCG GCC CTG GGC TGC CTG GTC AAG                528
Ser Lys Ser Thr Ser Gly Gly Thr Ala Ala Leu Gly Cys Leu Val Lys
                165                 170                 175

GAC TAC TTC CCC GAA CCG GTG ACG GTG TCG TGG AAC TCA GGC GCC CTG                576
Asp Tyr Phe Pro Glu Pro Val Thr Val Ser Trp Asn Ser Gly Ala Leu
        180                 185                 190

ACC AGC GGC GTG CAC ACC TTC CCG GCT GTC CTA CAG TCC TCA GGA CTC                624
Thr Ser Gly Val His Thr Phe Pro Ala Val Leu Gln Ser Ser Gly Leu
            195                 200                 205

TAC TCC CTC AGC AGC GTG GTG ACC GTG CCC TCC AGC AGC TTG GGC ACC                672
Tyr Ser Leu Ser Ser Val Val Thr Val Pro Ser Ser Ser Leu Gly Thr
        210                 215                 220

CAG ACC TAC ATC TGC AAC GTG AAT CAC AAG CCC AGC AAC ACC AAG GTG                720
Gln Thr Tyr Ile Cys Asn Val Asn His Lys Pro Ser Asn Thr Lys Val
225                 230                 235                 240

GAC AAG AAA GCA GAG CCC AAA TCT TGT GAC AAA ACT CAC ACA TGC CCA                768
Asp Lys Lys Ala Glu Pro Lys Ser Cys Asp Lys Thr His Thr Cys Pro
                245                 250                 255

CCG TGC CCA GCA CCT GAA CTC CTG GGG GGA CCG TCA GTC TTC CTC TTC                816
Pro Cys Pro Ala Pro Glu Leu Leu Gly Gly Pro Ser Val Phe Leu Phe
            260                 265                 270

CCC CCA AAA CCC AAG GAC ACC CTC ATG ATC TCC CGG ACC CCT GAG GTC                864
Pro Pro Lys Pro Lys Asp Thr Leu Met Ile Ser Arg Thr Pro Glu Val
        275                 280                 285

ACA TGC GTG GTG GTG GAC GTG AGC CAC GAA GAC CCT GAG GTC AAG TTC                912
Thr Cys Val Val Val Asp Val Ser His Glu Asp Pro Glu Val Lys Phe
    290                 295                 300

AAC TGG TAC GTG GAC GGC GTG GAG GTG CAT AAT GCC AAG ACA AAG CCG                960
Asn Trp Tyr Val Asp Gly Val Glu Val His Asn Ala Lys Thr Lys Pro
305                 310                 315                 320

CGG GAG GAG CAG TAC AAC AGC ACG TAC CGT GTG GTC AGC GTC CTC ACC               1008
Arg Glu Glu Gln Tyr Asn Ser Thr Tyr Arg Val Val Ser Val Leu Thr
                325                 330                 335

GTC CTG CAC CAG GAC TGG CTG AAT GGC AAG GAG TAC AAG TGC AAG GTC               1056
Val Leu His Gln Asp Trp Leu Asn Gly Lys Glu Tyr Lys Cys Lys Val
            340                 345                 350

TCC AAC AAA GCC CTC CCA GCC CCC ATC GAG AAA ACC ATC TCC AAA GCC               1104
Ser Asn Lys Ala Leu Pro Ala Pro Ile Glu Lys Thr Ile Ser Lys Ala
        355                 360                 365

AAA GGG CAG CCC CGA GAA CCA CAG GTG TAC ACC CTG CCC CCA TCC CGG               1152
Lys Gly Gln Pro Arg Glu Pro Gln Val Tyr Thr Leu Pro Pro Ser Arg
    370                 375                 380

GAT GAG CTG ACC AAG AAC CAG GTC AGC CTG ACC TGC CTG GTC AAA GGC               1200
Asp Glu Leu Thr Lys Asn Gln Val Ser Leu Thr Cys Leu Val Lys Gly
385                 390                 395                 400

TTC TAT CCC AGC GAC ATC GCC GTG GAG TGG GAG AGC AAT GGG CAG CCG               1248
Phe Tyr Pro Ser Asp Ile Ala Val Glu Trp Glu Ser Asn Gly Gln Pro
                405                 410                 415

GAG AAC AAC TAC AAG ACC ACG CCT CCC GTG CTG GAC TCC GAC GGC TCC               1296
Glu Asn Asn Tyr Lys Thr Thr Pro Pro Val Leu Asp Ser Asp Gly Ser
            420                 425                 430
```

-continued

```
TTC TTC CTC TAC AGC AAG CTC ACC GTG GAC AAG AGC AGG TGG CAG CAG           1344
Phe Phe Leu Tyr Ser Lys Leu Thr Val Asp Lys Ser Arg Trp Gln Gln
        435                 440                 445

GGG AAC GTC TTC TCA TGC TCC GTG ATG CAT GAG GCT CTG CAC AAC CAC           1392
Gly Asn Val Phe Ser Cys Ser Val Met His Glu Ala Leu His Asn His
450                 455                 460

TAC ACG CAG AAG AGC CTC TCC CTG TCT CCG GGT AAA TGA                       1431
Tyr Thr Gln Lys Ser Leu Ser Leu Ser Pro Gly Lys
465                 470                 475
```

(2) INFORMATION FOR SEQ ID NO:12:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:12:

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Ala Val Ser Gly Gly Ser Ile
        35                  40                  45

Ser Gly Gly Tyr Gly Trp Gly Trp Ile Arg Gln Pro Pro Gly Lys Gly
    50                  55                  60

Leu Glu Trp Ile Gly Ser Phe Tyr Ser Ser Gly Asn Thr Tyr Tyr
65                  70                  75                  80

Asn Pro Ser Leu Lys Ser Gln Val Thr Ile Ser Thr Asp Thr Ser Lys
                85                  90                  95

Asn Gln Phe Ser Leu Lys Leu Asn Ser Met Thr Ala Ala Asp Thr Ala
            100                 105                 110

Val Tyr Tyr Cys Val Arg Asp Arg Leu Phe Ser Val Val Gly Met Val
        115                 120                 125

Tyr Asn Asn Trp Phe Asp Val Trp Gly Pro Gly Val Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Ala Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
```

-continued

```
                    290                 295                 300
Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                    325                 330                 335

Val Leu His Gln Asp Trp Leu Asn Gly Lys Glu Tyr Lys Cys Lys Val
                    340                 345                 350

Ser Asn Lys Ala Leu Pro Ala Pro Ile Glu Lys Thr Ile Ser Lys Ala
                    355                 360                 365

Lys Gly Gln Pro Arg Glu Pro Gln Val Tyr Thr Leu Pro Pro Ser Arg
                    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                    405                 410                 415

Glu Asn Asn Tyr Lys Thr Thr Pro Pro Val Leu Asp Ser Asp Gly Ser
                    420                 425                 430

Phe Phe Leu Tyr Ser Lys Leu Thr Val Asp Lys Ser Arg Trp Gln Gln
                    435                 440                 445

Gly Asn Val Phe Ser Cys Ser Val Met His Glu Ala Leu His Asn His
                    450                 455                 460

Tyr Thr Gln Lys Ser Leu Ser Leu Ser Pro Gly Lys
465                 470                 475
```